United States Patent [19]

Shalon et al.

[11] Patent Number: 5,585,873
[45] Date of Patent: Dec. 17, 1996

[54] AUTOMATED HAND-HELD KERATOMETER

[75] Inventors: Tadmor Shalon; Marvin L. Pund, both of Brentwood, Mo.

[73] Assignee: Alcon Laboratories, Inc., Fort Worth, Tex.

[21] Appl. No.: 775,194

[22] Filed: Oct. 11, 1991

[51] Int. Cl.$^6$ ..................................................... A61B 3/10
[52] U.S. Cl. ........................... 351/218; 351/211; 351/212
[58] Field of Search .................................. 351/205–218, 351/246, 247; 356/124–127

[56] References Cited

U.S. PATENT DOCUMENTS

| | | | |
|---|---|---|---|
| Re. 27,475 | 9/1972 | Volk | 351/246 |
| 1,006,825 | 10/1911 | Buchhop | 351/212 |
| 1,721,208 | 7/1929 | Currier et al. | 351/225 |
| 1,750,931 | 3/1930 | Kellner et al. | 351/212 |
| 2,174,308 | 9/1939 | Hartinger | 351/212 |
| 3,108,523 | 10/1963 | Nuchman | 351/206 |
| 3,141,396 | 7/1964 | Kimball et al. | 351/206 |
| 3,169,459 | 2/1965 | Friedberg et al. | 354/62 |
| 3,248,162 | 4/1966 | Knoll | 351/212 |
| 3,264,932 | 8/1966 | Hendricks | 356/32 |
| 3,404,936 | 10/1968 | Bennett et al. | 351/212 |
| 3,416,855 | 12/1968 | McClernon | 351/212 |
| 3,432,227 | 3/1969 | Soper | 351/212 |
| 3,442,579 | 5/1969 | Friedberg | 351/205 |
| 3,453,437 | 7/1969 | Westheimer et al. | 250/549 |
| 3,486,812 | 12/1969 | Volk | 351/205 |
| 3,487,069 | 12/1969 | Maselli | 250/218 |
| 3,536,384 | 10/1970 | Cocks | 351/212 |
| 3,542,458 | 11/1970 | Volk | 351/246 |
| 3,544,220 | 12/1970 | Kaye | 356/354 |
| 3,552,837 | 1/1971 | Volk | 351/212 |
| 3,572,909 | 3/1971 | VanPatten et al. | 351/6 |
| 3,598,478 | 8/1971 | Townsley | 351/206 |

(List continued on next page.)

FOREIGN PATENT DOCUMENTS

3125494A1  6/1981  Germany .

OTHER PUBLICATIONS

R. E. Frazer, et al., National Aeronautics and Space Administration, "NASA TECH BRIEF/REAL–TIME KERATOMETER", Aug. 1988–2 pages–Springfield, VA. U.S.
Terence C. Honikman, PhD, *Trends In Iols & Refractive Surgery*, Oct. 2, 1985, 8 pages.
Allergan Humphrey, "Auto Kerometer", 1989 (2 pages).
MARCO, "Keratometer I and Keratometer II", 1989 (4 pages).
TOPCON, "Computerized Lensmeter CL–2000", 1989, (4 pages).
ALLERGAN HUMPHREY, "Humphrey Lens Analyzer", 1989, (2 pages).
TOPCON, "Digital Projection Lensmeter LM–P5", 1989, (3 pages).
MARCO, Lensmeter 101 and Lensmeter 201, (1 page).
TOPCON, "Topcon Lensmeter LM–6/LM–6E", 1988, (4 pages).
TOPCON, "Lensmeter LM–S1", 1989, (2 pages).
TOPCON, "KR–3000 Auto Kerato–Refractometer", 1990, (4 pages).
MARCO TECHNOLOGIES, "ARK–2000 Automatic Refractor/Keratometer", (2 pages).
MARCO TECHNOLOGIES, "LM–870 Automatic Lensmeter", (2 pages).

*Primary Examiner*—Thong Nguyen
*Attorney, Agent, or Firm*—Howell & Haferkamp, L.C.

[57] ABSTRACT

An automated portable keratometer includes a hand held housing and is battery powered. A projection system projects collimated light sources at equal converging angles to an optical axis which extends outside the housing. A camera, including an imaging device, and telocentric objective lens are aligned along the optical axis in the housing. The projection system projects a known pattern of collimated light sources onto a patient's eye. The reflected images of these light sources is captured by the camera and imaging device. Derivation of the distances between certain reflected images can be converted by known algorithms into radii of curvature of the eye. Alignment leveling, and other features can be included with the keratometer. The device can also be used to measure other curved surfaces.

17 Claims, 35 Drawing Sheets

U.S. PATENT DOCUMENTS

| | | | |
|---|---|---|---|
| 3,634,003 | 1/1972 | Guyton | 351/17 |
| 3,664,631 | 5/1972 | Guyton | 351/27 |
| 3,669,530 | 6/1972 | Guyton | 351/17 |
| 3,797,921 | 3/1974 | Kilmer et al. | 351/206 |
| 3,871,772 | 3/1975 | Munnerlyn et al. | 356/153 |
| 3,879,113 | 4/1975 | Howland et al. | 351/7 |
| 3,883,233 | 5/1975 | Guiljno | 351/6 |
| 3,932,030 | 1/1976 | Hasegawa et al. | 351/212 |
| 3,969,019 | 7/1976 | Nohda | 351/212 |
| 3,972,602 | 8/1976 | Inns | 351/245 |
| 4,019,813 | 4/1977 | Cornsweet et al. | 351/212 |
| 4,021,102 | 5/1977 | Iizuka | 351/13 |
| 4,157,859 | 6/1979 | Terry | 359/375 |
| 4,159,867 | 7/1979 | Achatz et al. | 351/212 |
| 4,162,828 | 7/1979 | Trachtman | 351/9 |
| 4,165,744 | 8/1979 | Cravy et al. | 128/745 |
| 4,172,639 | 10/1979 | Lang et al. | 351/211 |
| 4,180,323 | 12/1979 | Persson et al. | 356/3 |
| 4,196,980 | 4/1980 | Heine | 351/211 |
| 4,199,816 | 4/1980 | Humphrey | 364/571.04 |
| 4,220,401 | 9/1980 | Muchel | 351/211 |
| 4,256,385 | 3/1981 | Cohen et al. | 351/13 |
| 4,293,198 | 10/1981 | Kohayakawa et al. | 351/13 |
| 4,293,199 | 10/1981 | Wada et al. | 351/13 |
| 4,304,468 | 12/1981 | Wada | 351/13 |
| 4,312,574 | 1/1982 | Wilms | 351/206 |
| 4,315,672 | 2/1982 | Müller et al. | 351/212 |
| 4,353,625 | 10/1982 | Nohda et al. | 351/13 |
| 4,355,871 | 10/1982 | Nevyas et al. | 351/212 |
| 4,367,019 | 1/1983 | Kitao et al. | 351/211 |
| 4,372,655 | 2/1983 | Matsumura et al. | 351/206 |
| 4,373,787 | 2/1983 | Crane et al. | 351/210 |
| 4,390,255 | 6/1983 | Nohda et al. | 351/212 |
| 4,396,261 | 8/1983 | Herbert | 351/247 |
| 4,407,572 | 10/1983 | Humphrey | 351/212 |
| 4,410,243 | 10/1983 | Fürste | 351/211 |
| 4,420,228 | 12/1983 | Humphrey | 351/212 |
| 4,421,391 | 12/1983 | Matsumura et al. | 351/211 |
| 4,429,960 | 2/1984 | Mocilac et al. | 351/212 |
| 4,440,477 | 4/1984 | Schachar | 351/212 |
| 4,444,476 | 4/1984 | Simon et al. | 351/211 |
| 4,453,808 | 6/1984 | Takahashi et al. | 351/208 |
| 4,491,398 | 1/1985 | Karickhoff | 351/211 |
| 4,533,221 | 8/1985 | Trachtman | 351/203 |
| 4,540,254 | 9/1985 | Humphrey | 351/212 |
| 4,569,576 | 2/1986 | Karpov et al. | 351/212 |
| 4,572,628 | 2/1986 | Nohda | 351/212 |
| 4,588,270 | 5/1986 | Tamski | 351/212 |
| 4,597,648 | 7/1986 | Feldon et al. | 351/212 |
| 4,606,623 | 8/1986 | Schachar | 351/212 |
| 4,609,287 | 9/1986 | Kohayakawa | 356/124 |
| 4,637,700 | 1/1987 | Krueger | 351/211 |
| 4,660,945 | 4/1987 | Trachtman | 351/203 |
| 4,660,946 | 4/1987 | Nakamura et al. | 351/212 |
| 4,662,730 | 5/1987 | Outwater et al. | 351/212 |
| 4,692,003 | 9/1987 | Adachi et al. | 351/212 |
| 4,697,895 | 10/1987 | Sekiguchi et al. | 351/243 |
| 4,705,037 | 11/1987 | Peyman et al. | 128/305 |
| 4,710,003 | 12/1987 | Masuda et al. | 351/212 |
| 4,730,917 | 3/1988 | Krueger | 351/211 |
| 4,755,043 | 7/1988 | Carter | 351/211 |
| 4,761,070 | 8/1988 | Fukuma | 351/205 |
| 4,761,071 | 8/1988 | Baron | 351/212 |
| 4,768,875 | 9/1988 | Müller | 351/212 |
| 4,772,114 | 9/1988 | Fukui et al. | 351/211 |
| 4,772,115 | 9/1988 | Gersten et al. | 351/212 |
| 4,779,973 | 10/1988 | Miller et al. | 351/212 |
| 4,828,381 | 5/1989 | Shindo | 351/211 |
| 4,848,896 | 7/1989 | Matsumoto | 351/211 |
| 4,863,260 | 9/1989 | Gersten et al. | 351/212 |
| 4,881,807 | 11/1989 | Luce et al. | 351/208 |
| 4,903,706 | 2/1990 | Vila-Cora et al. | 351/209 |
| 5,011,276 | 4/1991 | Iwamoto | 351/211 |
| 5,157,427 | 10/1992 | Humphrey | 351/211 |
| 5,189,449 | 2/1993 | Perkins | 351/211 |

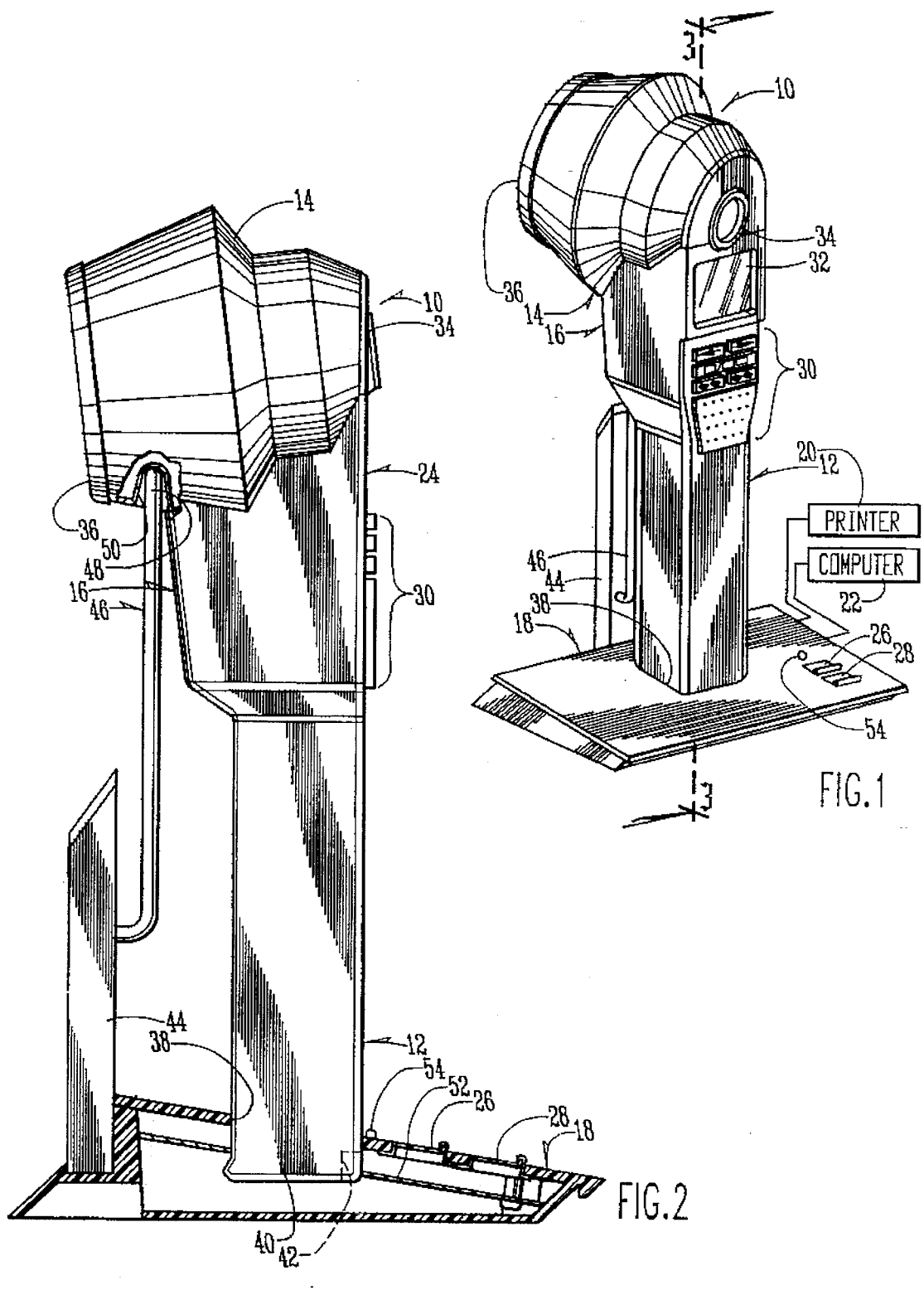

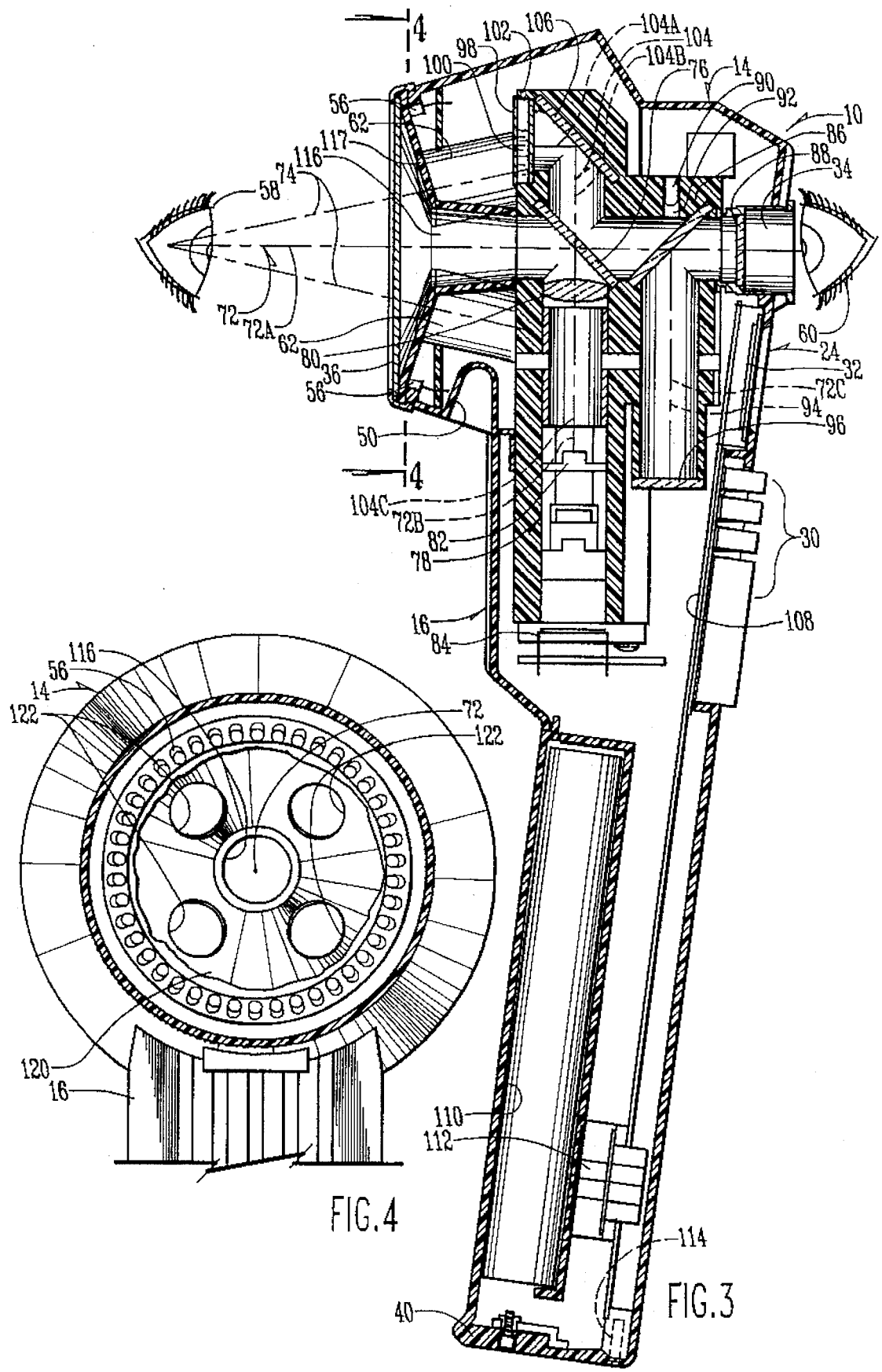

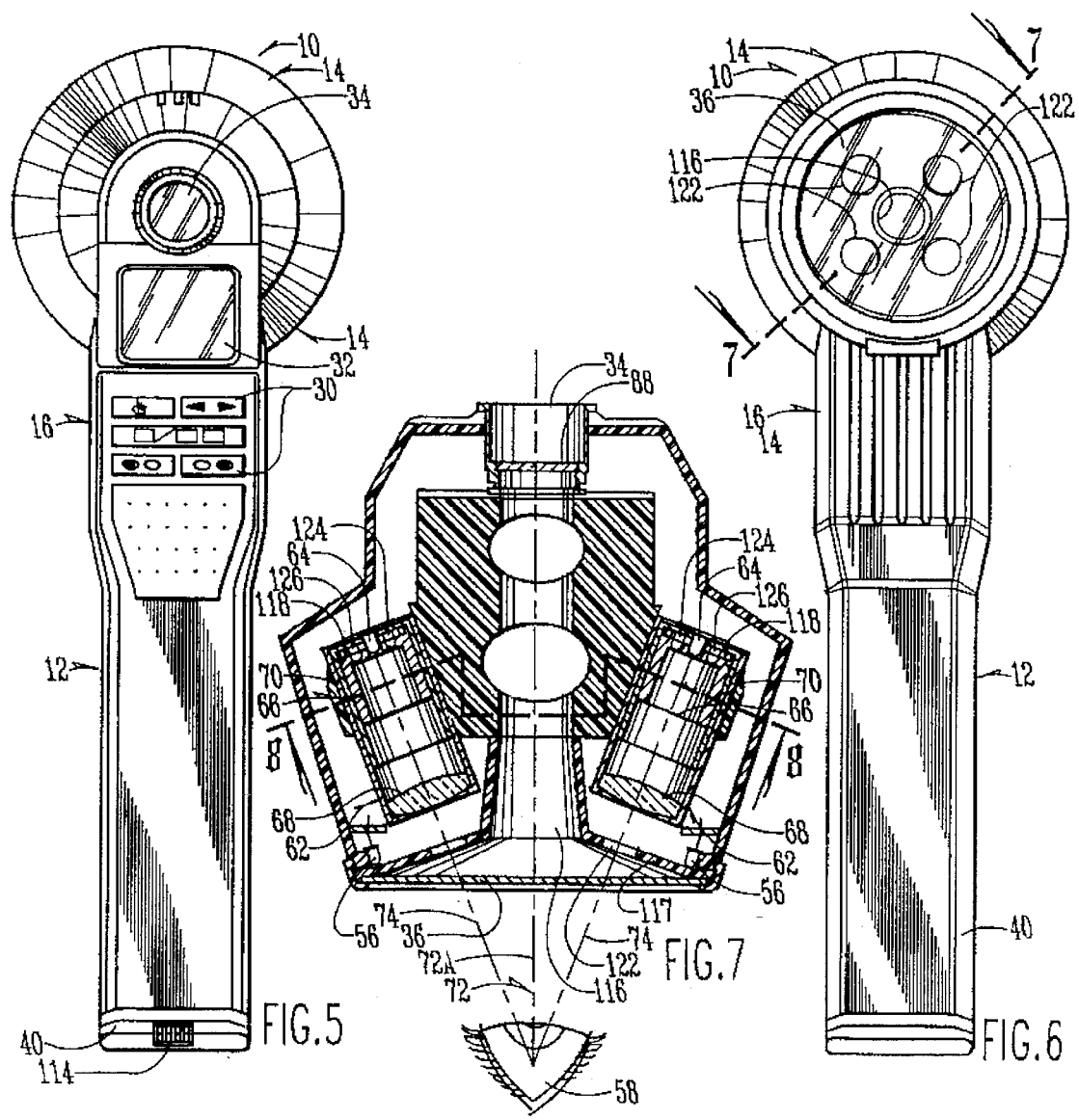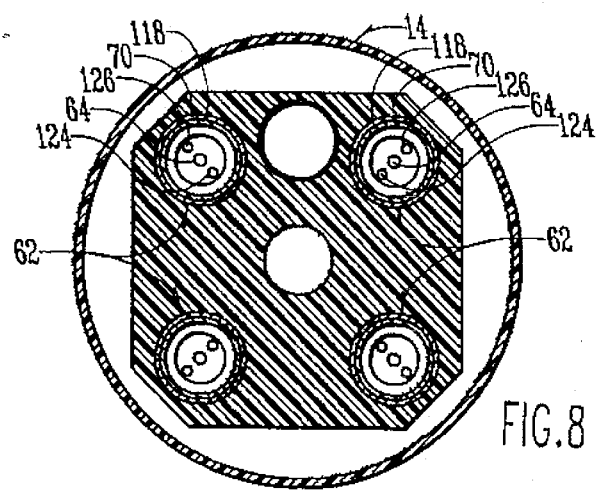

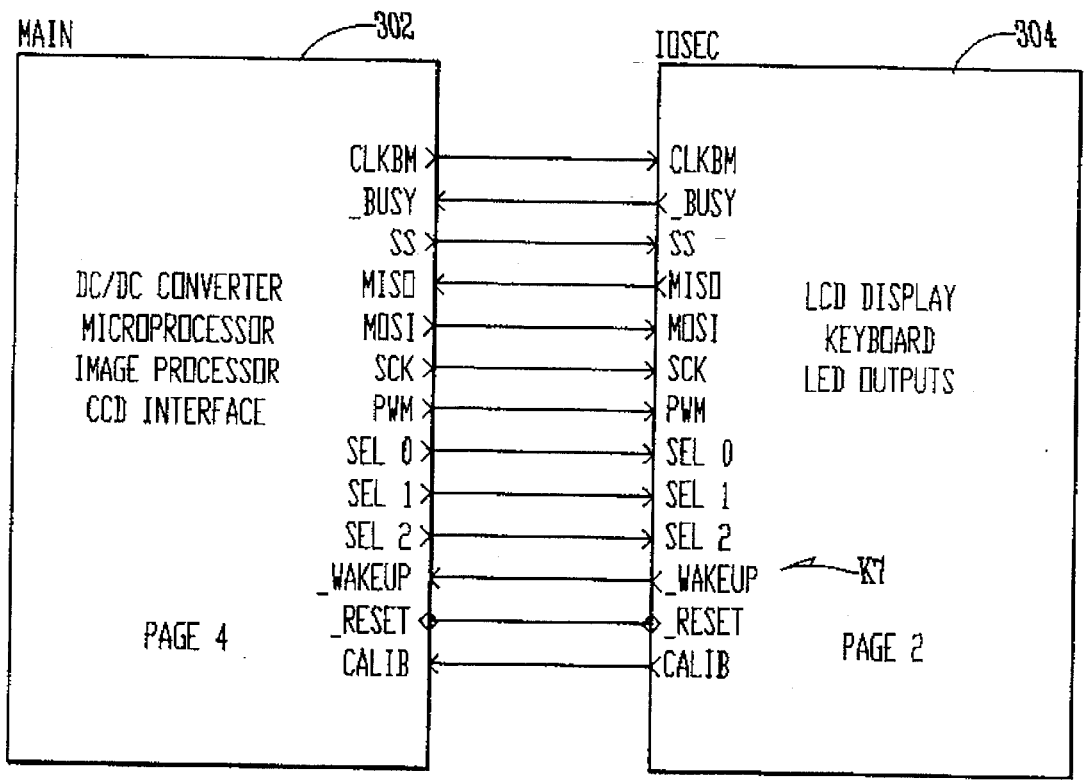
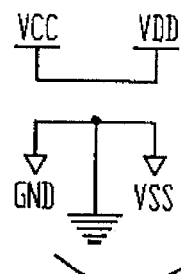
FIG. 17

FIG. 34A

| EVENTS:<br>STATES: | NO EVENT | SELECT KEY | SCROLL KEY | CLEAR KEY | RIGHT EYE KEY | LEFT EYE KEY | ALIGN KEY |
|---|---|---|---|---|---|---|---|
| HOLD | DO NOTHING<br>---<br>HOLD | PREPARE FOR DISPLAY MODE<br>FNE= DISPLAY<br>SELECT KEY | PREPARE FOR DISPLAY MODE<br>FNE= DISPLAY<br>SELECT KEY | PREPARE FOR DISPLAY MODE<br>FNE= DISPLAY<br>SELECT KEY | PREPARE FOR DISPLAY MODE<br>FNE= DISPLAY<br>SELECT KEY | PREPARE FOR DISPLAY MODE<br>FNE= DISPLAY<br>SELECT KEY | PREPARE FOR DISPLAY MODE<br>FNE= DISPLAY<br>SELECT KEY |
| DISPLAY | DO NOTHING<br>---<br>DISPLAY | OPTIONS MENU SELECT<br>---<br>OPTIONS | PRINT RESULTS<br>---<br>DISPLAY | CLEAR READING<br>---<br>DISPLAY | SELECT RIGHT EYE<br>---<br>DISPLAY | SELECT DISPLAY<br>---<br>LEFT EYE | MJRE MODE<br>---<br>DISPLAY |
| THRESHOLD | DO NOTHING<br>---<br>THRESHOLD | DO NOTHING<br>---<br>THRESHOLD | DO NOTHING<br>---<br>THRESHOLD | DO NOTHING<br>---<br>DISPLAY | DO NOTHING<br>---<br>THRESHOLD | DO NOTHING<br>---<br>THRESHOLD | DO NOTHING<br>---<br>THRESHOLD |
| MEASURE | DO NOTHING<br>---<br>MEASURE | DO NOTHING<br>---<br>MEASURE | DO NOTHING<br>---<br>MEASURE | POST MEASURING<br>---<br>DISPLAY | DO NOTHING<br>---<br>MEASURE | DO NOTHING<br>---<br>MEASURE | DO NOTHING<br>---<br>MEASURE |
| OPTIONS | DO NOTHING<br>---<br>OPTIONS | OPTIONS MENU SELECT<br>---<br>OPTIONS | OPTIONS MENU SCROLL<br>---<br>OPTIONS | EXIT OPTIONS<br>---<br>OPTIONS | DO NOTHING<br>---<br>OPTIONS | DO NOTHING<br>---<br>OPTIONS | EXIT OPTIONS<br>FNE= HIDDEN<br>SELECT KEY |
| HIDDEN | DO NOTHING<br>---<br>HIDDEN | HIDDEN MENU SELECT<br>---<br>HIDDEN | HIDDEN MENU SCROLL<br>---<br>HIDDEN | EXIT HIDDEN<br>---<br>HIDDEN | DO NOTHING<br>---<br>HIDDEN | DO NOTHING<br>---<br>HIDDEN | DO NOTHING<br>---<br>HIDDEN |

FIG. 34B

| | MEASURE KEY | PRINT KEY | ON FLAG | REPEAT FLAG | FAILED FLAG | PC MESSAGE | FIELD TEST TERMINAL | TIMEOUT |
|---|---|---|---|---|---|---|---|---|
| | PREPARE FOR DISPLAY MODE / FNE=DISPLAY MEASURE KEY | PREPARE FOR DISPLAY MODE / FNE=DISPLAY PRINT KEY | PREPARE FOR DISPLAY MODE / FNE=DISPLAY ON FLAG | PREPARE FOR DISPLAY MODE / FNE=DISPLAY REPEAT FLAG | PREPARE FOR DISPLAY MODE / FNE=DISPLAY FAILED FLAG | PREPARE FOR DISPLAY MODE / FNE=DISPLAY PC MESSAGE | PREPARE FOR DISPLAY MODE / FNE=DISPLAY FLD.TST.TERM. | PREPARE FOR DISPLAY MODE / SLEEP |
| | PRE THRESHOLDING / THRESHOLD | PRINT RESULTS / DISPLAY | DO NOTHING / DISPLAY | DO NOTHING / DISPLAY | DO NOTHING / DISPLAY | COMMAND FROM PC / DISPLAY | FIELD TEST TERMINAL / DISPLAY | PREPARE FOR HOLD MODE / HOLD |
| | DO NOTHING / THRESHOLD | DO NOTHING / THRESHOLD | PRE MEASURING / MEASURE | THRESHOLDING / THRESHOLD | DO NOTHING / DISPLAY | COMMAND FROM PC / DISPLAY | FIELD TEST TERMINAL / DISPLAY | DO NOTHING / THRESHOLD |
| | DO NOTHING / MEASURE | DO NOTHING / MEASURE | POST MEASURING / MEASURE | MEASURING / MEASURE | REALIGN / MEASURE | COMMAND FROM PC / DISPLAY | FIELD TEST TERMINAL / DISPLAY | DO NOTHING / MEASURE |
| | DO NOTHING / OPTIONS | DO NOTHING / OPTIONS | POST OPTIONS / DISPLAY | DO NOTHING / OPTIONS | DO NOTHING / OPTIONS | DO NOTHING / OPTIONS | DO NOTHING / OPTIONS | DO NOTHING / OPTIONS |
| | DO NOTHING / HIDDEN | DO NOTHING / HIDDEN | POST HIDDEN / DISPLAY | DO NOTHING / HIDDEN | DO NOTHING / HIDDEN | DO NOTHING / HIDDEN | DO NOTHING / HIDDEN | DO NOTHING / HIDDEN |

AUTOMATED HAND-HELD KERATOMETER

I. BACKGROUND OF THE INVENTION

A. Field of the Invention

This invention relates to keratometers, and in particular, to an automated keratometer, including one that is relatively small in size, and hand-held.

B. Problems in the Art

1. Definition of Keratometer

A keratometer is an instrument utilized to measure the radius of curvature of a curved surface; generally that of an eye. Readings are usually taken of the radius of curvature of two different axes, as well as the angle of those two different axes. The results are utilized to estimate the dioptric power along each axis, which can then be used to estimate refractive power and/or shape of the particular eye being tested.

The primary readings taken by the keratometer are the curvature along the axis of maximum curvature, the curvature along the axis of minimum curvature, and the angles of the two curvature axes with respect to the horizontal axis. These types of readings are used to fit eye glasses or contact lenses. Accuracy is therefore important. This is particularly true for contact lenses which are placed in direct contact with the surface of the eye.

Keratometers are also used to examine the pathology of the cornea for such things as keratoconus, dystrophies, and stigmatism, corneal problems, and abnormal curvature. It is usually a standard piece of equipment for an optometric or ophthalmic examination.

2. Manual Keratometers

Keratometers originally were all manually operated optical devices. They continue to be used today. A manual keratometer requires the patient's head to be accurately positioned and maintained in position with respect to the device. Manual dials are then turned by the operator to create some optically perceivable condition in the device. Some manual keratometers require the operator to align several circles in a particular orientation while viewing the patient's eye. A reading is then taken from the dials or, in the earliest versions, a chart is consulted to obtain the readings. These readings must then be manually transcribed.

Manual keratometers represent a substantial investment, and require substantial space in an office for the patient and operator to complete the procedure. Perhaps the most significant problems of manual keratometers are the amount of time required to take the appropriate readings and the amount of training and expertise needed by the operator to achieve reliable results.

Operation of these devices requires some level of advanced skills and knowledge. They generally must be operated by ophthalmologists, optometrists, or perhaps opticians. Some judgment and experience on a rather high level is needed to take and interpret the readings and create the conditions needed to ensure the readings will be generally accurate and reliable.

Manual operation includes potential for human error. The operator must take significant care in the procedures and may need to retake the measurements to double check original measurements. Sometimes interpretation of results is needed, requiring substantial expertise.

Manual keratometers generally allow apical measurements only, and do not allow peripheral Cornea measurements. New surgeries and treatment techniques require accurate peripheral measurements. Manual keratometers also have a number of moving parts and rely on expensive high precision optical elements. Calibration and the maintenance of calibration is therefore very important. All of the above discussed problems leave room for improvement in this field.

3. Automated Keratometers

In an attempt to meet these needs, automated keratometers have been developed. These devices generally utilize some electro-optical combination to provide keratometric readings which can be displayed, stored, or sometimes printed. Major deficiencies of present automated systems are as follows.

Many of these devices require a substantial amount of manual operation. Some require that the operator align the instrument to the eye by viewing and aligning images in the keratometer optical system. One requires alignment of lights and geometric figures. This requires the operator to subjectively determine whether a certain somewhat subjective condition exists, introducing an element of error risk.

These systems require the user's head to be fixed with respect to the machine. Normally this will include a chin or head brace and necessitates constant vigilance to ensure that the head is kept in a fixed position.

Most automated keratometers take up a substantial amount of space. Many consume the better part of a medium sized table. The operator sits on one side of the machine, while the patient sits on the other. It might also require associated equipment, taking even more room.

It is to be understood that the size of some automatic keratometers is so large that it must be put in a separate room, or at least a room outside of the normal examination room. This requires additional patient shuffling from the waiting area to the examination room, to the room for the keratometric readings, and so on. This further complicates and is an obstacle to efficiency of patient processing. It can create a bottle neck if all the patients need to go to a separate room, have keratometric readings taken, and then return to the examination room.

Auxiliary equipment such as motorized tables and chairs is sometimes utilized with the automated keratometer to accurately position the patient. This adds significantly to the cost and to the space needed for operation. These machines tend to be heavy and their inner contents somewhat fragile. Most also require precise optical components. They are also extremely costly as compared with manual keratometers.

Automated keratometers therefore include potential errors associated with the requirement of human verification or subjective determinations. They also rely on precise, costly optical components which must be maintained in precise alignment and calibration.

They also require a high level of operator training and expertise. The added cost and space required for these devices may therefore offset any improvement they provide in time or accuracy.

4. Size and Space Considerations

Keratometers are generally utilized in the offices of ophthalmologists and optometrists. They may also be utilized by opticians. Keratometric measurements are often taken for each patient's visit. This is especially true for those who wear contacts. The keratometer measures the curvature of the eye. The contact, to be fitted properly, is placed directly adjacent to the eye. Most ophthalmologists and optometrists set up "lanes" in each examination room. Patients are called from the waiting room and moved through a series of equipments or stations in the lane during eye examinations.

Much consideration is given into maximation of patient flow or turnover. Several patient rooms with completely furnished lanes are therefore utilized. While one patient is put through the measurements in the lanes, another patient can be brought into another room and prepared. A third patient who has finished with measurements can then be readied for completion of the exam while the ophthalmologist or optometrist goes to another room and/or another patient.

Time and space are primary factors in improving the efficiency of patient flow. More time to perform the keratometric measurements, translates into less time available to do other things. More room for the keratometer, translates into less room for other equipment, or a reduced number of patient rooms; which translates into more square footage and more costly office space. Less costly and smaller manual keratometers, are more time consuming to operate. Automated keratometers, take up much more room and are more cumbersome.

With current keratometers it is not possible to delegate the taking of keratometric readings to staff members. They require either substantial training and/or substantial expertise, knowledge, and skill to operate. These traits may not be readily available in staff members. At a minimum, there is a requirement of extensive or long training and experience. Otherwise accuracy and reliability may suffer substantially.

While automated keratometers are generally much more costly than manual keratometers, the trend is to purchase and use automated keratometers. There is a perception, perhaps primarily by patients, that automated, higher technology equipment is a necessity for competent and successful ophthalmological and optometric practice.

5. Needs in the Art

Although automated keratometers are available, their problems and deficiencies are readily apparent as discussed above. A need therefore exists for an automated keratometer which is small in size, takes all keratometric readings quickly, accurately and reliably, and is easy for staff workers or technicians to operate.

There is also a need for a portable automated keratometer that need not be placed on a table nor require constraint of the patient's head. There is also a need for an automated keratometer which is less costly than current automated keratometers.

6. Objects

It is therefore a principal object of the present invention to provide an automated keratometer which solves the problems or improves over the deficiencies in the art.

Another object of the present invention is to provide an automated keratometer which is substantially automatic and eliminates substantially the margin of human error in its operation.

A still further object of the present invention is to provide an automated keratometer which can be hand held, is easily maneuverable, light weight, and can even be battery powered.

A still further object of the present invention is to provide an automated keratometer which does not require fixed positioning of the patient's head or eye with respect to the device.

Another object of the present invention is to provide an automated keratometer which has an automated alignment system to ensure alignment during measurement.

Another object of the present invention is to provide an automated keratometer which helps patients fix on a target to eliminate possible measurement errors caused of loss of fixation or movement of the eye.

Another object of the present invention is to provide an automated keratometer which automatically processes, displays, and stores or prints keratometric readings.

Another object of the present invention is to provide an automated keratometer which allows the user to simultaneously view the patient's eye.

These and other objects, features, and advantages of the present invention will become more apparent with reference to the accompanying specification and claims.

II. SUMMARY OF THE INVENTION

The invention is an automated keratometer which is portable and hand held. It is freely and easily movable into a position near a patient's eye and does not require the patient to have his/her head fixedly secured.

A portable housing contains a projector system and a camera system. The projector system includes a plurality of collimated light sources which project out of the housing onto the patient's eye. The housing is moved to a position where the projected light sources circumferentially surround the optical axis of the eye. The position of the housing is also adjusted so that the optical axis of the eye is made generally co-linear with an optical axis through the keratometer through the camera means. The camera means is positioned telecentrically along the optical axis. It captures the reflected image of the projected light sources on the eye. A processing means then determines the relative spatial locations of the reflected light sources and derives radii of curvature measurements according to an algorithm in the processing means.

The invention includes optional features and enhancements such as alignment means for automatically indicating alignment along the optical axis. A fixation means is also provided to assist the patient in fixing his/her eye during measurement. A leveling means can also be incorporated to automatically indicate the housing is in a level position.

The keratometer can be battery powered and optionally can be rechargeable. It can include a display so that the calculated keratometric measurements can be observed by the operator. It can also store those measurements to be printed out or otherwise documented.

The invention therefore will completely free the operator and patient of the requirement of dealing with a table top device taking up substantial space, and will take quick and accurate readings. Its level of automation reduces potential for error and its combination of components reduces the cost to manufacture, assemble, and therefore retail the device.

III. BRIEF DESCRIPTION OF THE DRAWINGS

FIG. 1 is a perspective view of a preferred embodiment of the invention;

FIG. 2 is a slightly enlarged side elevational and partial sectional view of FIG. 1;

FIG. 3 is a still further enlarged sectional view taken along line 3—3 of FIG. 1;

FIG. 4 is a partial section, partial cutaway view, taken generally along line 4—4 of FIG. 3;

FIG. 5 is an enlarged front elevational view of FIG. 1;

FIG. 6 is an enlarged back elevational view of FIG. 1;

FIG. 7 is a still further enlarged sectional view taken along line 7—7 of FIG. 6;

FIG. 8 is still a further enlarged sectional view taken generally along line 8—8 of FIG. 7;

Figure 13A:
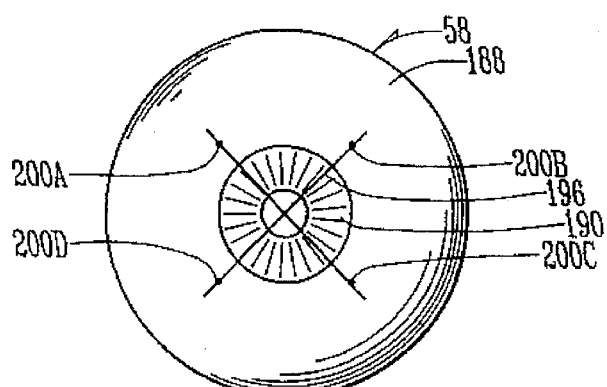
Figure 13B:
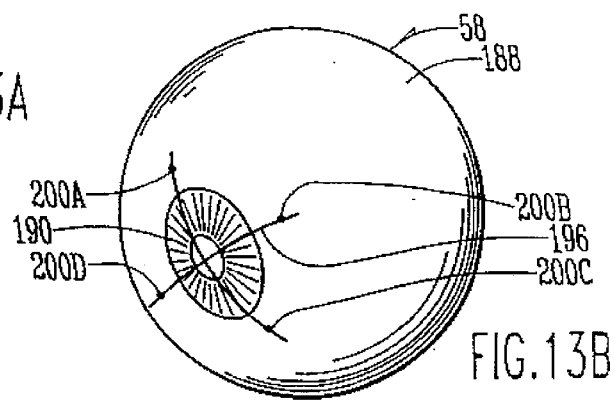
Figure 13C:
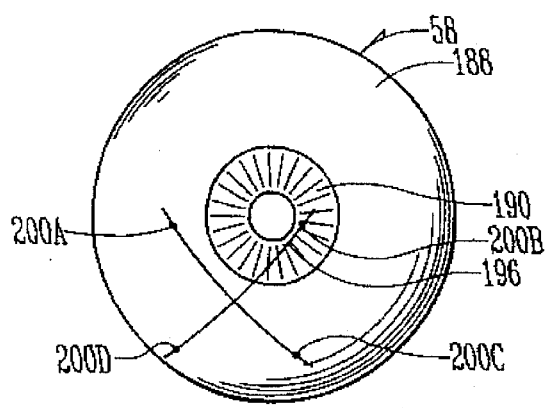
Figure 13D:
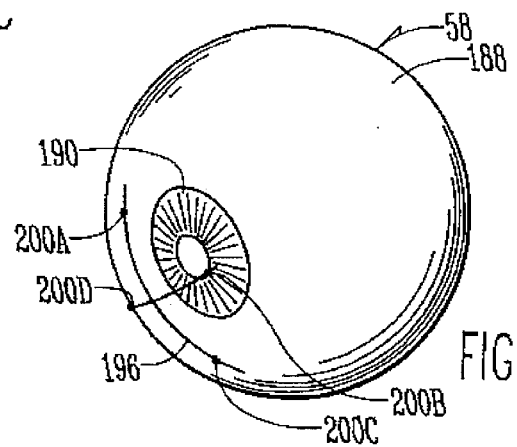
Figure 14A:
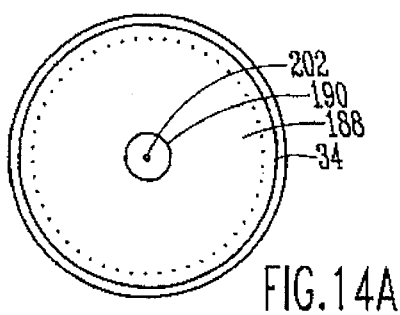
Figure 14B:
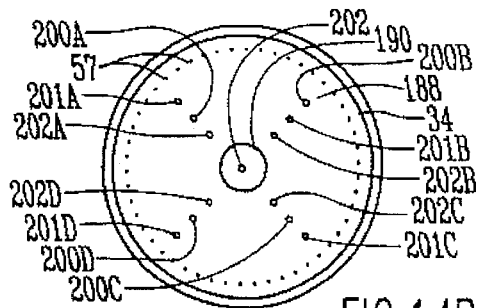
Figure 14C:
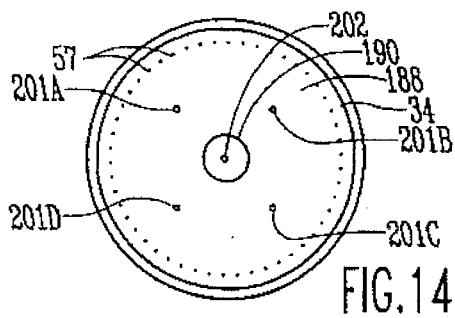
Figure 14D:
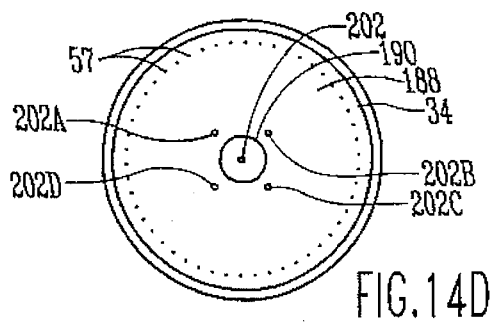
Figure 14E:
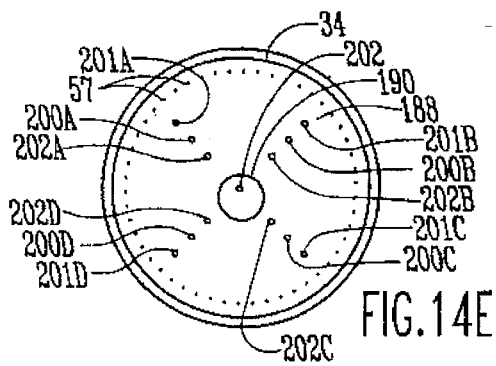
Figure 14F:
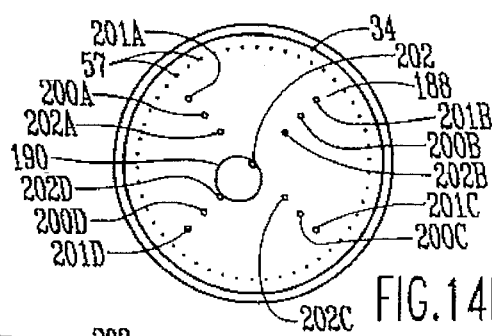
Figure 14G:
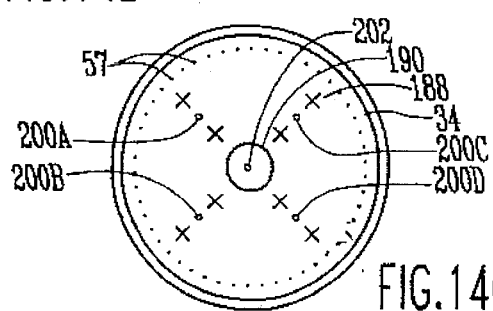
Figure 15:
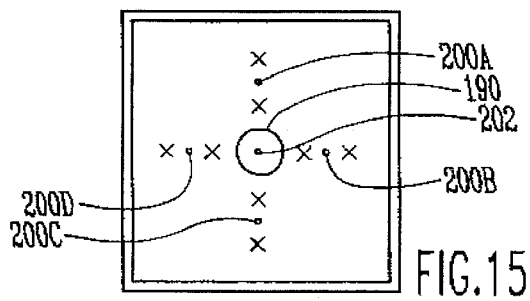
Figure 16A:
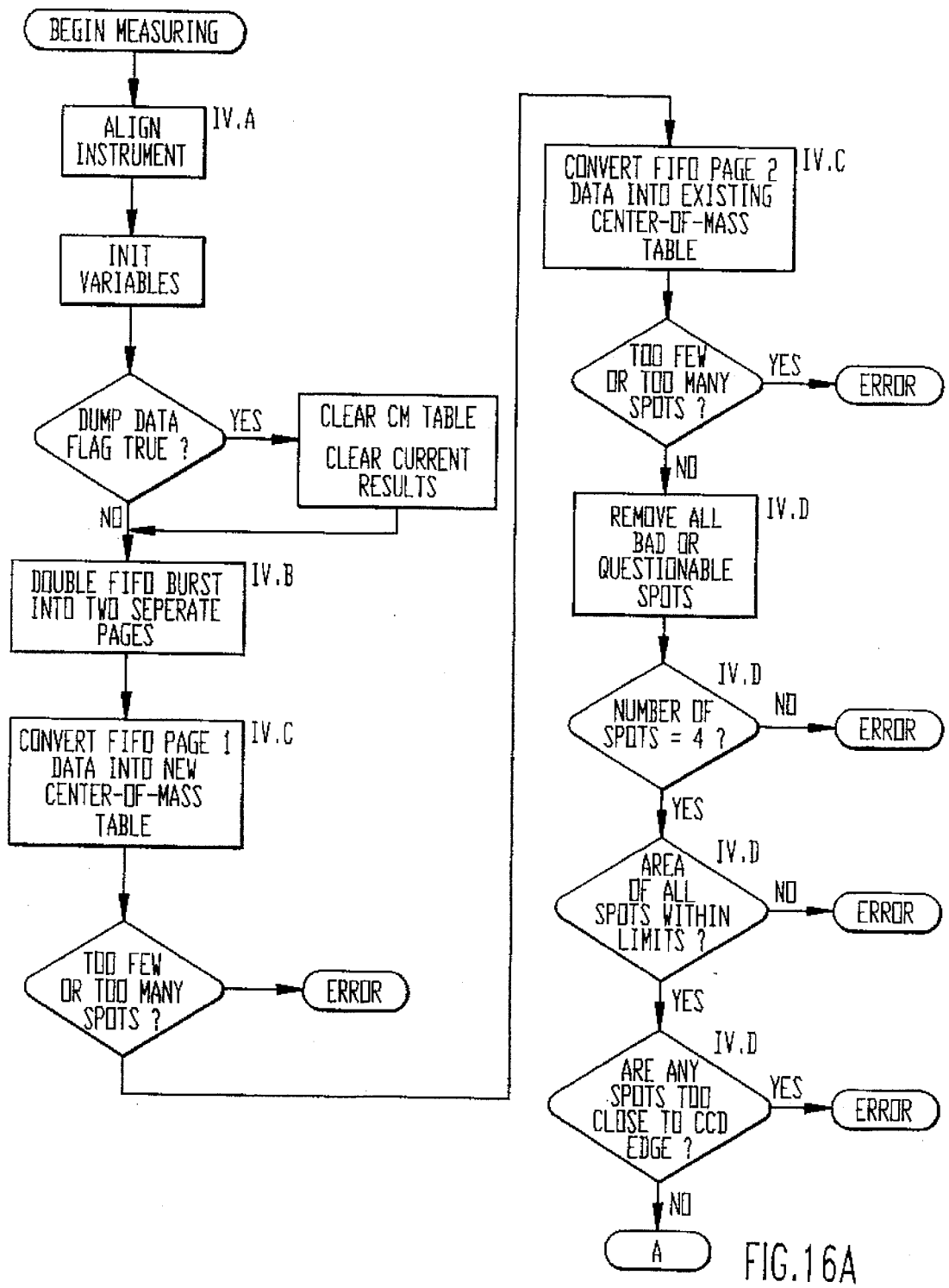
Figure 16B:
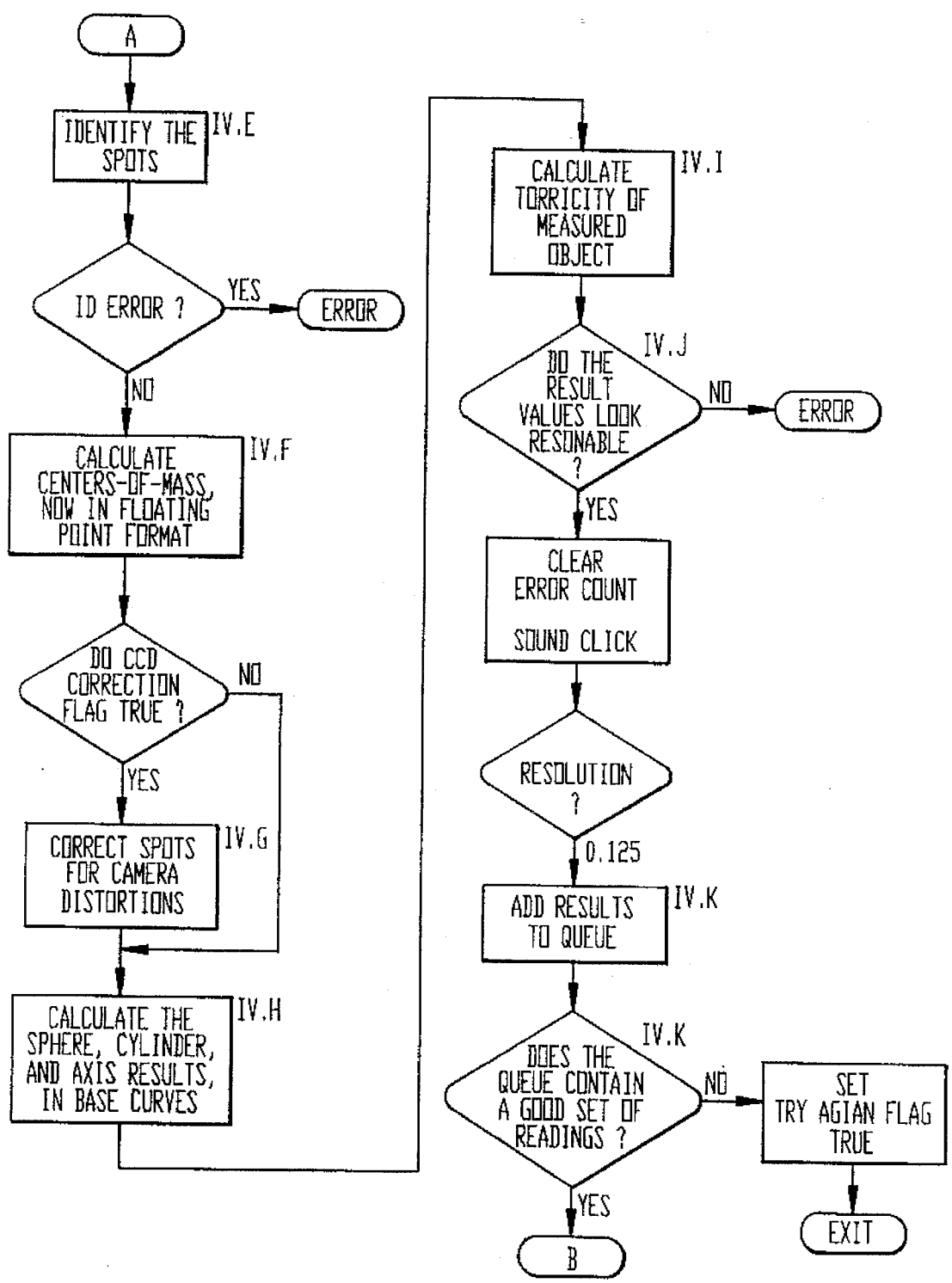
Figure 16C:
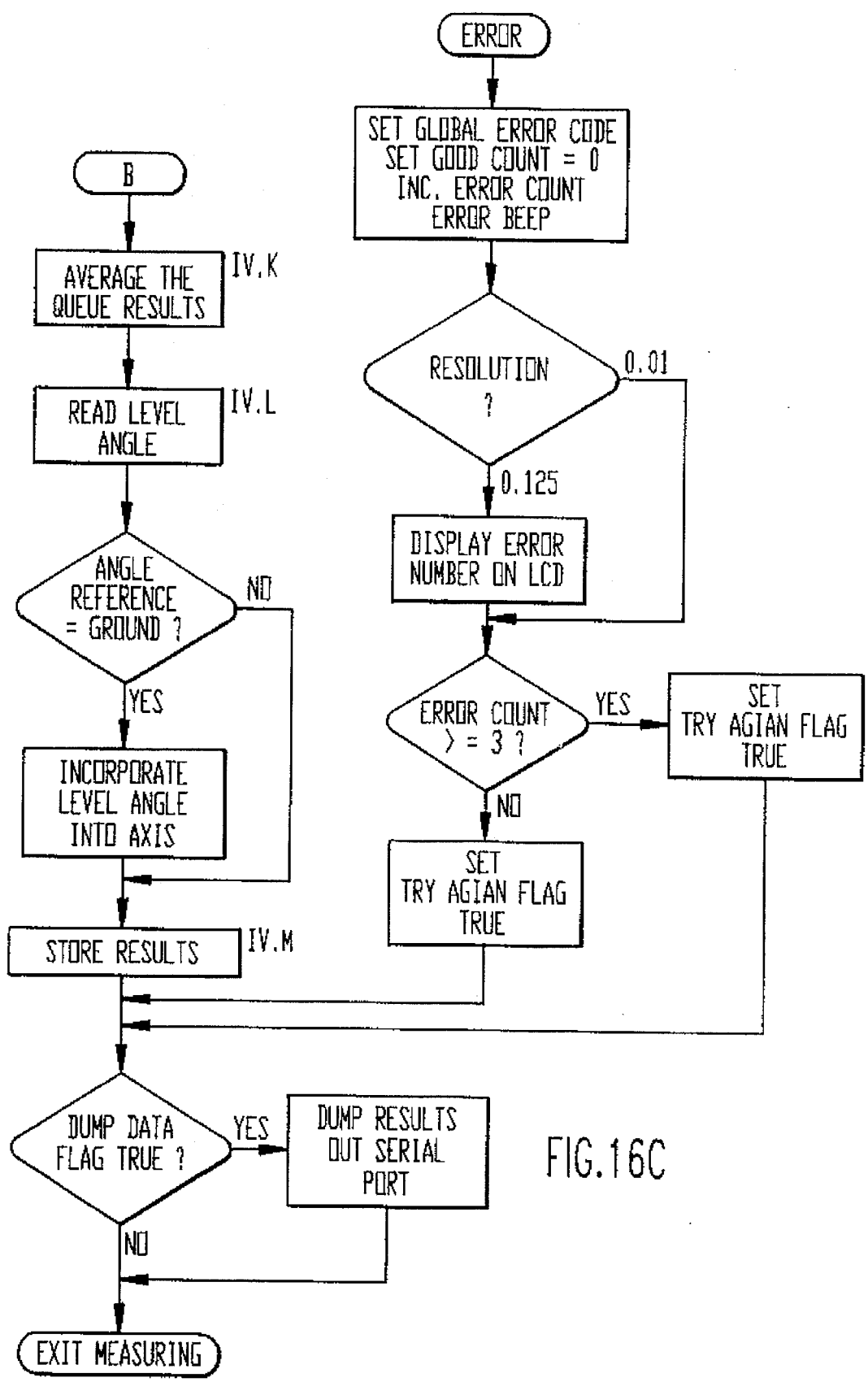
Figure 18:
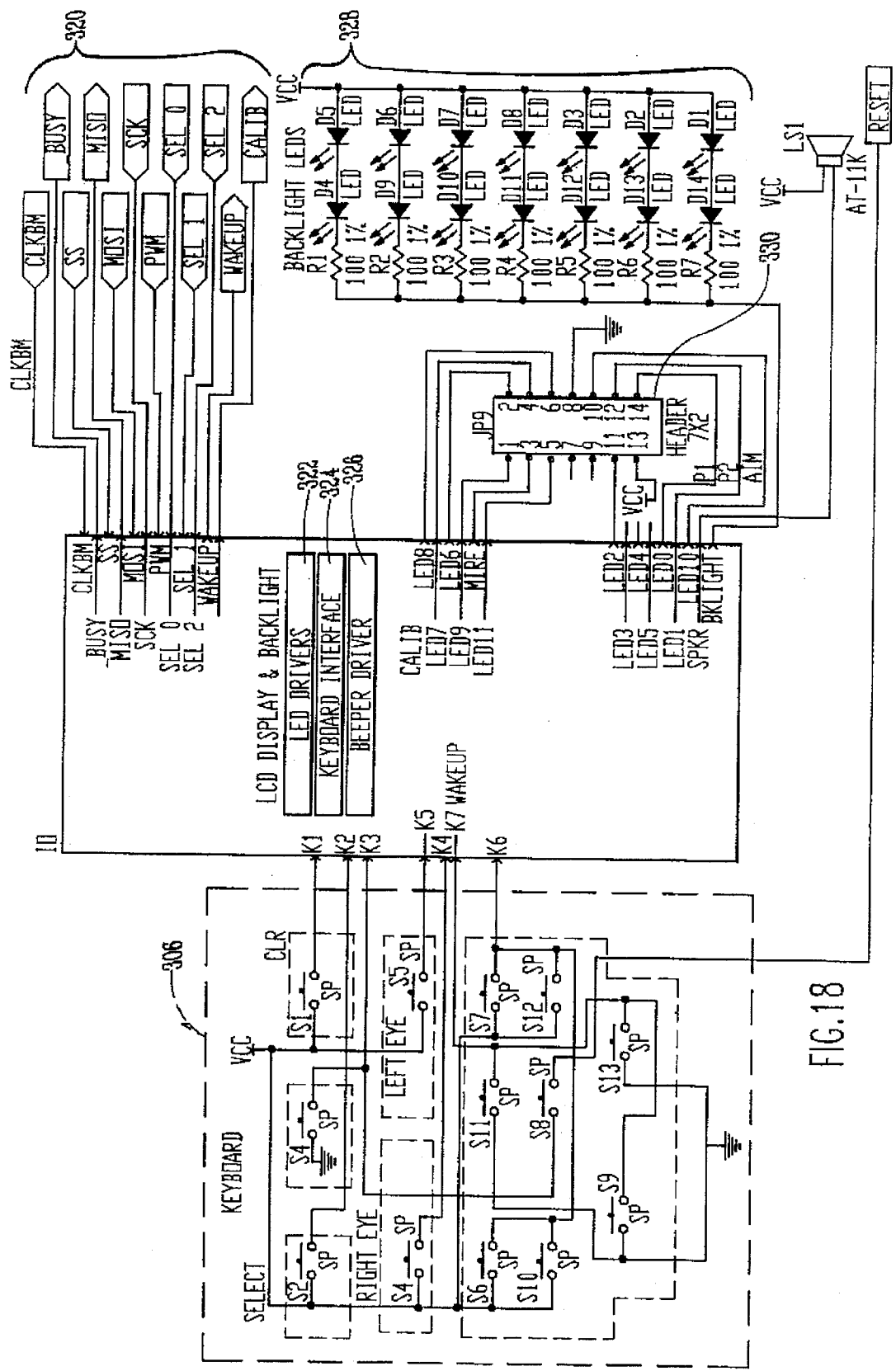
Figure 19A:
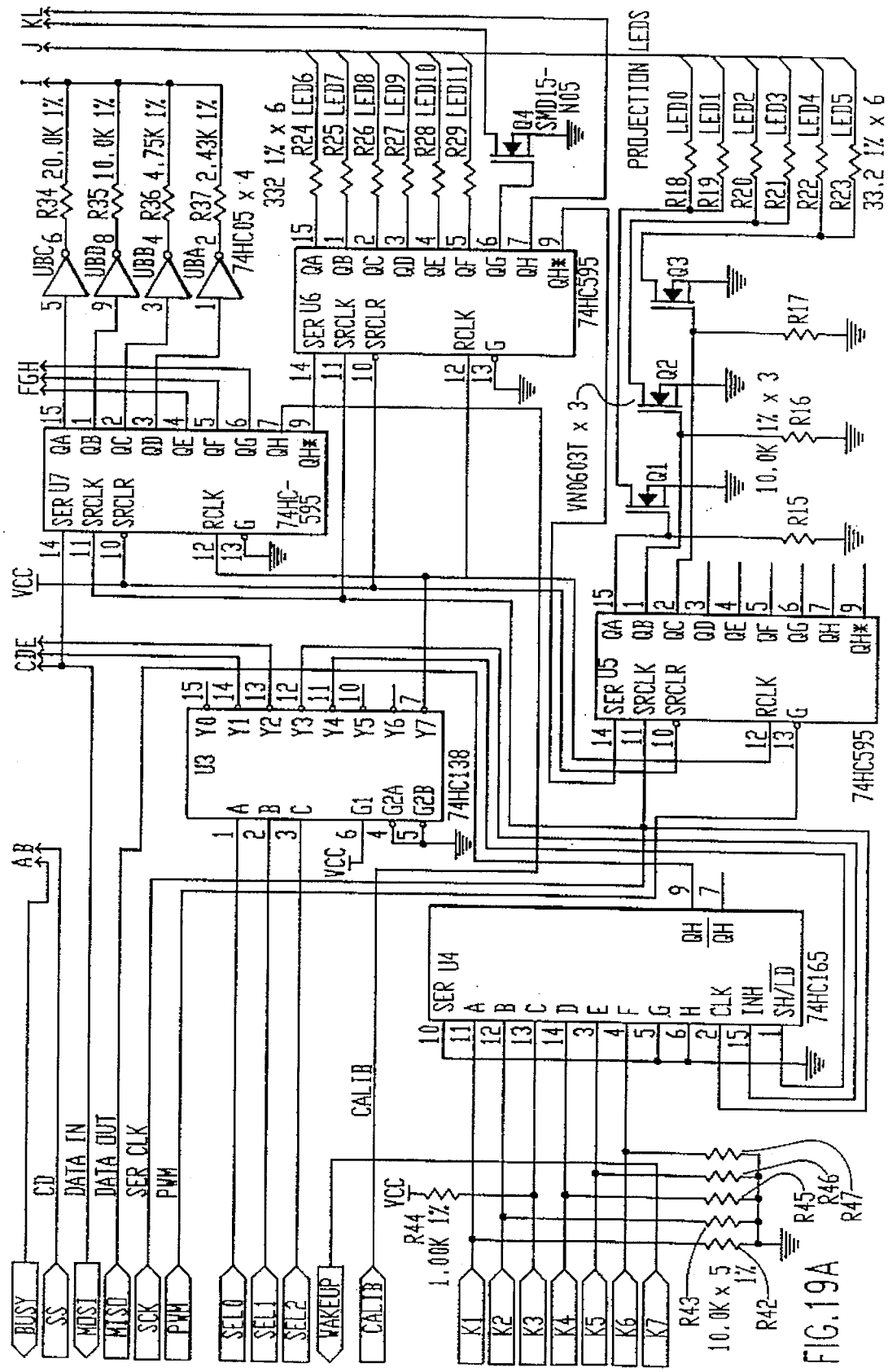
Figure 19B:
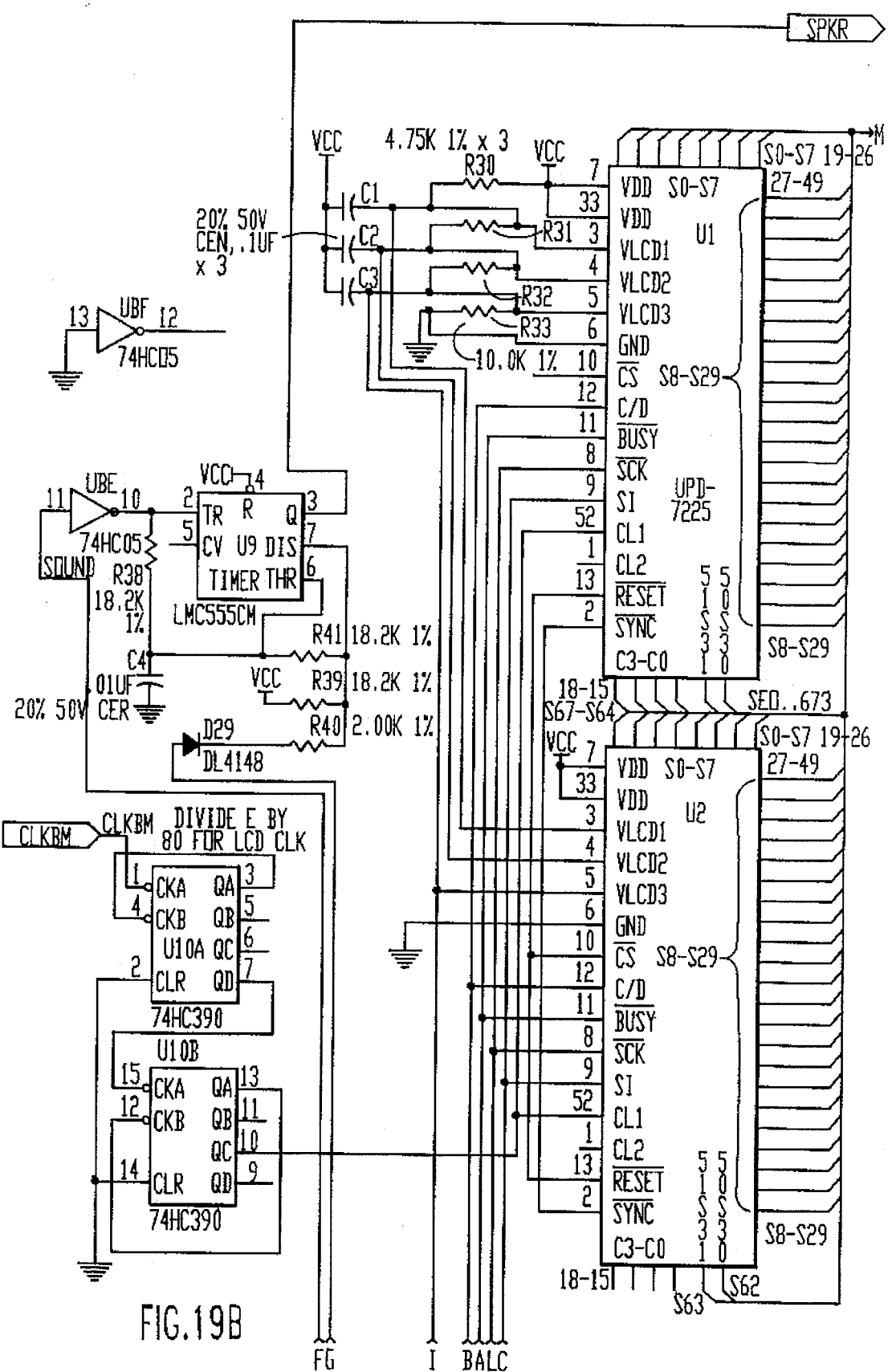
Figure 19C:
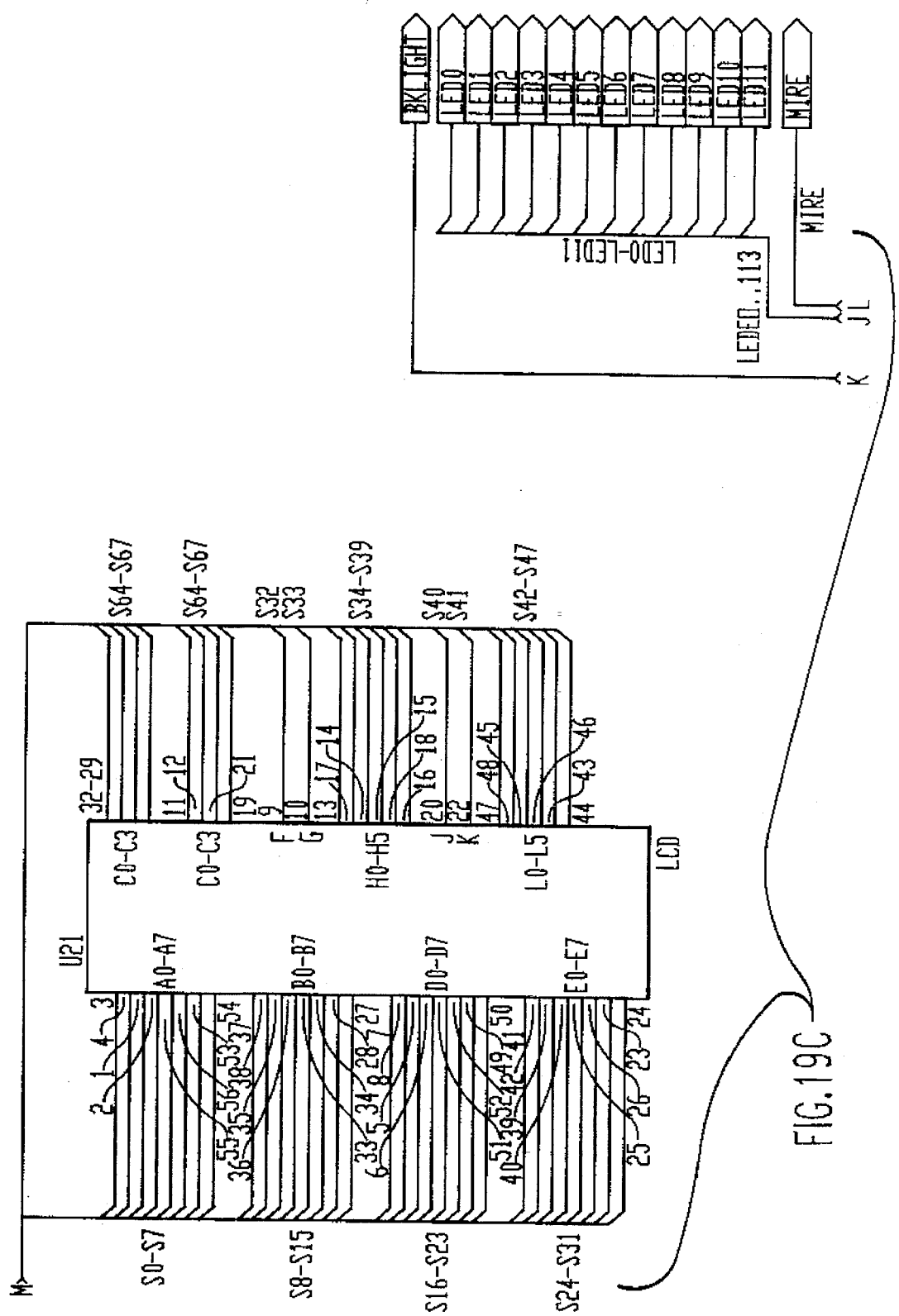
Figure 20:
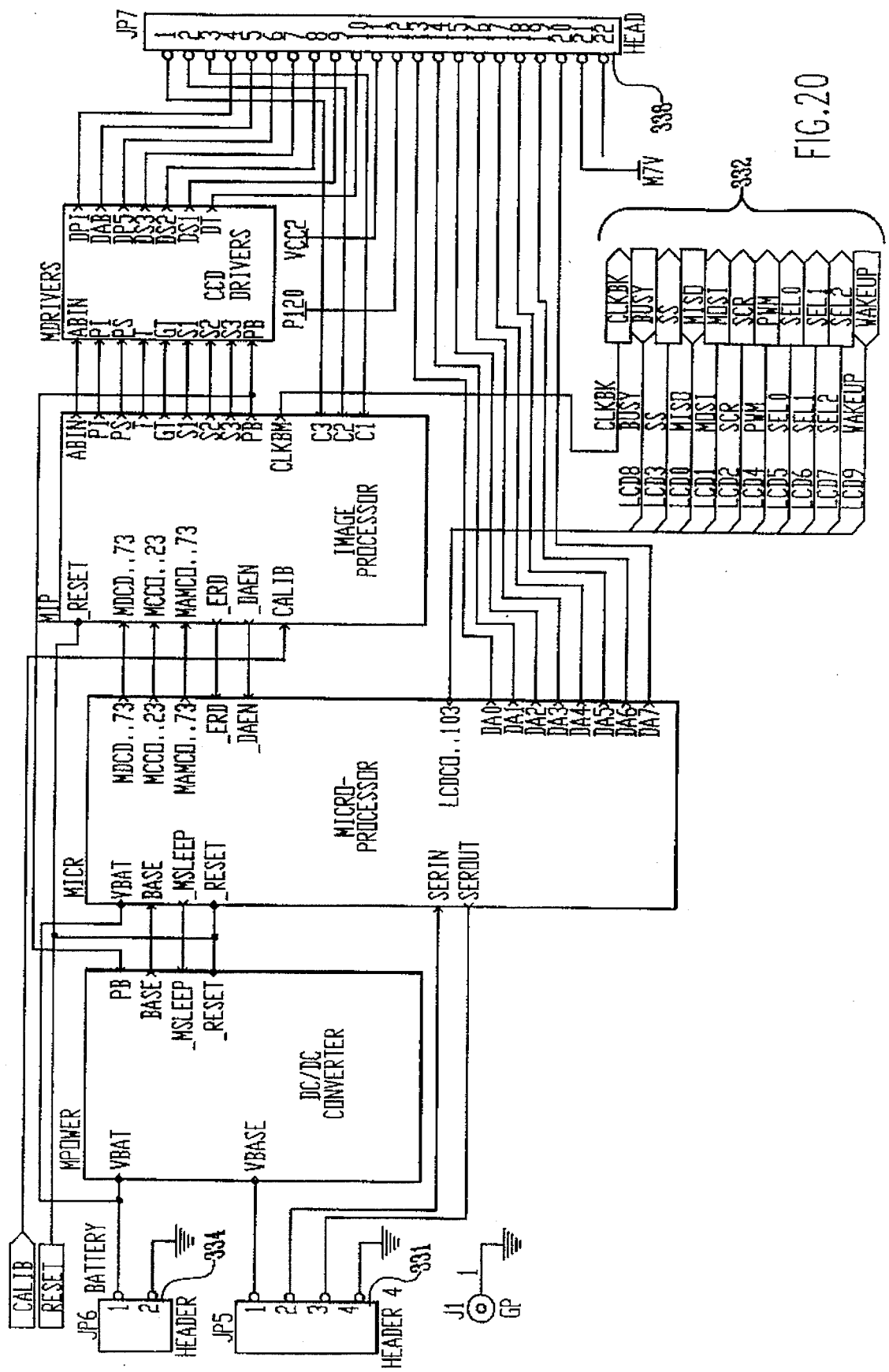
Figure 21:
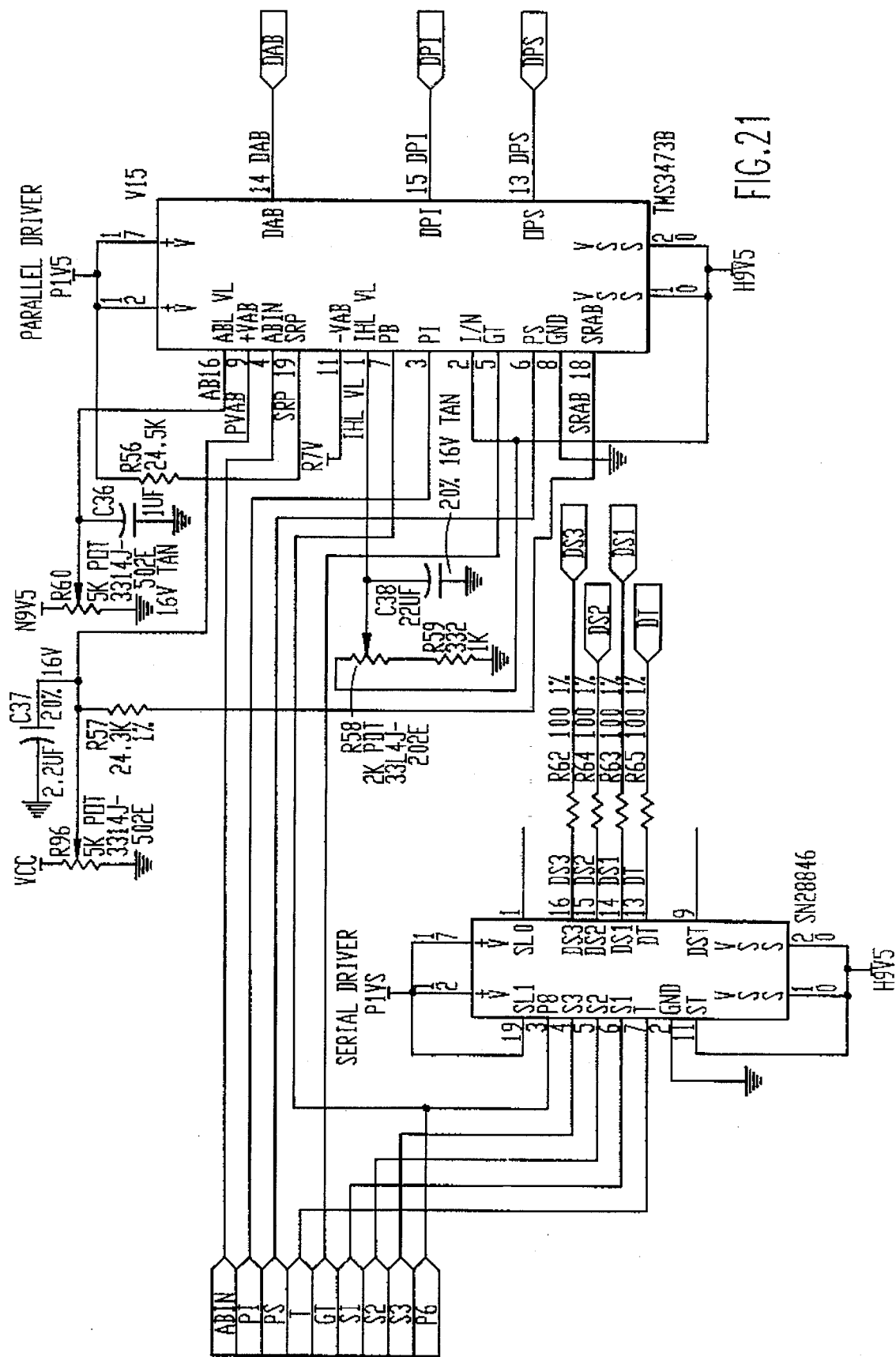
Figure 22:
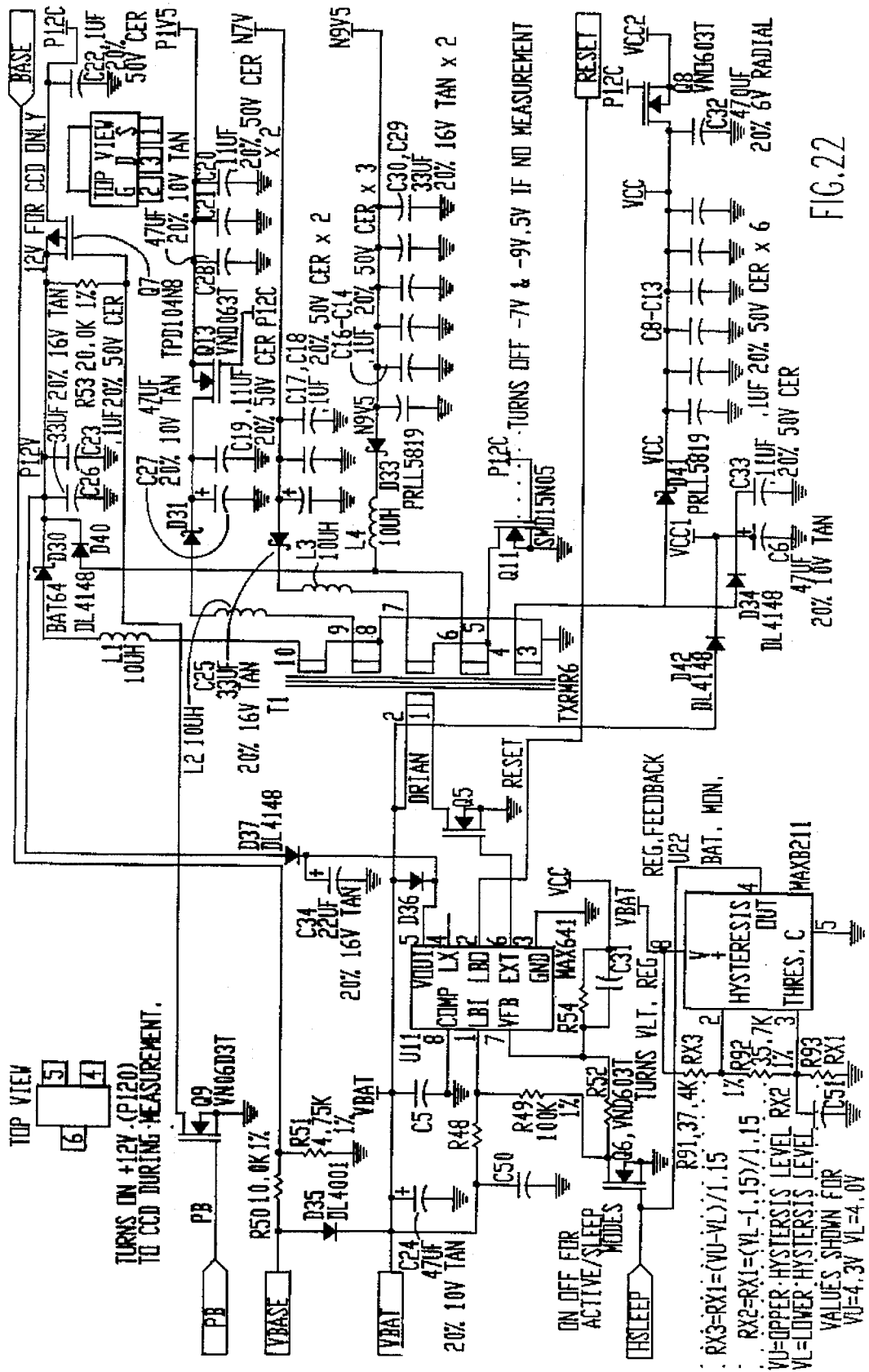
Figure 23:
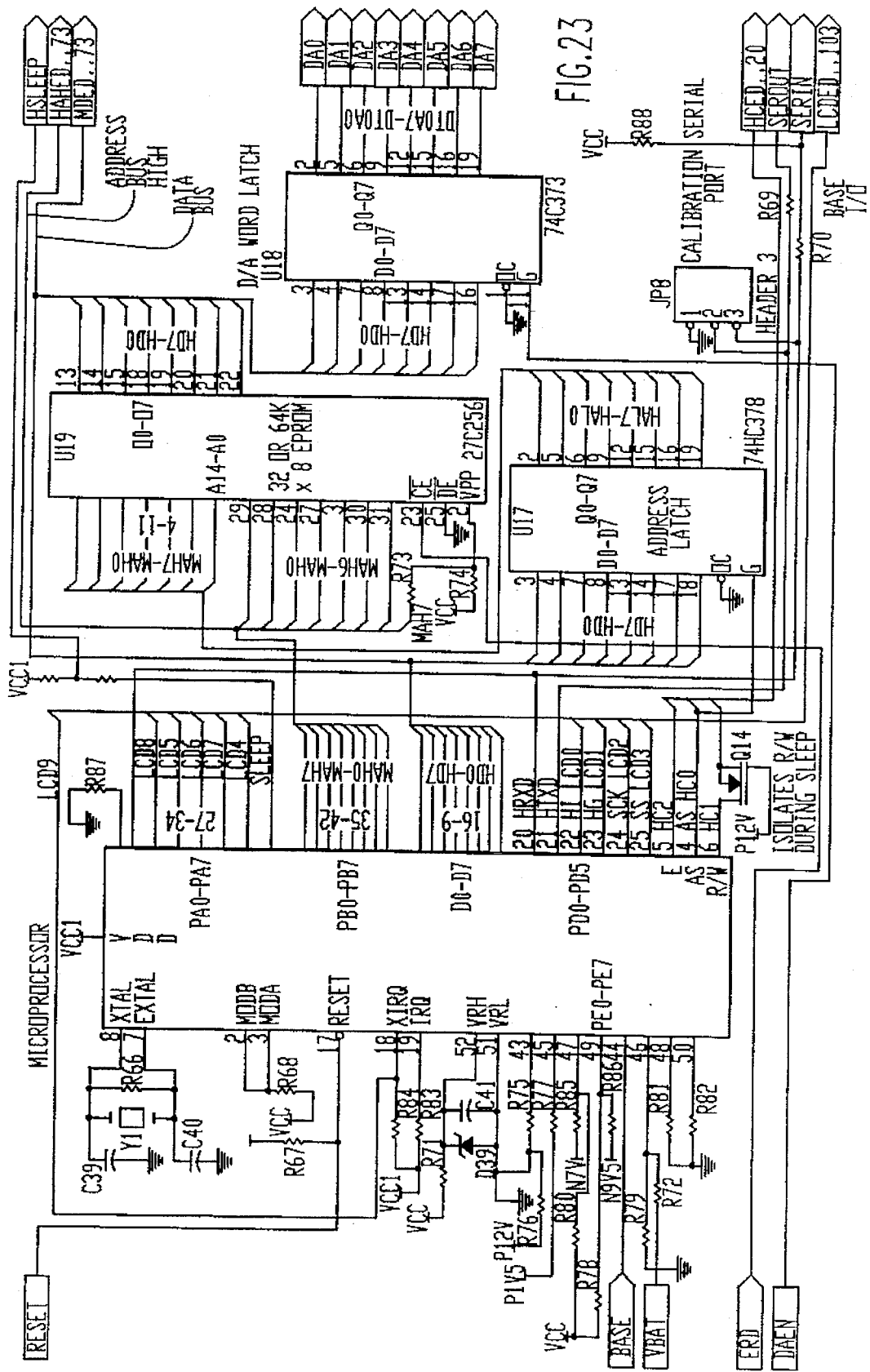
Figure 24:
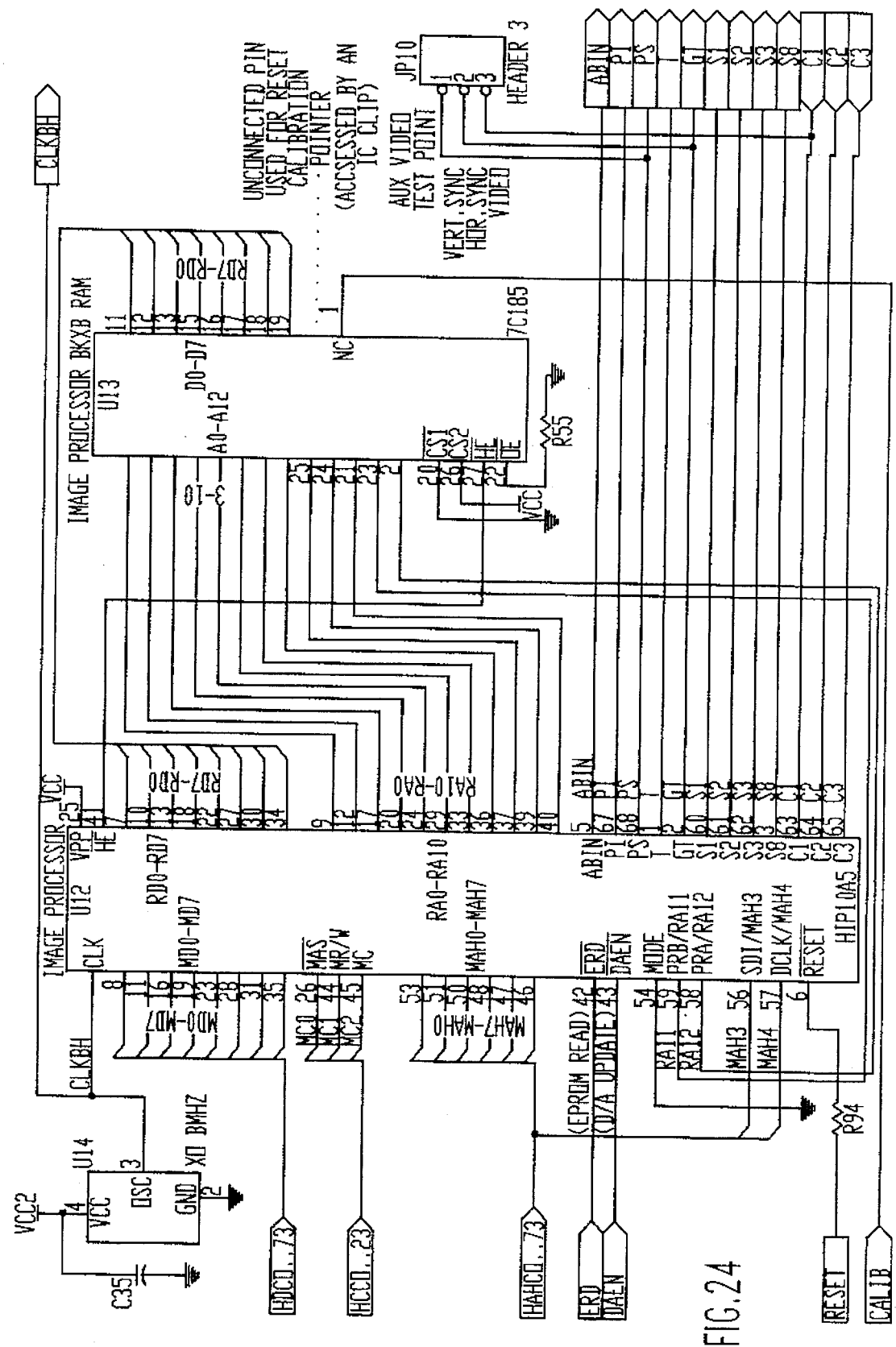
Figure 25:
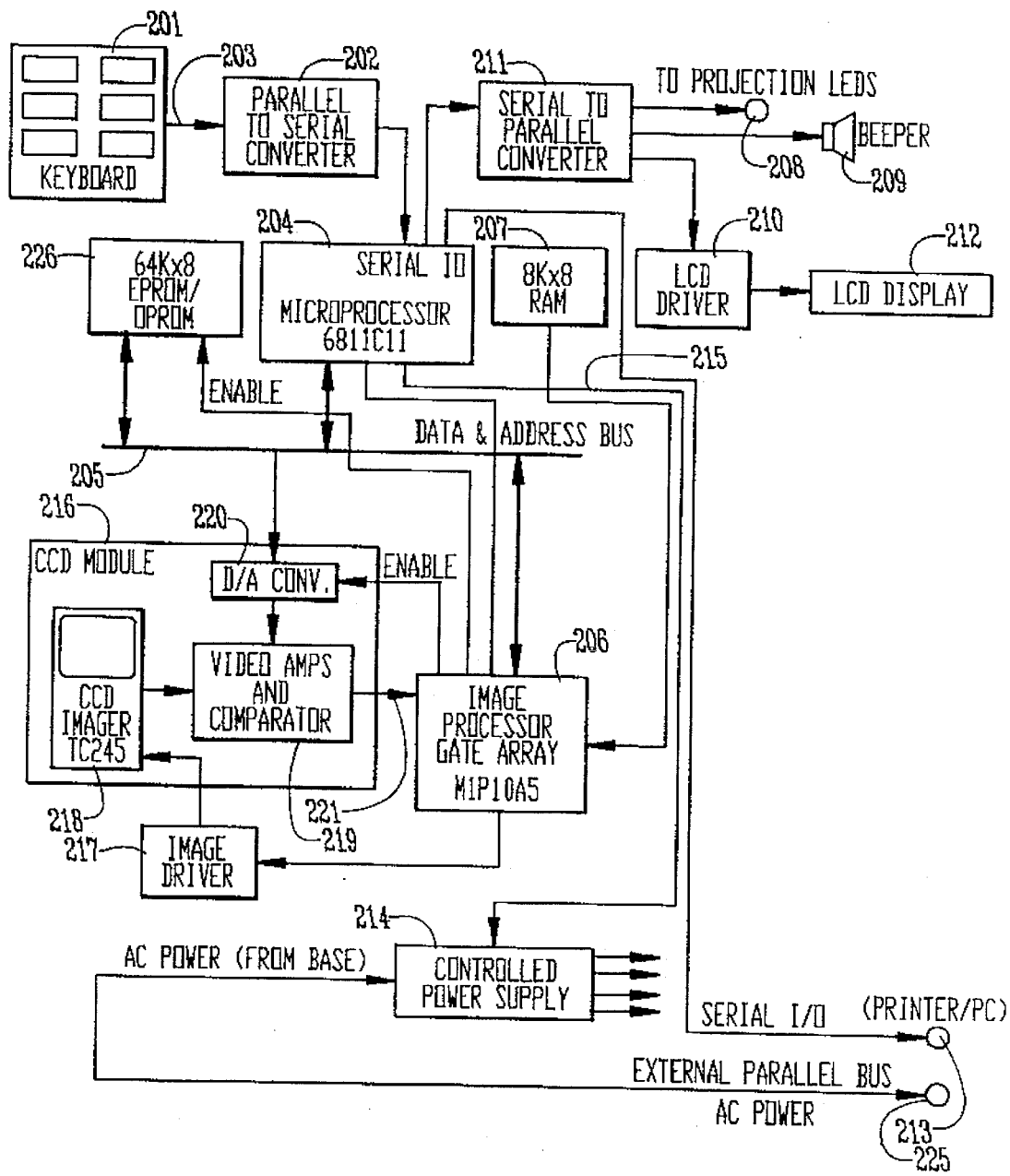
Figure 26:
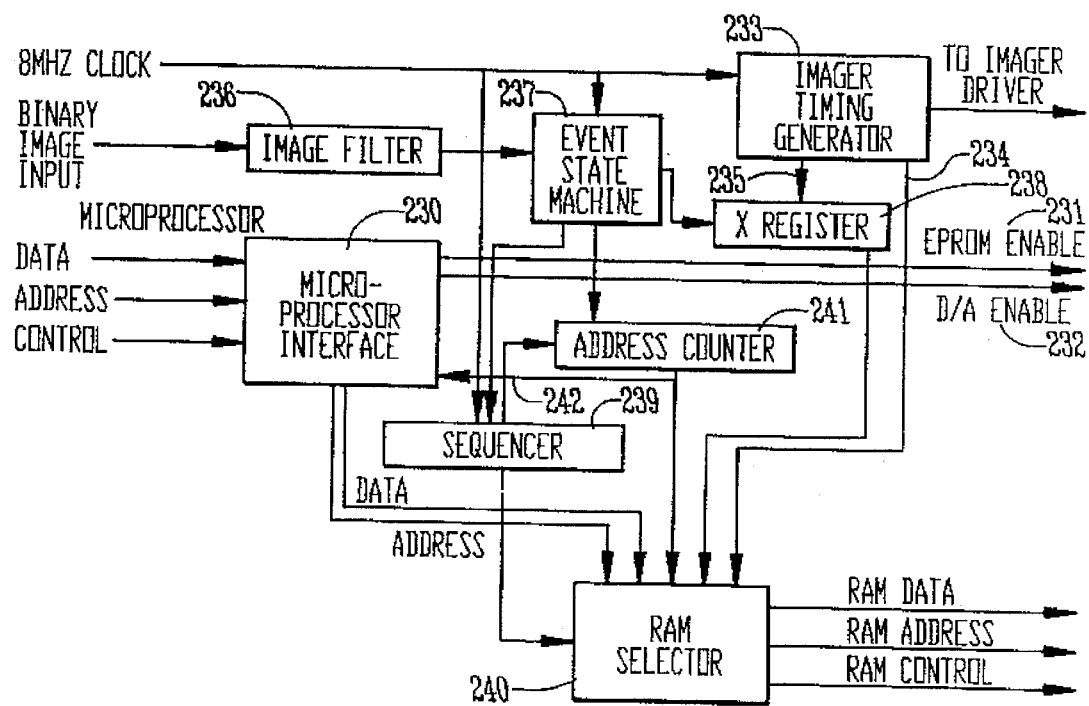
Figure 27:
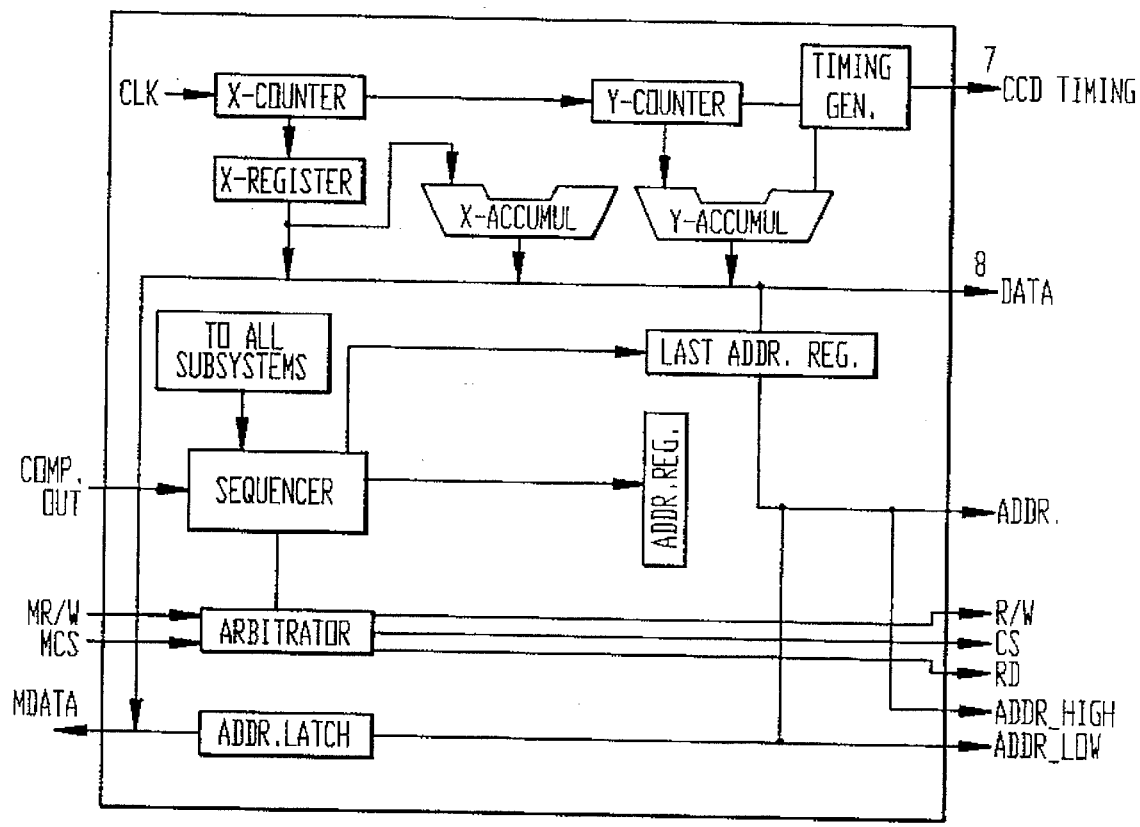
Figure 28:
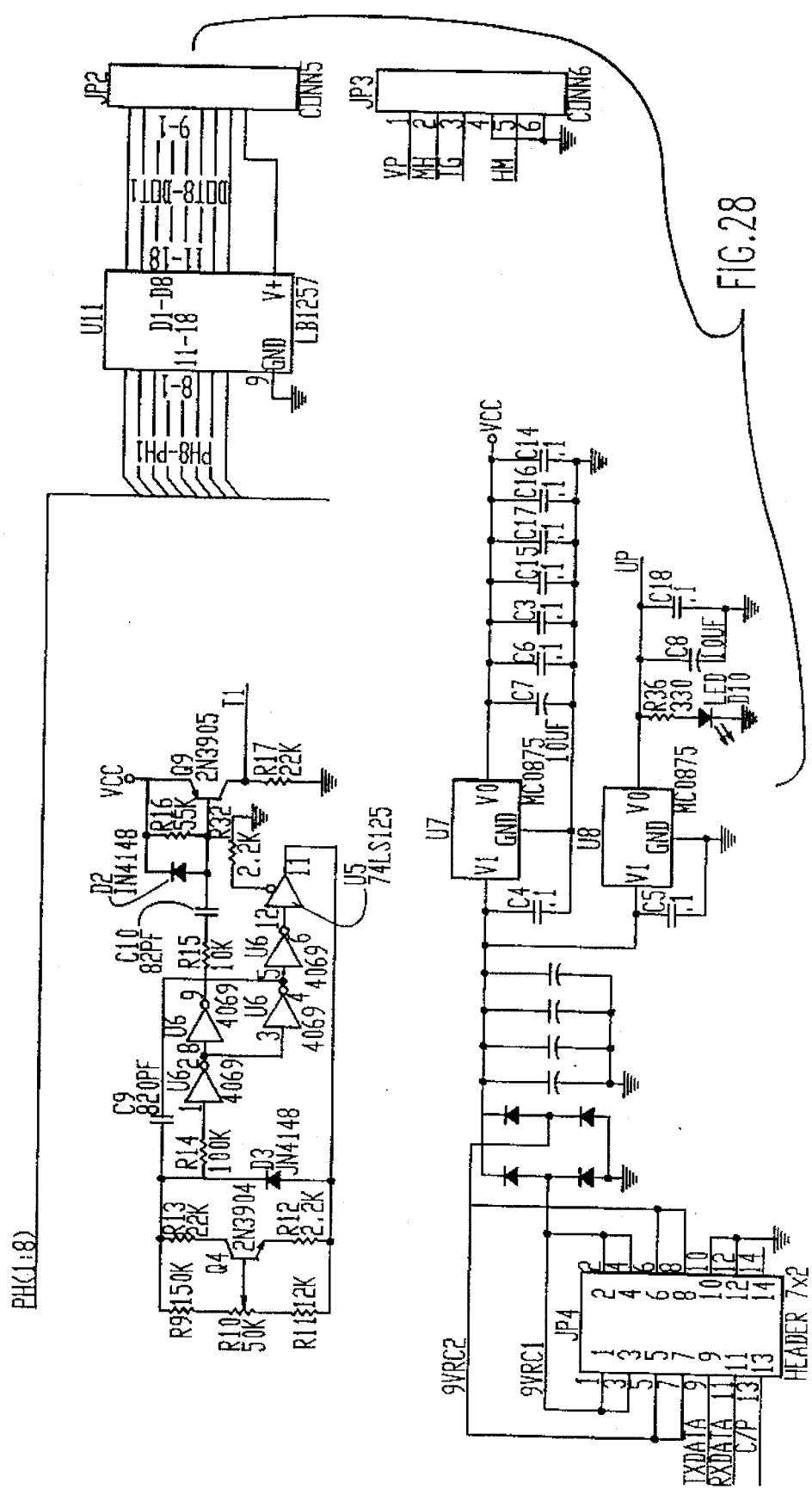
Figure 29:
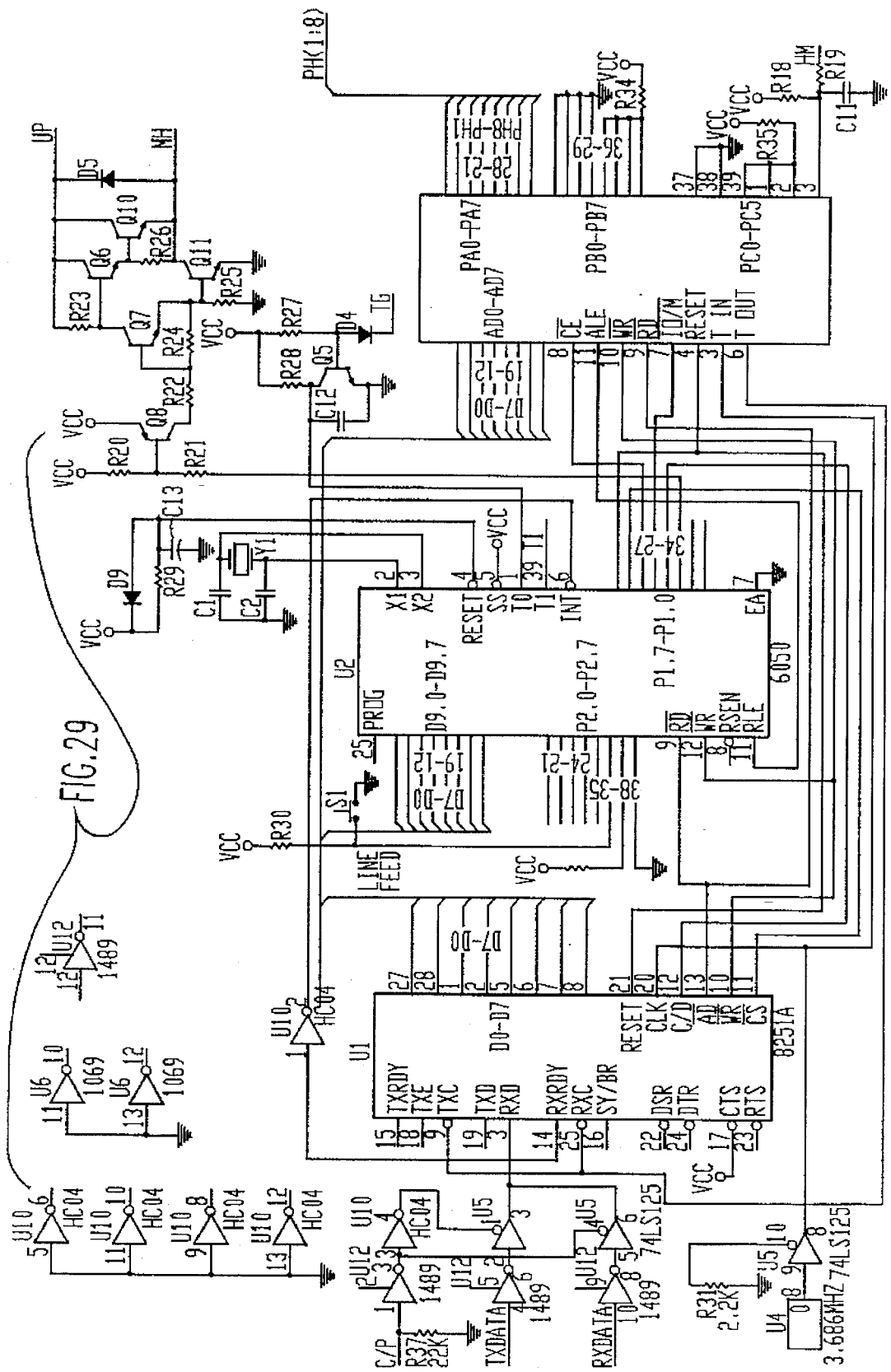
Figure 30:
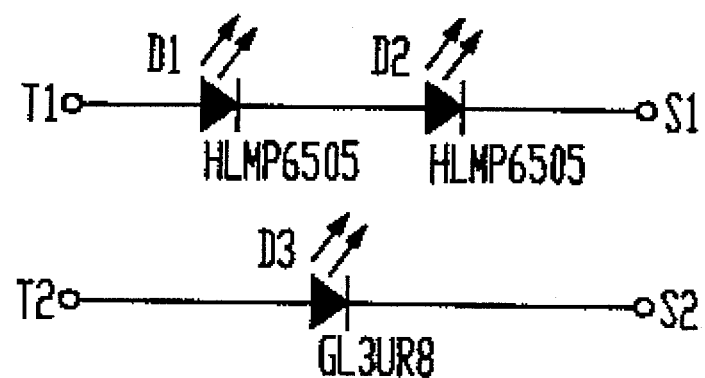
Figure 31:
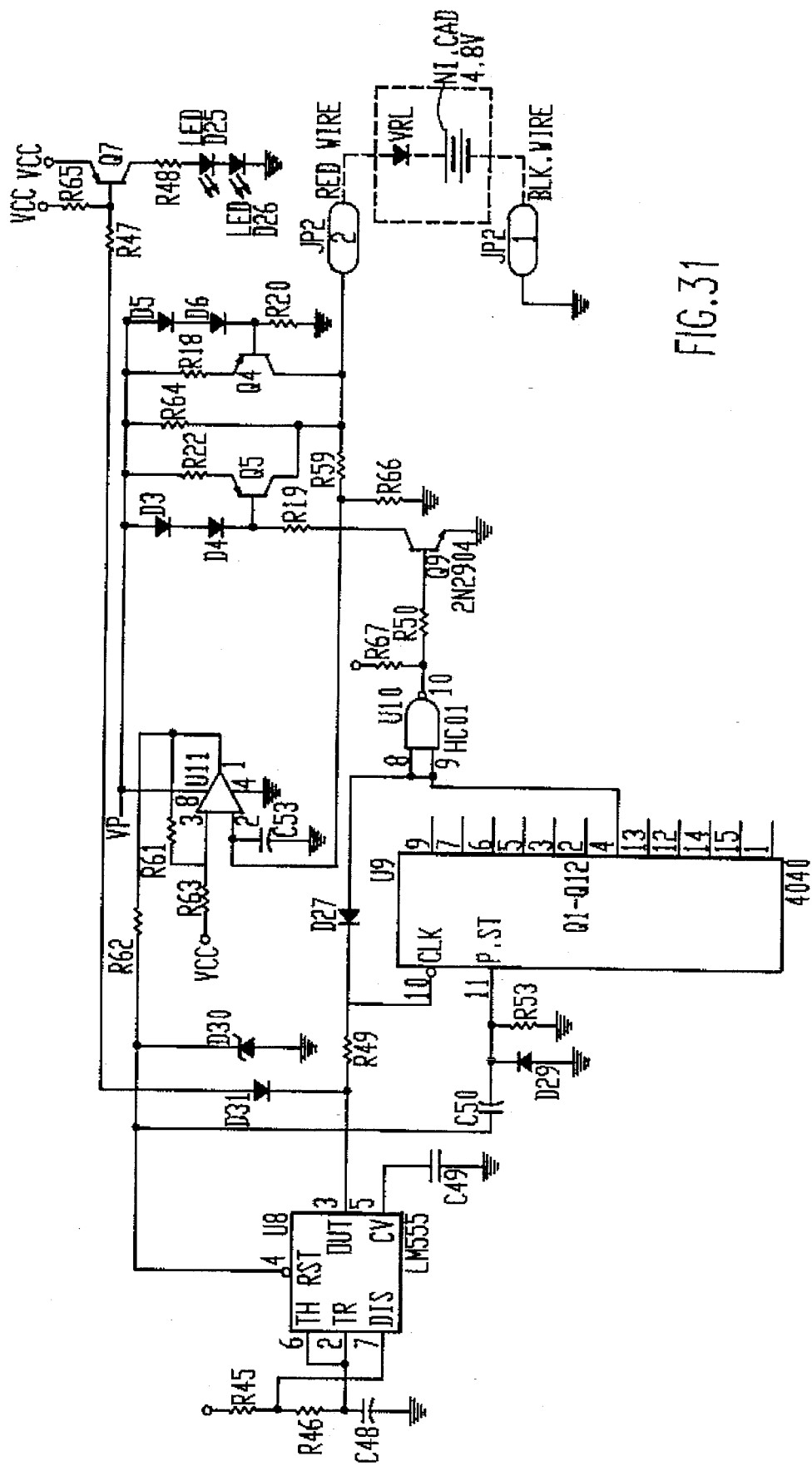
Figure 32:
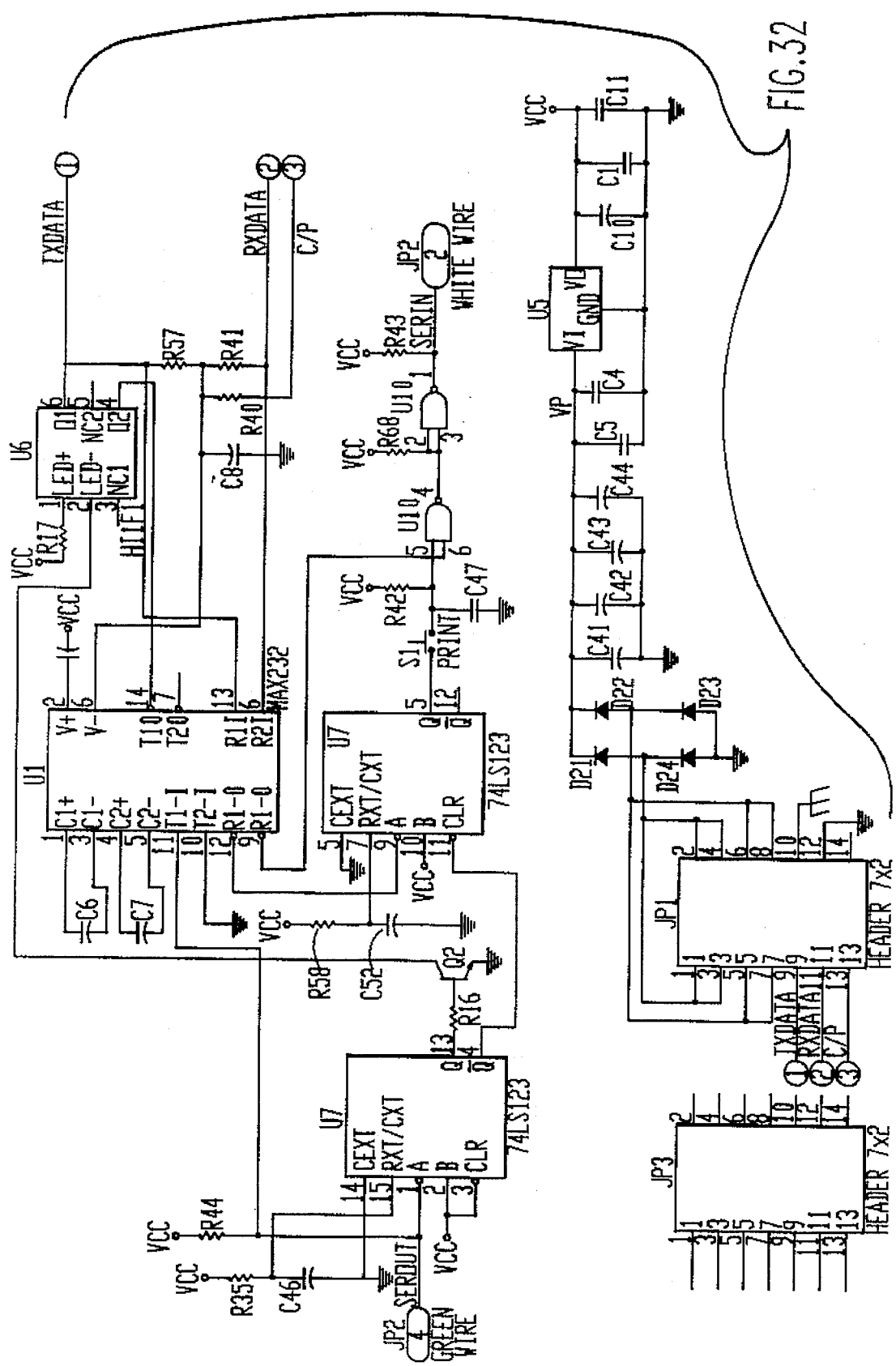
Figure 33:
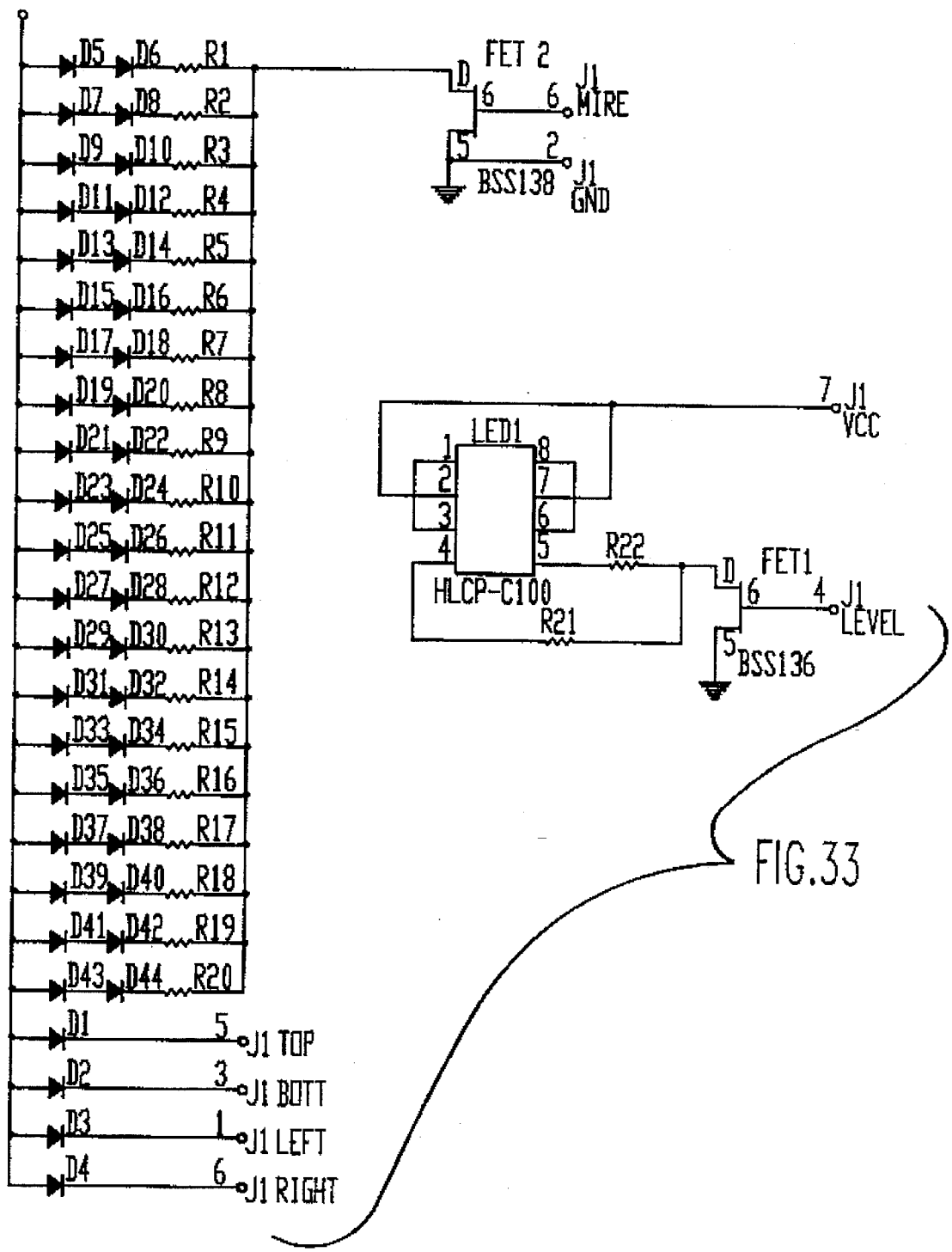
Figure 35:
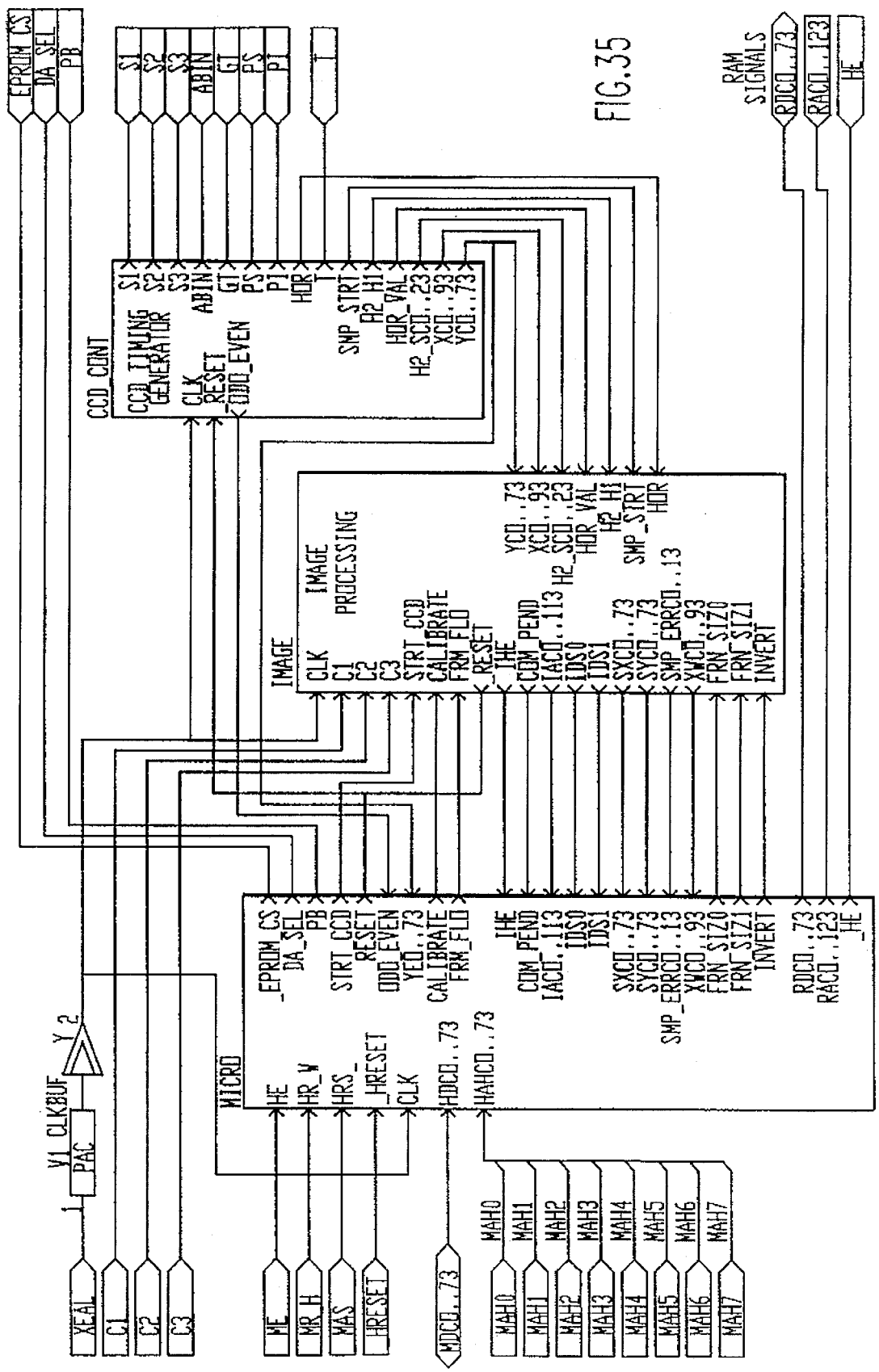
Figure 36:
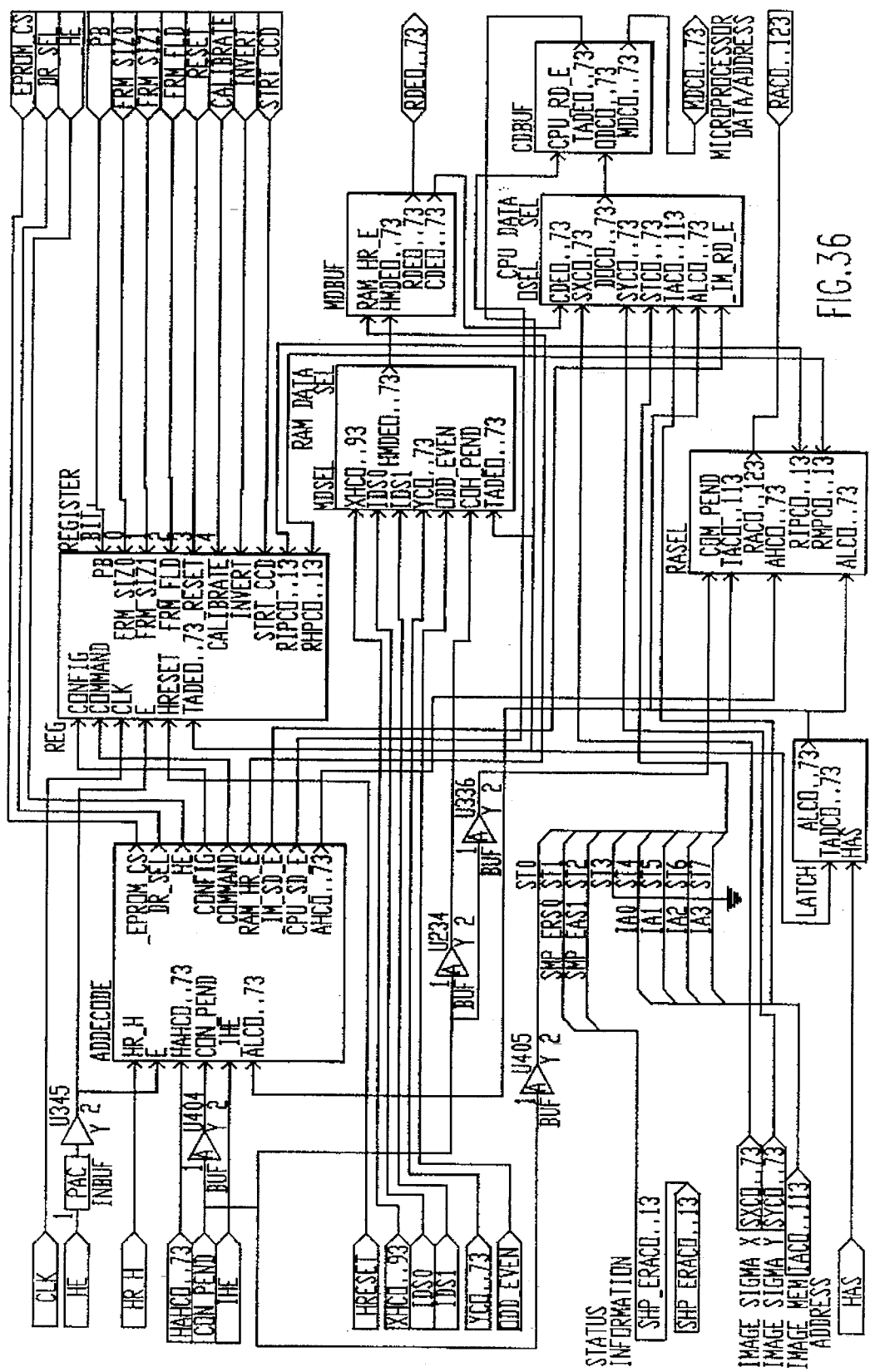
Figure 37:
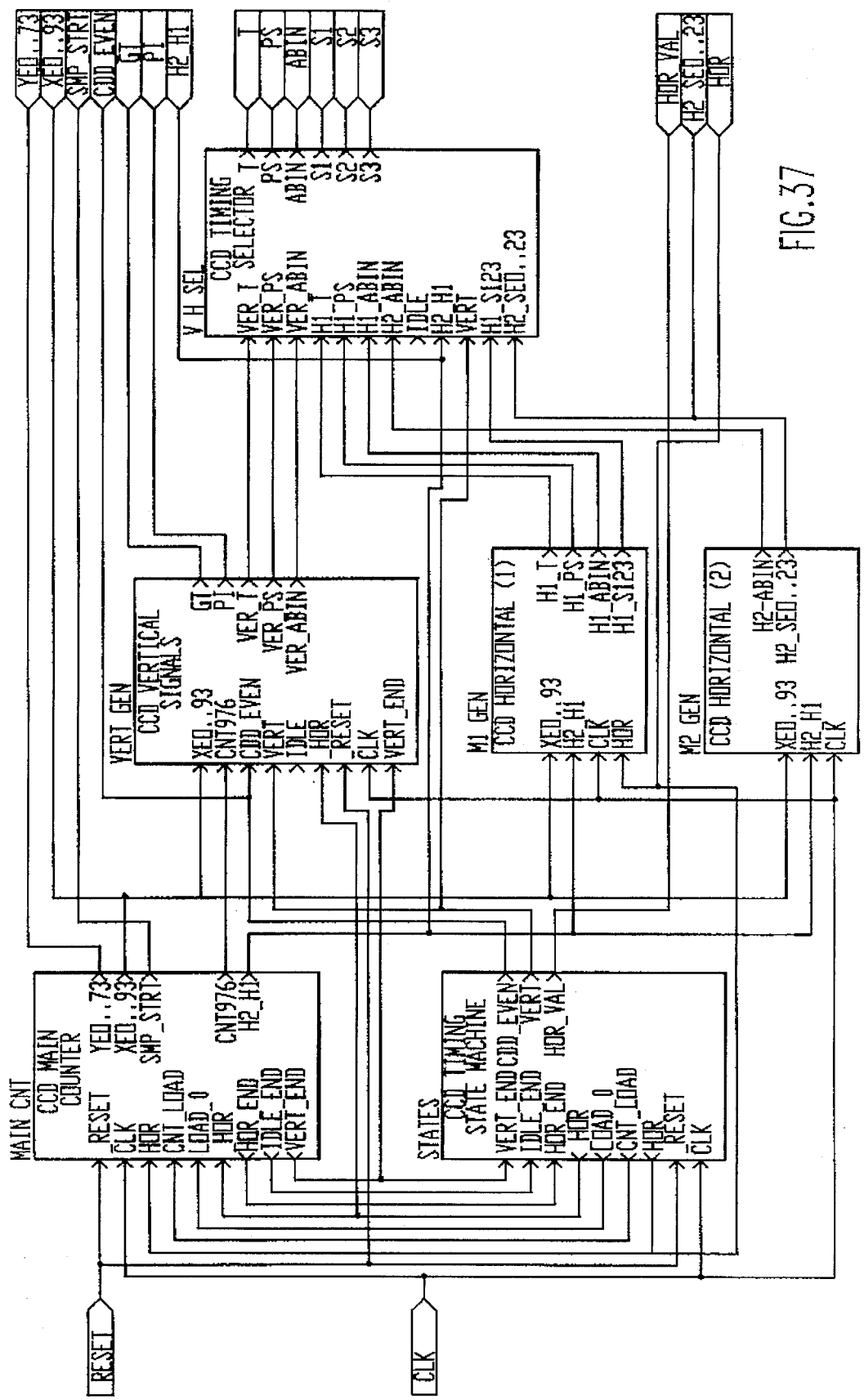
Figure 38:
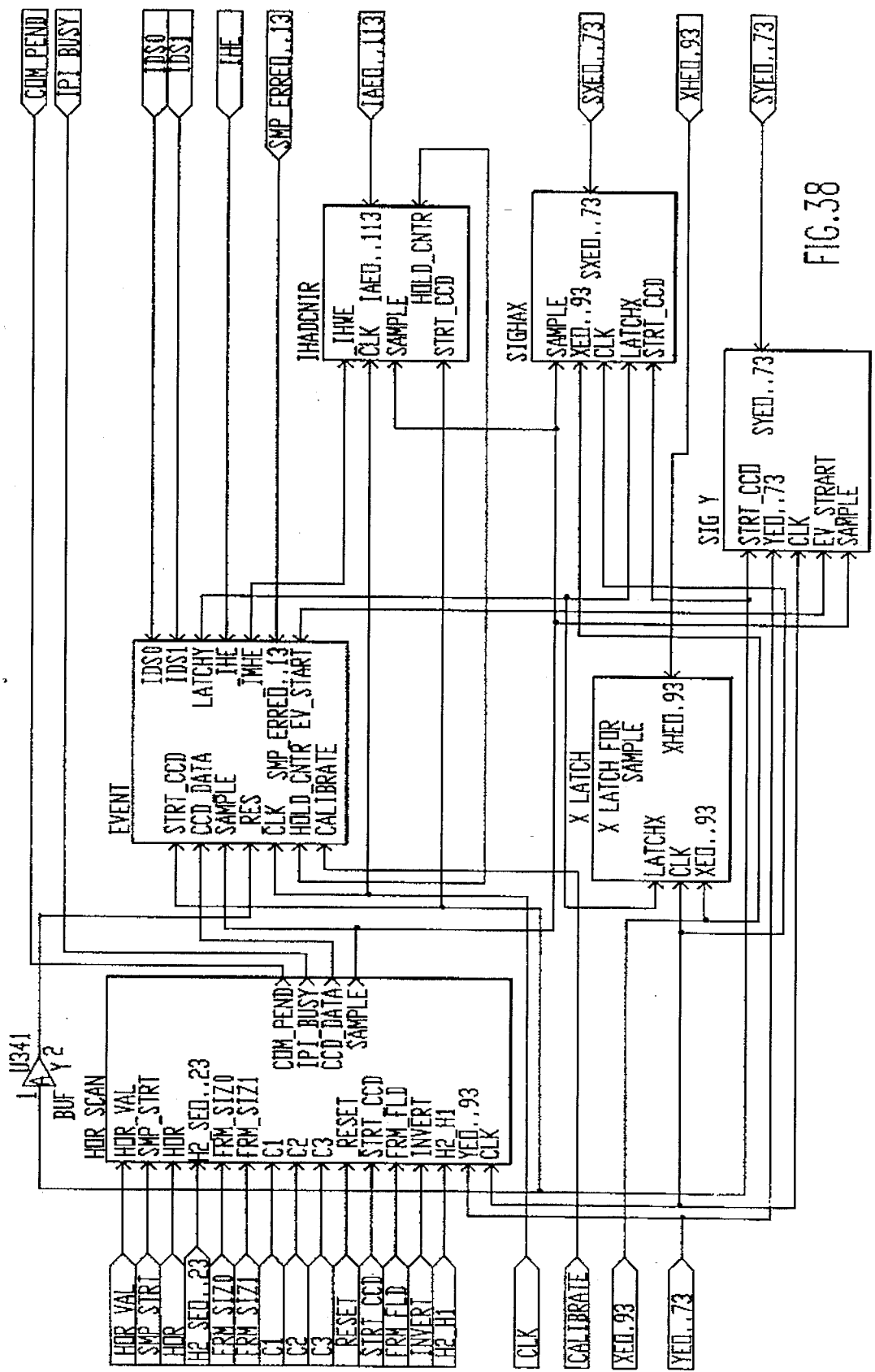

FIGS. 13A–D are diagrammatical depictions of an eye and keratometric measurements generally taken with a keratometer. FIGS. 13A and 13B depict radii of curvature measures centered on the cornea. FIGS. 13C and 13D depict the same but centered off the cornea;

FIGS. 14A–G are diagrammatical representations of various status conditions during operation of the keratometer as viewed through the eye piece of the preferred embodiment of the keratometer;

FIG. 15 is a diagrammatic representations of FIG. 14G as captured by a camera means according to the preferred embodiment of the present invention;

FIGS. 16A–16C are diagrammatic depictions of a flow chart of software operation of the preferred embodiment of the present invention;

FIG. 17 is the general block diagram of the electrical circuitry of the preferred embodiment of the present invention;

FIG. 18 is a more detailed partial schematic partial block diagram of the input/output section of FIG. 17;

FIG. 19 is a detailed electrical schematic of the input/output section of FIG. 18;

FIG. 20 is a partial schematic, partial block diagram of the main board of FIG. 17;

FIG. 21 is a detailed electrical schematic of the CCD driver section of FIG. 20;

FIG. 22 is a detailed electrical schematic of the power supply circuit of the preferred embodiment of the present invention;

FIG. 23 is a detailed electrical schematic of the microprocessor of FIG. 20;

FIG. 24 is a detailed electrical schematic of the image processor of FIG. 20;

FIG. 25 is a block diagram of the overall circuit for the preferred embodiment of the invention;

FIG. 26 is a block diagram of the image processor gate array of FIG. 25;

FIG. 27 is an internal block diagram for the gate array;

FIGS. 28–29 are electrical schematics for a printer driver that can be used with the preferred embodiment of the invention;

FIG. 30 is an electrical schematic of a projector printed circuit board that can be used with the preferred embodiment of the invention;

FIGS. 31–32 are electrical schematics for circuitry that can be used with the base of the preferred embodiment of the invention;

FIG. 33 is an electrical schematic of a Mire ring printed circuit board that can be used with the preferred embodiment of the invention;

FIGS. 34A–34B are diagrammatical charts of the different main function states for the software of the preferred embodiment of the invention; and FIGS. 35–38 are electrical schematics of the circuitry associated with image processing for the preferred embodiment of the invention.

IV. DETAILED DESCRIPTION OF THE PREFERRED EMBODIMENT

One preferred embodiment of the invention will now be described to assist in providing a more complete understanding of the invention. The description of this embodiment will be in detail including various features and advantages which may accompany this embodiment. The invention is capable of taking on many different forms and embodiments. This is but one of those forms, and is the preferred form.

This description will first give a broad overview of the embodiment and its structure. A more specific discussion of the structure will then follow. A description of the optical system of the embodiment will be set forth including examples of its operation. Finally, discussion of the electronic circuitry involved in the embodiment will be set forth referring to block diagrams and schematics.

This description is made in conjunction with the drawings. Reference numerals are sometimes utilized in the drawings to indicate specific parts and locations in the drawings. The same reference numerals will indicate the same parts or locations throughout all of the drawings, unless otherwise noted.

A. Overview

FIG. 1

FIG. 1 depicts in perspective keratometer 10 according to the present invention. Keratometer 10 includes a hand grip 12 at one end, and a projection portion 14 at the other end. An intermediate portion 16 exists between hand grip 12 and projection portion 14.

FIG. 1 illustrates keratometer 10 mounted in a base 18. Base 18 serves as a support stand for keratometer 10, and can also provide a connection to recharging circuitry to recharge the batteries which power keratometer 10. Further, as diagrammatically depicted in FIG. 1, base 18 can include connection means to auxiliary devices such as printer 20 or computer 22.

Hand grip 12, projection portion 14, and intermediate portion 16 comprise a housing 24 for keratometer 10. Dimensions of housing 24, for the preferred embodiment, are generally about 10–12 inches long, 3½ inches at its widest point, and about 3½ inches deep. It weighs only about 24 ounces. By gripping hand grip 12 (5 inches tall by 1¹⁄₁₆ inches width and depth) and removing keratometer 10 from base 18, the keratometer 10 can be easily manipulated and moved with the operator. It also can be oriented easily in a number of different ways. This ability differs drastically from state of the art and is extremely advantageous.

Base 18, therefore, is only several inches long and wide. It takes up a very small "footprint" on a table or a cabinet top in comparison to present automated keratometers. It provides a secure and stable resting or storage place for keratometer 10, and allows the user to easily and quickly grab keratometer 10 and move it where the patient is, instead of requiring the patient to come to the machine and be manipulated into position.

Printer 20 allows readings obtained by keratometer 10 to be printed in hard copy. Printer could optionally be incorporated into base 18. The readings can then be preserved, for example, by immediately placing them in a patient's file. Computer 22 can be utilized to store measurements obtained by keratometer 10, or to program the operation of keratometer 10. Buttons 26 and 28 on the top face of base 18 can be utilized to control various operations as desired.

FIG. 1 also shows the basic structure of keratometer 10. This will be described further below, hand grip 12 would enclose a substantial amount of the electrical circuitry for keratometer 10. Intermediate portion 16 includes external control buttons 30 and display 32. Display 32 is a liquid crystal display (LCD) which is a reliable yet low power display.

Intermediate portion 16 and projection portion 14 contain most of the optical components for keratometer 10. FIG. 1 shows eye piece 34 which allows the user to view directly through projection portion 14 and out a projection window 36 on the opposite side. The user or operator of keratometer 10 would then hold housing 24 so that the projection window 36 is in front of and within a few inches of a patient's eye, while the users' eye is moved directly up to eye piece 34. This arrangement is easily facilitated by the shape and configuration of housing 24, including hand grip 12. The user's thumb can easily push any of the control buttons 30 or fingers on the other hand of the user can also do the same. The user does not have to move very much to check the display window 32.

FIG. 2

FIG. 2 shows keratometer 10 and base 18 from a different angle in a slightly enlarged form. A socket 38 exists in base 18 to receive end 40 of hand grip 12. A mating connection 42 inside base 18 allows electrical communication between keratometer 10 and base 18 to in turn facilitate connection to recharger, printer 20, or computer 22.

A spine 44 extends from the rear of base 18 vertically upwardly. An extension 46 consisting of a bent rod extends from spine 44 outwardly and upwardly to a top end 48. A notch 50 in the underside of projection portion 14 of keratometer 10 is configured to matingly settle on top end 48 when keratometer 10 is placed on base 18 as shown in FIG. 2. This securely and stably holds keratometer 10 in place.

Base 18 includes a circuit board 52 (see FIGS. 30A & 30B) which can contain the interface between keratometer 10 and printer 20 or computer 22. Base 18 could contain an LED light or lights 54, if desired, to indicate recharging or printer in use, or other matters, as desired.

B. Overview of Operation

A basic simplified description of operation of keratometer 10 will now be described with reference to FIGS. 1 and 2. Keratometer 10 is used to measure at least two radii of curvature of a patient's eye. These radii of curvature are usually taken along axes which are perpendicular to one another and which intersect at or near the optical center of the eye (generally the center of the cornea). If these radii of curvature are known, the diopter power or refractive power of the eye can be calculated. Keratometer 10, therefore, basically is measuring the refractive power of the eye. It is a diagnostic tool to understand what type of correction the eye might need in the form of eye glasses or contacts or the type of fitting needed. It also may be used to discern any deformities or other problems with the eye.

The preferred embodiment of keratometer 10 allows the user to easily and quickly pick up keratometer 10, move it up to the patient's eye, align the keratometer, and take the appropriate measurements. When the readings are complete, they are stored and can be displayed on display 32. They can then be printed out to printer 20 when keratometer 10 is replaced to base 18.

In very simplistic terms, the measurements are taken as follows. The user brings keratometer 10 into position a few inches or centimeters from the patient's eye. The user then looks through eye piece 34 and can clearly see the patient's eye. The user then tries to center keratometer 10 with respect to the patient's eye by estimation but is assisted in this because eye 34 is positioned directly along an axis which becomes co-linear with an optical axis extending through eyepiece 34 and projection window 36. In other words, if a line were drawn through the center of eye piece 34 and out the center of projection window 36, the user would try to put that line directly on the middle of the cornea of the patient's eye (or some other aiming point on the eye).

Keratometer 10 includes automated methods to confirm centering of the keratometer 10, as well as to make sure that it is not too far away or too close to the patient's eye. A significant advantage of the present invention is that it does not require exact axial positioning of keratometer 10 with respect to the patient's eye but only requires that it be within a certain range of positions which can be verified by the machine.

Alignment is facilitated by projecting a pattern of collimated light sources onto the eye. The pattern is configured so that the operator, by viewing the reflection of the pattern through the eye piece can tell if keratometer 10 is within correct range from the patient's eye.

Once alignment is within an acceptable range, the actual measurements are taken generally as follows. A light is projected along the optical axes out the center of the projection window 36 onto the patient's eye.

This light serves as a fixation target for the patient to hold his/her eye steady. This fixation light is also visible by the user through eye piece 34 to assist in aligning the fixating light onto the patient's eye.

The next step is the projection of four highly collimated light sources onto the eye. These basically thin lines or beams of light converge at angles towards the optical axis and intersect the curved surface of the eye at points surrounding the fixation light along the optical axis.

Because the angles of these light beams is known with respect to the optical axis, measurement of the spacing of the light point images reflected from the cornea can be used to derive the radii of curvature and major and minor axis angles of the cornea.

Measurement of these distances is accomplished automatically. The reflection of the projected lights is received back through the projection window 36 and reflected along an optical axis to a camera which includes what is called a CCD imager. The imager is basically a matrix of picture elements (pixels) of very small size. Each pixel produces an electrical signal proportional to the intensity of light incident upon it and therefore basically replicates the reflection of the eye as it is received. The spacial positions of each pixel are known and correlated in memory and therefore distances between the reflected images of the projected lights can be derived electronically. The processor within keratometer 10 controls and calculates these measurements and converts them into readings which are displayed on display 32 and stored in memory.

Not only is keratometer 10 easy to handle, maneuver and use, it also facilitates quick and reliable accurate readings which can be preserved. The whole measurement process, including positioning of the patient, takes only a matter of seconds. It is fast enough that several readings can be taken and averaged to increase accuracy.

The structure and form of housing 24, along with its light weight, make it very ergonomic, in addition to providing the many advantages discussed. The operator can quickly and easily bring the keratometer to the patient, align it with automatic and automated assistance, verify the patient is fixated, and take the measurement automatically. This in turn makes it much easier for keratometric readings to be routinely taken by staff, which would require much less training and expertise than existing devices.

C. Detailed Structure

FIG. 3

FIG. 3 shows a still further enlarged form keratometer 10 in elevated section (and without base 18). The specific structure of the interior of housing 24 is shown. Projection window 36 is a plate glass disc (Rolyn Optics, Part #55.1258, 47.6 mm dia., 3.1 mm thick). Behind window 36 are a ring of red LEDs 56 (see also FIG. 4) around the outer circumferential edge of window 36. These LEDs are angularly oriented in converging fashion and when powered simultaneously project a ring of red light onto a patient's eye (depicted at 58 in FIG. 3). The ring of light is called a mire ring which when projected on eye 58 allows the user (see user's eye 60 in FIG. 3) to look through eye piece 34, and see the ring on eye 58 to subjectively determine if there are any abnormalities in the curvature or roundness of the eye.

Also behind window 36 are the four projectors 62 which project the thin collimated light beams onto the eye. Each projector consists of an LED 64 (Hewlett-Packard Part #HLMP-Q101, T 1¾ red tinted diffused LED) behind a pinhole card 66 (1 mm pinhole) and a compound collimating lens 68 (Edmund Scientific B32, 719 Achromat, 30 mm focal length, 15 mm dia. +/−0.1 mm). These components are held in projector tubes 70 which are each oriented at 21.5° (+/−1°) with respect to optical axis 72 as shown in FIG. 3. Projector 62 therefore projects a point source of light along axes 74 so that they intersect with optical axis 72. By referring to FIG. 4, it can be seen that each projector tube 70 is spaced an equal radial distance from optical axis 72 and at 90° from one another circumferentially around optical axis 72. As can be appreciated in FIG. 3, the patient's eye 58 must therefore be positioned in front of the point of intersection of axes 74 with optical axis 72 so that each point of light from projectors 62 will be spaced apart on the front surface of eye 58. However, it is to be understood that there is a range of positions for eye 58 along axis 72 which allow reliable readings to be taken and therefore exact positioning is not required.

The optical axis of keratometer 10 consists of portion 72a extending through eye 58 and originating inside housing 24. Portion 72b reflects off beam splitter 76 downwardly in FIG. 3 to camera means 78. Camera means 78 includes a compound lens 80 (Edmund Scientific Part #B32, 312 Achromat Objective Lens, 35 mm f.l., 12.5 mm dia, +/−0.1 mm), a pinhole device 82 (telocentric aperture pinhole −0.36 mm dia., C.A.), and an imaging device 84 (Texas Instruments TC 245, CCD Image Sensor). Camera means 78 captures the image of eye 58 and any projected beams onto eye 58 and electronically records those images. In the preferred embodiment, imaging device 84 is a CCD photo sensitive electronic area imager, such as is known in the art.

FIG. 3 shows that portion 72c of optical axis 72 allows light to pass through beam splitter 76 and beam splitter 86 into eye piece 34. The user can then directly view the patient's eye 58 along the optical axis 72. Eye piece 34 includes a lens 88.

FIG. 3 also shows additional optical components of preferred embodiment 10. A fixation LED 90 directs light from aperture 92 onto beam splitter 86. Beam splitter 86 allows some of the light to travel directly downward along axis 94 to a mirror 96. The light is then reflected back to beam splitter 86 which reflects some of the light along axis 72c to the user's eye 60. Beam splitter 86 directs another portion of the light from fixation LED 90 along axis 72c between beam splitter 86 and 76, through beam splitter 76 along axis 72a to the patient's eye 58. The fixation LED 90 therefore presents a perceivable image along optical axis 72 for the patient to fixate on. This means the patient will concentrate on looking directly at the light, not moving the eye, and not moving the head. Additionally, the projection of fixation LED 90 a distance down axis 94 to mirror 96 and back to eye piece 34 is done for the following reasons. The optical path distance between LED 90 and eye piece 34 is generally equal to the distance from the patient's eye 58 to eyepiece 34. The user will therefore perceive the image of the LED 90 to be approximately superimposed upon user's eye 60. The patient will perceive the LED image to be approximately 10 cm in front of his/her eye 58. Therefore, this arrangement gives the user a virtual image of LED 90 directly along the appropriate optical axis so that keratometer 10 can be accurately positioned with respect to the patient's eye 58.

A leveling system is incorporated into the keratometer 10 to automatically indicate that housing 24 is being held generally vertically straight up and down. A small rectangular sealed container 98 is filled partially with fluid such as oil (for example, baby oil). An LED 102 illuminates the oil in container 98, essentially back-lighting the container 98 and oil 100, including the meniscus formed at the top of the fluid in the container. The image of container 98 can travel along axis 104 portions a, b and c reflecting off of mirror 106 traveling through beam splitter 76 to camera means 78. By discerning the meniscus line between the top of oil 100 and the rest of container 98, it can be determined if housing 24 is correctly vertically positioned. It does not indicate whether housing 24 is tilted too far towards or away from the patient's eye 58, however. This alignment problem is solved by other means which will be discussed later.

FIG. 3 also shows how housing 24 contains a printed circuit board 108 which extends virtually from the lower end 40 of housing 24 through handle grip 12, intermediate portion 16, and into projection portion 14. The battery compartment 110 is also shown. In the preferred embodiment, four AA batteries are utilized to power keratometer 10. An interface between battery compartment 10 and circuit board 108 (denoted by number 112) is also shown. Contacts 114 between circuit board 108 and the end 40 of hand-grip 12 are shown which provide the communication between base 18 and keratometer 10.

FIG. 4

FIG. 4 generally depicts the side of keratometer 10 which is positioned in front of patient's eye 58. Axis 72 is directed toward the center of patient's eye 58, and the ends of projector tube 70 will issue the collimated light sources onto patient's eye 58. Aperture 116 is formed in a support 117 in housing 24, and represents the opening through which the reflection from the patient's eye 58 returns along optical axis 72 into keratometer 10.

FIG. 5

FIG. 5 depicts the side of keratometer 10 which includes eye piece 34 and control buttons 30. Display 32 is also shown along with connection 42 at the lower end of handgrip 12. Control buttons 30 can be for different desired functions or operations. In the preferred embodiments, buttons 30 relate to such things as selection of right or left eye of a patient, or measurement and storage of readings.

FIG. 6

FIG. 6 shows the opposite side of keratometer 10, similar to FIG. 4.

FIG. 7

FIG. 7 is a sectional view of the interior of projection portion 14. It shows in more detail each projector 62 according to the present invention. In particular, it shows each projector tube 70 is slightly adjustable along projector base 118. This allows a slight adjustment of lens 68 with respect to pinhole card 66 and LED 64. It is also noted that internal support 117 of housing 24 include apertures 122 along axes 74 to allow passage of the collimated light source from projector 62.

Still further, FIG. 7 illustrates that additional LEDs 124 and 126 (Hewlett-Packard Part #HLMP-7040 Green tinted, low current) can be positioned on opposite sides of LED 64 in each projector 62. Because LEDs 124 and 126 are basically in the same plane as LED 64, but are on either side of LED 64, the collimated light beams from these LEDs reaching the patient's eye 58 will cross the optical axis 72 at different angles and distances than the beam from LED 64.

FIG. 8

By referring to FIG. 8, a front view of the projector 62 is shown, which reveals the positions of LEDs 64, 124, and 126. In the preferred embodiment, LEDs 124 and 126 are green LEDs, whereas LED 64 is red.

FIGS. 9, 10, 11

Figure 9:
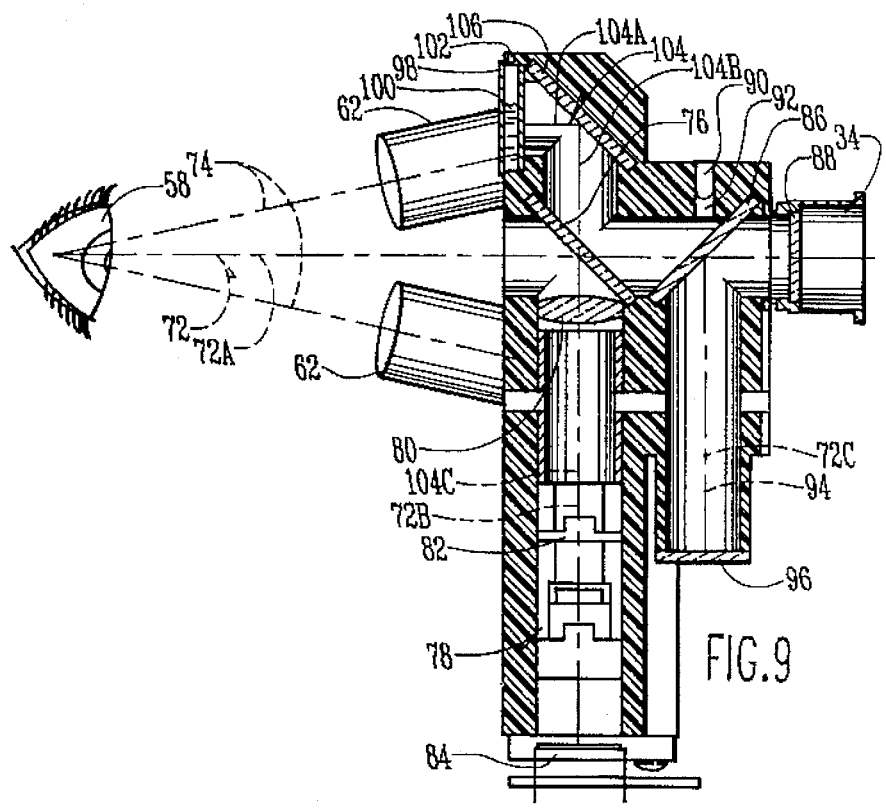
FIG. 9 is an isolated partial sectional side elevational view of the optic system of the preferred embodiment of the present invention.
Figure 10:
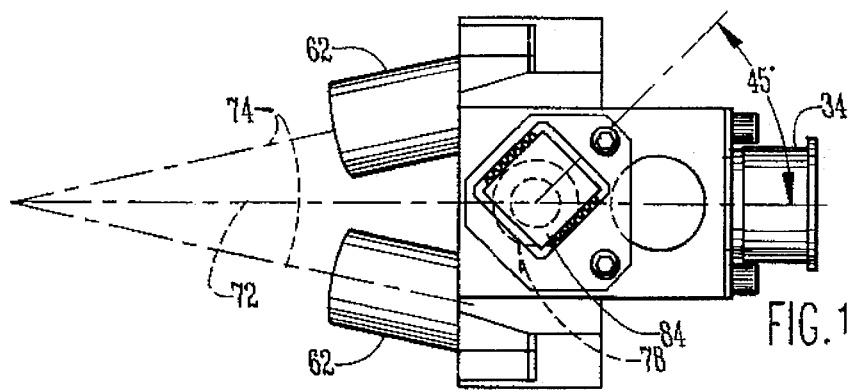
FIG. 10 is a bottom plan view of FIG. 9.
Figure 11:
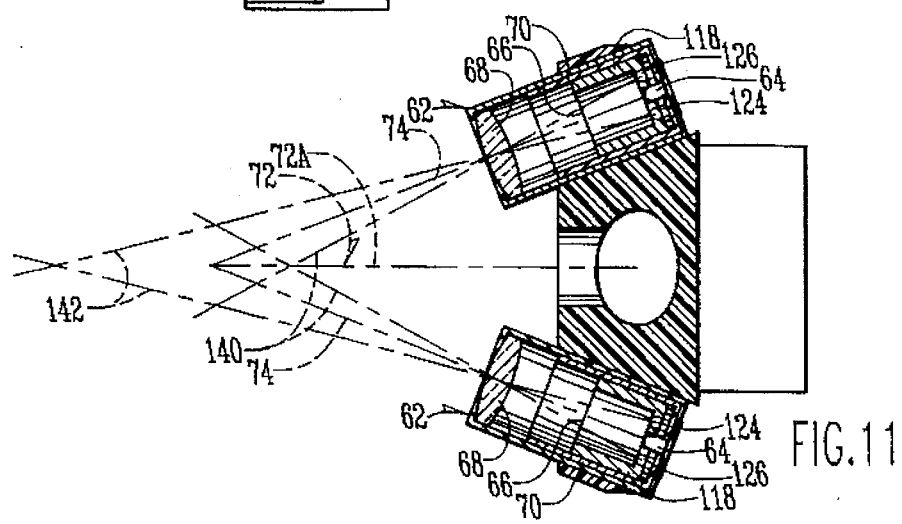
FIG. 11 is an isolated enlarged depiction of two projection means according to FIGS. 9 and 10 and the preferred embodiment of the invention.

FIGS. 9, 10 and 11 show the optical system of the present invention in more isolated fashion. FIG. 9 is similar to FIG. 3. FIG. 11 is similar to FIG. 7. FIG. 10, however, shows how the imaging device 84 is positioned basically at a 45° angle to optical axis 74. Therefore, its basically rectangular pixel array is also rotated 45° with respect to the optic axis. Note particularly how lines 140 from LEDs 126 and lines 142 from LEDs 124 in FIG. 11 show how collimated light from the different LEDs will intersect optical axis 72 at different points.

FIG. 12

Figure 12:
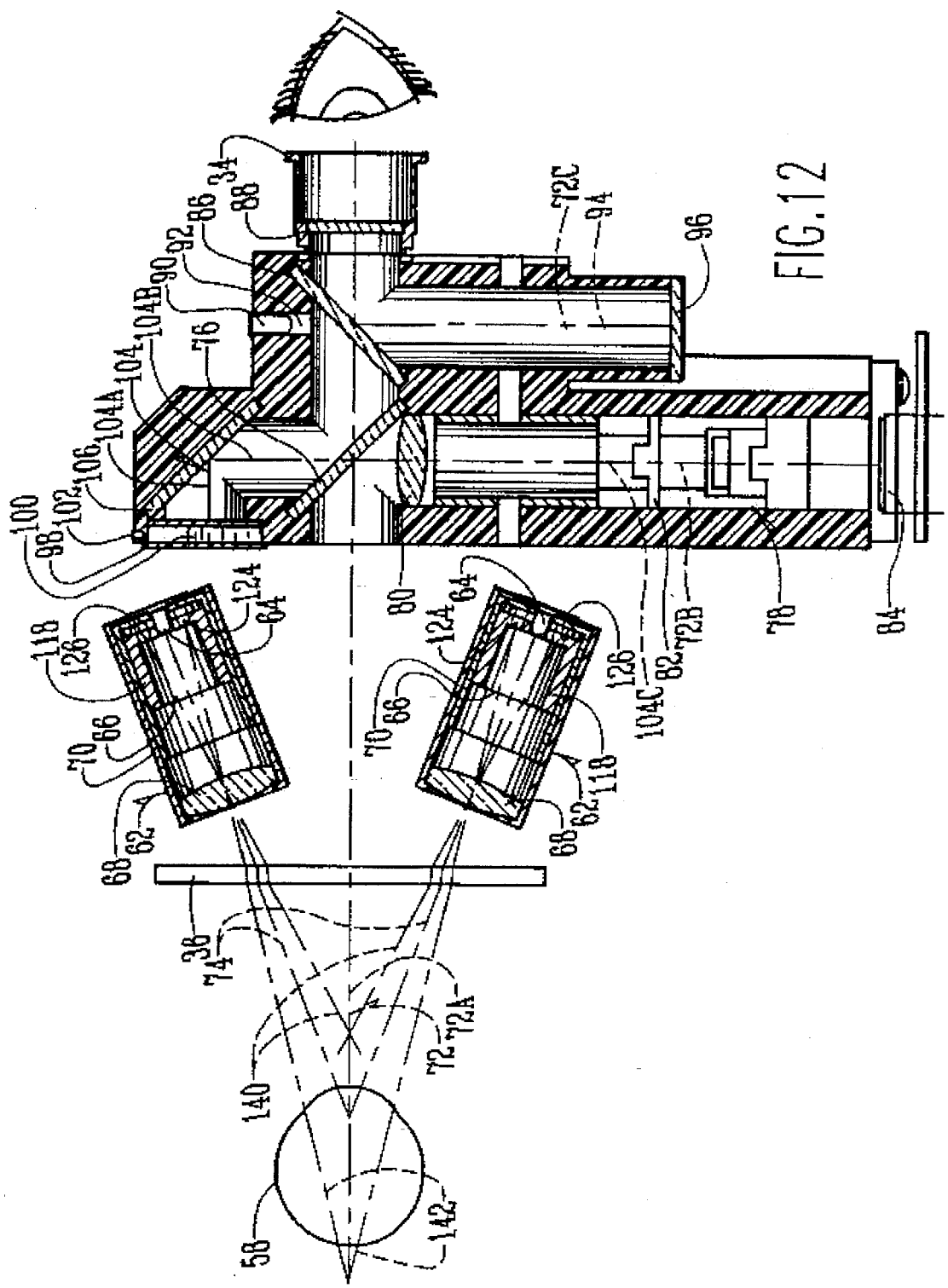
FIG. 12 is a diagrammatic view of the optical system of the preferred embodiment of the invention.

FIG. 12 shows in diagrammatic form the optical system of the present invention including relative distances between components, and the effects of the various optical features on the optical pathways. In particular, FIG. 12 illustrates how the collimated light sources 64, 124 and 126 project onto the patient's eye 58.

FIG. 13

FIGS. 13A–D diagrammatically depict a patient's eye 58. Eyeball 188 contains a cornea 190 which is generally circular in shape. The preferred embodiment of keratometer 10 imposes four LED collimated light beams 64 onto eye 58. The instrument is calibrated by measuring the position of the reflected images (200a–d) from each collimated LED light beam using a reference sphere in place of the cornea. This calibration measurement as well as subsequent corneal measurements are made using the CCD imager and its associated telocentric objective lens. The spot positions measured by reflection from the cornea and the calibration spot positions are used to compute the corneal curvature along the axis of maximum curvature, the corneal curvature along the axis of minimum curvature, and the angles that each curvature axis makes with respect to horizontal. The measurement can be made using a minimum of three spots. However, accuracy is increased when four spots are used. In addition, when four spots are used the instrument can detect that the corneal surface has a nontoric component of curvature. FIGS. 13A and 13B depict measurement where the spots 200a–d are centered at the center of the cornea for central corneal Keratometer readings. FIGS. 13C and 13D show the spots 200a–d off the center of the cornea for peripheral Keratometer readings.

FIGS. 14A–G

FIG. 14A–G depict diagrammatically various situations which can occur with keratometer 10 as seen through eye piece 34. FIG. 14a shows how fixation beam 202 can be projected and housing 24 moved to center it on cornea 190.

FIG. 14b illustrates first how LEDs 56 can impose the mire ring 57 of light on eye 58. It also shows that if all LEDs 64, 124 and 126 are turned on, as well as fixation LED 90, the type of pattern that is shown on eye 58 if correctly aligned. It can be seen that red LED 64 spots 200a–d surround fixation LED spot 202.

It can be seen that the red LED's 64 form a pattern surrounding the perimeter of the red fixation LED which is generally centered along optic axis 72. Note also that the green alignment LED's (spots 201a–d) form a similar pattern on a circle of larger radius, and green alignment LED's (spots 202a–d) form a similar pattern on a circle of smaller radius.

FIG. 14C indicates keratometer 10 is too close to the patient's eye 58. It indicates that only the outer green LED's (spots 201a–d) can be seen and neither the red LED's 64 (spots 200a–d) nor the inner green LED's (spots 202a–d) can be seen.

FIG. 14D indicates keratometer 10 is too far from the patient's eye 58. It indicates that only the inner green LED's (spots 202a–d) can be seen and neither the red LEDs 64 (spots 200a–d) nor outer green LEDs (spots 201a–d) can be seen.

FIG. 14E illustrates fixation point 202 off center.

FIG. 14F shows when the patient is not fixating on the red fixation LED 202.

FIG. 14G is a depiction of operation of keratometer 10 once green and red LED spots have been used to align keratometer 10 with respect to the patient's eye 58 (as shown in FIG. 14B). In the preferred embodiment, at this point, the control circuitry of keratometer 10 would turn off the green LEDs 124 and 126 (illustrated by "X"'s) leaving only the red LEDs 64 and the center red fixation LED 202.

FIG. 15

It is to be understood that the camera means would basically capture what corresponds to FIGS. 14A through 14G.

It should be remembered that the basically rectangular matrix of pixel cells of the CCD imager of the camera means is rotated 45° with respect to optical axis 72. The images captured by the camera means therefore are rotated 45° to correspond with the images shown in FIGS. 14A–G.

FIG. 15 depicts a centered pattern of red LEDs ready for measurement, corresponding to the pattern as shown in FIG. 14G. As has previously been explained, the two dimensional capturing of the image of FIG. 15 allows the processor to know the relative distances between the four red spots 200a–d; in turn allowing it to use algorithms and calibration spot position data and mathematical calculations to derive the radii of curvature and axis angles previously explained.

FIG. 16

FIGS. 16A–16C set forth a flow chart of the software operational steps of the preferred embodiment of the present invention.

FIG. 17

FIGS. 17–24 depict the main electrical circuitry of the preferred embodiment. This circuity exists inside housing 24 primarily on PC board 108.

FIG. 17 shows block diagram of the two main sections of the circuit board 108 of keratometer 10, namely, the main board 302 and an input/output section 304.

FIG. 18

FIG. 18 shows a partial diagrammatic and partial schematic view of the input/output section 304 circuit board 108, including the keyboard section 306 which relates to the control button the LED's of keratometer 10.

FIG. 17 shows that i/o section 304 includes an LCD display 308, the keyboard section 306 and LED outputs 310.

Main board 302 includes a DC/DC Converter 312, micro processor 314, image processors 316, and CCD interface 318.

FIG. 18 more specifically shows that i/o section 304 contains the LCD display 308 and the driving circuitry for back light LEDs 320, to back light the LCD display. It also includes LED drivers 322 to drive the various LEDs in the system. A keyboard interface 324 allows interaction of the actual keyboard which is 306 (see switches S1–S15) with the circuitry. Additionally a beeper driver 326 is used to operate a transducer which issues an audible signal to the operator, according to software.

FIG. 18 illustrates the inter connections it would have with other components, for example input/output connections 328 would communicate with the main board 302. Header 330 connects the LED drivers 322 to the actual LEDs.

FIG. 19

FIG. 19 shows in detailed electrical schematic i/o section 304.

FIG. 20

FIG. 20 shows in block diagram form the contents of the main board 302.

It can be seen how micro processor 314 communicated with image processor 316, which in turn is communicated to CCD interface 318. FIG. 20 also shows the inter connections of micro processor 314 with i/o section 304 at reference numeral 332. Headers 334 and 336 comprise the communication between keratometer 10 and base 18. Header 338 communicates the image processor 316 and CCD interface 318 with the CCD imager 84.

FIG. 21

FIG. 21 shows in detailed electrical schematic CCD driver section 318 of the main board.

FIG. 22

FIG. 22 shows in detailed electrical schematic the power supply circuit 312 for keratometer 10.

FIG. 23

FIG. 23 shows in detailed electrical schematic microprocessor 314 for the main board 302.

FIG. 24

FIG. 24 shows in detailed electrical schematic the image processor circuit 316 of the main board 302.

To allow a more complete understanding of the preferred embodiment of the invention, below is a detailed description of the electrical circuits previously identified and shown in the drawings, as well as the operation of that circuitry.

FIG. 25

FIG. 25 is a general block diagram of the overall circuitry of the preferred embodiment. Reference to FIG. 25 will assist in understanding the sections and interconnection of sections of the circuitry, as well as be a helpful reference when reading the detailed description of the operation of hardware and software, which follows.

FIGS. 26–27

These figures are block diagrams of the imaging processing parts of the circuitry and will assist in an understanding of this part of the invention.

FIGS. 28–33

These figures supplement the main electrical schematics and depict various electrical circuits and boards that can be used with the preferred embodiment.

FIGS. 34A–34B

This chart is helpful in understanding the software operation of the preferred embodiment. FIGS. 34A and 34B are on a chart which should be read from bottom to top of FIG. 34A and then bottom to top of FIG. 34B.

FIGS. 35–38

These electrical schematics show details of the image processing circuitry and should be referenced particularly with Section F entitled "Image Processing Algorithm", and following Section G.

In the following section D, entitled "Electronic Circuit Operation", and Section E entitled "Keratometer Operation", references to sheets 1–8 corresponds as follows to FIGS. 17–24 of the drawings.

| SHEET | FIG. |
| --- | --- |
| 1 | 17 |
| 2 | 18 |
| 3 | 19 |
| 4 | 20 |
| 5 | 22 |
| 6 | 24 |
| 7 | 21 |
| 8 | 23 |

D. ELECTRONIC CIRCUIT OPERATION

1. INTRODUCTION

1.1. General
This document contains a technical description of the electronic part of the Keratometer. The electronic part of the Keratometer, discussed in this document, include two Circuit Boards. The 'Main Board', and the 'CCD Imager Board', both located inside the same enclosure, and are attached to each other to form a single assembly.

1.2. Scope
This document contains description of the electronic circuits implemented on these two boards. The description relies on the Boards' schematics, that are attached to this document. The level of details in this document is sufficient to understand the basic functions and operations of the Keratometer's boards.

1.3. Schematics Structure and Conventions
The schematics of the Main Board are hierarchicaly structured in 8 sheets marked as sheet 1 to sheet 8. The CCD board is confined within one sheet. The Main Boards' schematics sheet 1 includes only two sub blocks: IOSEC and MAIN, that are detailed on sheets 2 and 4 respectively. Sheet 2 contain some circuits and one sub-schematic detailed on sheet 3. The schematics in sheet 4 contains sub-schematics detailed on sheets 5, 6, and 7.

The electrical connection between schematic sheets is implemented using a terminal (also called 'module port') designated with a unique name, two identical names of module ports on different schematics are connected together. Two identical names within the same schematic sheet are also connected together, but have no meaning outside the sheet. For example, if we look at sheet 1 of the Main Board schematics, the block called MAIN have an input called 'CALIB' which comes from a port carrying the same name in block IOSEC, these signals are connected together. If we look at sheet 4 (which contain the content of block MAIN on sheet 1), we see the CALIB input at the top left corner, and it is connected to the MIP block which is further described in sheet 6.

2. MAIN BOARD SCHEMATICS DESCRIPTION

2.1. Main Board Sheet 1
Sheet 1 contains two sub blocks: IOSEC that contains mainly the input / output functions, and MAIN that contains mainly the signal processing parts of the Keratometer. Both of these are further detailed on sheets 2 and 4 respectively.

2.2. Main Board Sheet 2
Sheet 2 contains the operational pushbutton switches, the back light LEDs, the speaker, the header for the projection assembly and a modular block of sub-schematic on sheets3.

2.2.1. Operational Switches

Sheet number 2 contains 13 momentary push-button type switches (designated S1, S2, and S4 to S9) which are used to control the Keratometer operations. These switches are also collectively referred to as "the keyboard". When a push button is pressed by the user, one of the inputs to the IO block (designated K1 through K7) is momentarily shorted to ground or to the VCC potential, depending on the switch wiring. The switches' functions are defined by the system software. The microcontroller always reads the status of all switches, thus functional assignment of these switches is arbitrary. is assigned by the micro controller, the names of these switches are: Select, Scroll, Clear, Right Eye, Left Eye, and Measure. A more detailed description of the functionality of these switches will be provided in the operational chapter.

The Measure switch is an exception. It consists of 8 switches, all activated together by a single button, and are made of three groups: S6, S10, S7, and S12 are all attached to circuit port K6, and inform the processor that the Measure key was depressed. The second group consists of S11, S9 and S13, and is wired to port K7, which provides interrupt to the microcontroller (Sheet 8), needed to wake up the microcontroller from "sleep mode", the power saving mode. The third group is the switch S8, which is wired to the system's _RESET signal, to be used to restart the system if it has reached a deadlock for unexpected reasons. To avoid system reset every time the Measure button is depressed, S8 is qualified (i.e. receives ground potential) by S14 above, thus only if both S14 (Scroll) and the Measure button are both depressed, the system will reset and will take precedent of the other functions of these keys.

2.2.2. Header JP9

The connector-header JP9 provides all of the connections with the various LEDs mounted on the optical sub assembly of the Keratometer. The signals are described in the following table.

| Pin | Name | I/O | Description |
|---|---|---|---|
| 1 | RIGHT | Out | Turn ON right projection LED |
| 2 | TOP | Out | Turn ON top projection LED |
| 3 | MIRE | Out | Tun ON Mire ring |
| 4 | BOTT | Out | Turn ON bottom projection LED |
| 5 | LEVEL | Out | Turn On LED to observe level |
| 6 | LEFT | Out | Turn ON left projection LED |
| 7 | Not Connected | | |
| 8 | Ground | | |
| 9 | Not Connected | | |
| 10 | AIM | Out | Turns ON AIM LED. |
| 11 | P3 | Out | Turns ON the four central projection LEDs. |
| 12 | P2 | Out | Turns ON four of the non-central projection LEDs. |

| 13 | VCC | | +5V Power. |
|----|-----|---|------------|
| 14 | P1  | Out | Turns ON other four of the non-central projection LEDs, in conjunction with P2. |

Table 1: JP9 connections

2.2.3. Backlight LEDs

The Light Emitting Diodes (D1 through D14) are physically located behind the LCD (Liquid Crystal Display), and are used to illuminate the display to allow reading in a dim environment. The current that drives the back light LEDs is generated in sheet 3, and controlled by the micro controller.

2.2.4. Speaker

The speaker (LS1) is used for audible indication with two available sound pitches. The generation of the signals for the speaker is detailed in sheet 3 of this board.

2.3. Main Board Sheet 3

Sheet 3 contains most of the input output functions of the Keratometer. It contains the LCD itself, the LCD drivers, and the LCD contrast control, the serial load and read circuitry, the push button keys read function, and the sound control.

2.3.1. LCD Drivers and Display

The main board contains two LCD driver devices (U1, and U2). These devices are loaded by the micro controller (see serial load control). The drivers provide all the required signals and voltages to the LCD (U21). The voltages to the driver (VLCD1, VLCD2, and VLCD3) are supplied by resistor voltage dividers, and a contrast control (VLCD3) that is described separately. The LCD can be reset by the micro controller in pin 13 of U1 and U2. The micro controller synchronizes its access to the driver by sensing the 'busy' line from all the drivers (pin 11 on the drivers that is driven to module port named '_BUSY'). The LCD driver requires a clock with a frequency of 100 KHz, the dual divider U10 provides this clock by dividing the 8 MHz main crystal oscillator by 10 (U10A) and then by 8 (U19B), which provide the required division factor of 80. The Liquid Crystal Display consists of various visual symbols. The micro controller can address each symbol by sending a control sequence to either U1 or U2, addressing the desired symbol.

2.3.2. Serial Load Control Circuitry

The serial load circuit is used to load multiple registers by the micro controller, it provides a method of setting control values with minimum use of outputs from the controller. The circuit includes a destination selector U3 (left side of the sheet), which selects the device to be controlled by the micro controller, and loading shift registers U7, U6, and U5. These shift registers are loaded with several bits, each controlling the operation of another device, such as LED and speaker.

The devices to be selected by U3 are detailed in table 2. The serial load operation of bits from the micro controller includes the following steps, the are shown also in Diagram 1.

1) The micro controller sets the 3 'select' inputs of U3 (sel0, sel1, and sel2) to the required destination value (between 1, 2, or 7, see table 2).
2) The micro controller set the value to be loaded on its output port (module port MOSI, net called DATAIN).
3) The micro controller toggles the serial clock (module port SCK, net called SERCLK) to high value and then low. This operation causes the data on the MOSI line to be shifted into the shift register.
4) Steps 2 and 3 are repeated until all the bits are loaded to the selected device.
5) The micro controller removes the data value from the MOSI line.
6) The micro controller sets the selector inputs to value 0 for no operation.

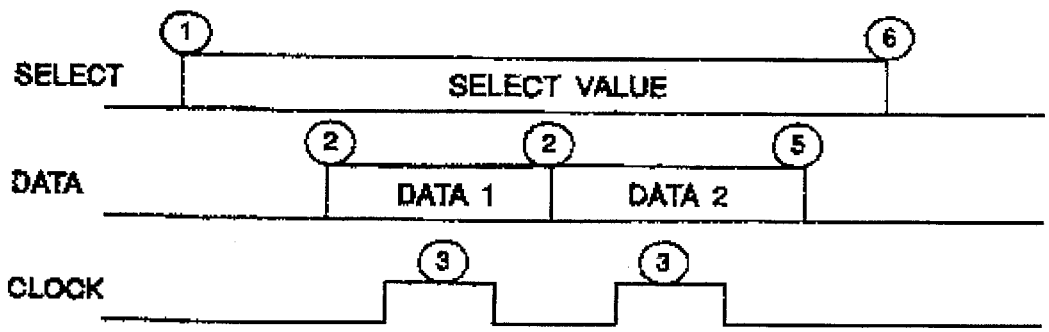

Diagram 1 : Serial Load Process Steps

| Select | Device's Port | Description |
|---|---|---|
| 0 | Disabled | The serial shift load/read is disabled. |
| 1 | LCD driver U1 | Defines the display on the LCD. |
| 2 | LCD driver U2 | Defines the display on the LCD. |
| 3 | Switches Read Enable | Allows the micro controller to scan the 8 external push button switches. |
| 4 | Load Switches | When selected, the condition of the 8 push button keys is loaded to the shift register. |
| 5 | Not Used | |
| 6 | Not Used | |
| 7 | Keratometer controls | Includes the contrast control, LCD back light control, LCD reset, calibration enable, sound control, and the projector LEDs content |

Table 2: Select Inputs to the Destination Selector

2.3.3. Push button keys read function

The push button keys function is shown at the bottom left part of sheet 3 (the keys are physically drawn in sheet 2). Each of the keys is an input to an eight bit parallel load shift register (U4). The micro controller periodically reads the push buttons to check whether a button was pressed by the user. The read operation is a serial read which is similar to the serial load, and includes the following steps:

1) The micro controller sets the 3 'select' inputs of U3 (sel0, sel1, and sel2) to the value of 3 which cause the Y3 of the selector (U3) to become active (low). This operation loads the state of all switches to the shift register.
2) The micro controller releases the condition of 'load serial' by loading 0 to the selector.
3) The micro controller sets the selector to value 4 which enables the serial read operation (release the clock inhibit input of the U4).
4) The micro controller reads the value at its input port (module port MOSO, net called DATAOUT).
5) The micro controller toggles the serial clock (module port SCK, net called SERCLK) to high value and then low. This operation causes the data in the shift register to move one cell and to present the next switch on the MOSO line.
6) Steps b and c are repeated 8 times until all switches have been read.
7) The micro controller sets the selector inputs to value 0 for no operation.

2.3.4. LCD Contrast Control

The user can change the contrast of the LCD illumination to achieve maximum display clarity. The change in contrast is achieved by changing the voltage of VLCD3 (pin 5) of the LCD drivers U1, and U2. The variable voltage to VLCD3 is set by the loaded bits Qa to Qd in U7. These four bits provide 16 steps of contrast. The value that is loaded to Qa,Qb,Qc, and Qd is fed to 4 inverters (U8A, U8B, U8C, and U8D) that are feeding a resistor network (R34, R35, R36, and R37), forming a basic 4 bit D/A function.

2.3.5. Sound Control

The Keratometer is equipped with a small speaker to provide audible indication to the user. The micro controller has 2 bits to control the audible alarm: (1) the 'sound' 'High Pitch' enable which start generation of a continuous tone, and (2) the High Pitch bit, when this bit is set the sound is generated with higher frequency. The circuit contains a buffer/inverter U8E, and a tone oscillator (U9). The tone frequency change is achieved by changing the time constant of the oscillator through the diode D29. The sound is delivered through a 100 ohm resistor to the module port designated 'SPKR', the speaker itself is drawn and mentioned on sheet 2.

2.4. Main Board Sheet 4

Sheet number 4 contains the sub-schematic of the DC/DC converter (described in sheet 5) that provides most of the necessary voltages used by the Keratometer, the connector JP6 (left top) is used for battery connection, the connector J5 is used to connect the Keratometer to its base (explained later). The micro processor, also referred as micro controller, (described in sheet 8), the image processor (described in sheet 6), and the CCD Imager drivers are also described here as sub schematics. The header JP7 connects the main board with the CCD board.

2.4.1. CCD imager connector

The CCD imager connector (JP7) is described in the table 3.

| Pins | Name | I/O | Description |
|---|---|---|---|
| 1 | C1 | In | Serial CCD Data line (1 of 3) that contain the picture's data. |
| 2 | C3 | In | Serial CCD Data line (1 of 3) that contain the picture's data. |
| 3 | C2 | In | Serial CCD Data line (1 of 3) that contain the picture's data. |
| 4 | DPI | Out | Shift CCD image to Storage area located on CCD device below image area |
| 5 | DAB | | Anti-blooming clock to improve CCD performance. |
| 6 | DPS | | Shift image from storage area on CCD to the output register. |
| 7 | DS3 | | One of three phases of image read-clock in CCD device. |
| 8 | DS2 | | One of three phases of image read-clock n CCD device. |
| 9 | DS1 | | One of three phases of image read-clock n CCD device. |
| 10 | DT | | Push image row to three phases of image shift register n CCD device. |
| 11 | VCC2 | | 5 Volts supply |
| 12 | P12C | Out | 12 Volts supply |
| 13 | DA0 | Out | D/A output for the CCD threshold (bit 0) |
| 14 | DA1 | Out | D/A output for the CCD threshold (bit 1) |
| 15 | DA2 | Out | D/A output for the CCD threshold (bit 2) |
| 16 | DA3 | Out | D/A output for the CCD threshold (bit 3) |
| 17 | DA4 | Out | D/A output for the CCD threshold (bit 4) |
| 18 | DA5 | Out | D/A output for the CCD threshold (bit 5) |
| 19 | DA6 | Out | D/A output for the CCD threshold (bit 6) |
| 20 | DA7 | Out | D/A output for the CCD threshold (bit 7) |
| 21 | N7V | | -7 Volts supply |
| 22 | Not Used | | |

Table 3: CCD Imager Connector (JP7)

2.4.2. Battery connector

The battery connector (JP6) is used to connect the main board to the battery, it has only two pins for the battery connection.

2.4.3. Base connector

The base connector (JP5) is used to connect the Keratometer to its base. The base connector is described in table 4.

| Pins | Name | I/O | Description |
|---|---|---|---|
| 1 | VBASE | In | Provides voltage to charge the Keratometer's battery |
| 2 | SERIN | In | Serial input data line (see serial communication sheet 8) |
| 3 | SEROUT | Out | Serial output data line (see serial communication sheet 8) |
| 4 | GND | - | Ground connection |

Table 4: Base Connector (JP5)

2.5. Main Board Sheet 5

Sheet number 5 contains the circuit of the power supply that includes the voltage regulators, the transformer, the switching mechanism and the sleep-mode control.

2.5.1. Voltage Regulator and Transformer

The main IC that is used is the 'Step-Up Switching Regulator' (U11). The purpose of this IC is to provide an accurate AC source for the transformer T1 to generate the various required voltages. The current source to the power supply is the battery source (VBAT), which is charged by voltage VBASE fed through D35. The inputs voltage drives U11 to switch the FET gate Q5 and generate the required square wave AC signal to the transformer primary side.

The secodary side of the transformer generates the voltages required by various parts of the Keratometer, some are switched and turned on only during measurement. The following is a list of the generated voltages:

| Name | Voltage (Volts) | Comments |
|---|---|---|
| P12V | +12 volts | continuous, except during sleep |
| P12C | +12 volts | switched |
| P1V5 | +1.5 volts | switched |
| N7V | -7 volts | switched |
| N9V5 | -9.5 volts | switched |
| VCC | +5 volts | continuous, except during sleep |
| VCC1 | +5 volts | continuous, for micro controller |
| VCC2 | 5 volts | switched |

Table 5: Voltages Generated by the DC to DC Convertor

2.5.2. Power Supply Regulation

The power supply regulation is achieved by sensing the VCC, and feeding it back to the regulator to pin VFB (pin 7) of U11. If VCC is too high, the driving of Q5 stops momentarily, until VCC returns to the desired level. All other voltages are also regulated indirectly, by the virtue of being fed from the same transformer T1 as the regulated VCC winding. This technique is used to ensure that all the voltages will be set accurately following this voltage.

2.5.3. Switching Mechanisms

All the voltages generated by the converter can be shut off by the microprocessor with the 'sleep' input (bottom left corner). This mode is used during a long period of non operating time. In sleep mode, transistor Q6 becomes high impedance, lifting R49 from ground and causing the regulator U11 to stop driving Q5, thus the transformer T1 is inactive. The microcontroller needs 5V supply even during sleep, thus a power line VCC1 is feeding the micro controller always. VCC1 is connected to VBAT via D42, which ensures power level when VCC is zero.

As shown in the above table, all the voltages to the CCD Imager can be switched off, these voltages are needed for a short period of time during measurement only. Switching the voltages is performed by the PB line (top left corner) that is generated by the Image Processor and stays active (high) during the whole measurement cycle. When PB is active, transistor Q9 is turned on, which turns on transistor Q7, that turns on the +12 volts to the imager. This 12 volts line is also connected to the gate of Q13, that turns on the 1.5 volts, and to the gate of Q11 that pulls down terminal number 5 of the transformer T1 that causes the negative voltages -7 and -9.5 volts to became active. VCC2 which is the imager +5 volts supply (at the bottom right corner) is also controlled by the 12 volts that activates the gate of Q8.

2.5.4. Battery Monitor

If the Keratometer is over used without charging, the battery may drain to almost zero volts. The logic state of the circuit is unknown, and is likely to include a high-current consumption mode, such as RESET. This will preclude charging the battery, since most of the charging current will be consumed by the circuit. To avoid this event, a battery monitor, U22 is provided. It forces SLEEP mode if battery voltage goes below 4V, and has hysteresis that maintains sleep until battery has reached at least 4.3V.

2.6. Main Board Sheet 6

Sheet 6 contains the main crystal oscillator, the image processor and the random access memory that is used by the micro controller and the image processor.

2.6.1. Crystal Oscillator

The 8 MHz crystal oscillator (U14), that serves both the image processor, and the LCD clock (described on sheet 3).

2.6.2. Image Processor

The image processor (U12) is a field programmable gate array ACTEL 1020. The content of the image processor and the processing algorithm are described later.

The image processor's left side is basically connected to the micro processor with data lines, address lines and controls, these are described with some more details in the micro processor section (sheet 8). The image processor generates all the necessary timing signals to the CCD (right bottom of U12), and receives the 3 serial inputs C1, C2, and C3 that actually contains the digital description of the picture.

The signals that are generated by the image processor and are used to drive the CCD via drivers (Sheet 7) as follows:

| Mnemonic | Name/Description |
|---|---|
| ABIN | Anti-Blooming Clock |
| PI | Imager clock |
| PS | Storage Clock |
| T | Transfer Gate Clock |
| GT | Vertical Retrace |
| S1,S2,S3 | Serial Image read Clocks |
| PB | Power ON video circuitry |

Table 6: The signals driving the CCD drivers

2.6.3. Random Access Memory

The image processor is also connected to a Random Access Memory (U13) that contains 8K bytes of data. During normal operation, the image processing function of the image processor is disabled and the micro controller can access the 8K bytes memory. During measurement, that requires capturing of a picture, the image processor takes priority on the memory and writes the processed image data to the memory. At the end of the measurement, the image processor becomes inactive again, and the captured data in the memory is available to the micro controller.

2.6.4. Calibration Provisions

During calibration of the CCD as part of the manufacturing process, it is necessary to have a memory that is larger than the memory provided on board. For the calibration process, a special IC clip is hooked on top of the memory device (U13), and connects to a special board that contains control circuit and 64K RAM. Pin number 1 of U13 which is usually not connected, are used by the micro controller to clear the calibration control circuit. The calibration clip connects pin 22 of the on board RAM (U13) to ground to disable the on board memory chip. During the calibration process, the micro controller turns the image processor also to its calibration mode and the data captured during these measurements is loaded to the external memory instead of the on board memory. After the measurement, the micro controller can reset the external memory control and can read all the externally stored data in sequential order.

2.7. Main Board Sheet 7

Sheet number 7 contains the drivers to the CCD imager, and the CCD voltage adjustments.

2.7.1. CCD Imager Drivers

The circuit contains two specific devices that are tailored to drive the Keratometer's CCD imager. The parallel driver (U15) translate the parallel sync pulses that drive the CCD to analog voltages DAB, DPI, and DPS that are required by the CCD specifications.

The serial driver (U16) drives the clocks that are 'pushing' the picture into the serial data lines for readout. The driving signals that enter the left side of the sheet are generated by the image processor and described along with the image processor description on sheet 8.

2.7.2. CCD Imager Voltage Adjustment

There are 3 adjustment potentiometers that set the voltages to the driver U15 during production of the Keratometer in order to match the performance to the specific CCD that is installed in the Keratometer.

2.8. Main Board Sheet 8

Sheet 8 contains the micro controller (U20), the address Latch (U17), the program memory (U19), the D/A latch (U18), and optional TTL serial communication channel (JP8, and JP13).

2.8.1. Micro Controller

The micro controller is Motorola 68HC11 which includes the following basic characteristics:

512 bytes RAM
512 Bytes EEPROM (Electrically Erasable Read Only Memory)
Address, Data and I/O PORTS, allowing access to external memory.
8 Analog Ports with internal A/D Converter
Controls The basic clock oscillator is generated inside the micro controller using an external 13.2 MHz crystal (Y1). The micro controller can be reset externally by the _RESET line, this reset causes a complete initialization of the micro controller as after power up.

The following is a list of all the external ports of the micro processor and their uses, the list of ports can give the reader a better understanding of the available control and status. Some of these lines are explained on the sheets where used.

| Port | Name | I/O | Description |
|------|------|-----|-------------|

| Port | Name | I/O | Description |
|---|---|---|---|
| PA0 | CPTTL | | unused |
| PA1 | MRXD | Input | Sense serial in activity to read print request from base |
| PA2 | _BUSY | Input | Monitor readyness of LCD drivers |
| PA3 | Select0 | Output | The select lines are used to control which device is accessed by the serial load / read mechanism (explained in details in sheet 4). |
| PA4 | Select1 | Output | The select lines are used to control which device is accessed by the serial load / read mechanism (explained in details in sheet 4). |
| PA5 | Select2 | Output | The select lines are used to control which device is accessed by the serial load / read mechanism (explained in details in sheet 4). |
| PA6 | PWM | | |
| PA7 | SLEEP | | |
| PB0 - PB7 | MAH0 - MAH7 | Output | This port contains the 8 higher bits of the 16 available address bits supported by the micro controller. |
| PC0 - PC7 | D0 - D7 and MAL0 - MAL7 | Input / Output | This port is multiplexed between the lower 8 bits of the address bus and the data bus (see description under Address Latch) |
| PD0 | MRXD | Input | Serial UART receive line (details in sheet 1) |
| PD1 | MTXD | Output | Serial UART transmit line (details in sheet 1) |
| PD2 | MOSI | Input | Defined as an input to sample the serial read of the push button switches (details in the chapter of the serial read mechanism, sheet 4) |
| PD3 | MOSO | Output | Defined as an output and used for the serial load data (details in the serial load control sheet 4) |
| PD4 | SCK | Output | Serial clock used by the serial load and read control (details in the chapter of the serial read mechanism, sheet 4) |
| PD5 | SS | | |

| | | | |
|---|---|---|---|
| PD6 | E | Output | Continuous clock from the micro controller that times the read / write cycles. |
| PD7 | AS | Output | Control signal used to latch the lower address lines with an external latch (see Address Latch description) |
| PE0 | | Input | Analog monitoring of 12V voltage |
| PE1 | | Input | Analog monitoring of 1.5V voltage |
| PE2 | | Input | Analog monitoring of -7V voltage |
| PE3 | | Input | Analog monitoring of -9.5V voltage |
| PE4 | | Input | Analog monitoring of base voltage, can indicate if keratometer plugged to base |
| PE5 | | Input | Analog monitoring of battery voltage VBAT |
| PE6 | | Input | unused |
| PE7 | | Input | unused |

Table 7: Micro Controller Input / Output Ports

2.8.2. Address Latch

The micro controller drives the 8 lower bits (MAL0 to MAL7) of the address on the same lines with the data bus D0 to D7. When the address lines are driven out (on the lines designated as D0 to D7 in U20), the micro controller also activates the AS signal (pin 4 of U20), that cause this data to be latched into the address latch U17. Then the controller can send data on the data lines to the desired address or receive data through these lines.

2.8.3. Main Program Memory

The main program memory is a 64K bytes Erasable Read Only Memory EPROM (U19). This memory is connected directly to the micro controller and accessed solely by the controller. Most of the Keratometer software is stored in this EPROM.

2.8.4. D/A Latch

This latch (U18) is used to hold the value of the D/A that control the CCD threshold. The latch is connected to the micro controller data bus and loaded by a signal decoded in the image processor, called _DAEN (more details in the CCD board description).

2.8.5. TTL Serial Communication

The serial communication lines to receive and transmit are normally routed to the RS-232 convertor (explained in sheet 1), however, during calibration or test, the manufacturer can connect a TTL serial connection through the headers JP8. JP13 is a jumper to set the serial input. If the data source is a TTL level signal, the jumper connects pins 1-2, if the source is an external RS-232 signal, the jumper connects pins 2-3.

3. CCD IMAGER BOARD SCHEMATICS DESCRIPTION

The CCD Imager Board is located at the top of the Keratometer, it contains the CCD imager device, the analog amplifiers of the three video channels, the threshold circuit, and the D/A that sets the sensitivity level of the comparators.

3.1. Connection Header

The electrical connection of the imager board to the main board is handled through the header JP1 (top left). This header is detailed in sheet number 5. The ground connection to the board is connected through a separate jack (J1).

3.2. The CCD Imager

The imager (U1) is the basic element of a video camera, it provides a full picture of the reflected light source through the measured lens. The image result which is the intensity of each of the imager sense points is shifted out of the device through the outputs VO1, VO2, and VO3. These serial lines are actually analog signals that represent the intensity of each pixel. The serial analog output from the imager is amplified by the operational amplifiers U5, U6, and U7 by a factor of about 10, and then compared to a threshold value by the comparators U4A, U4B, and U4C. For each comparator, if the amplified signal at the input to the comparator (pin 1) is lower than the threshold value in pin 2, the output of the comparator is negative, which means that a true signal was detected.

3.3. Threshold D/A:

The threshold is needed to adjust the sensitivity of the reading with regard to the specific imager and the ambient light conditions. The Keratometer is adjusting this value automatically. The threshold is a digital voltage that is generated by the Digital to Analog converter (U2). The input to the converter is a 7 bit word from a latch (described in sheet 8), these 7 bits control the output analog voltage in pin 8 of the D/A.

3.4. Voltage regulator

The voltage regulator (U3 at the bottom of the page) is responsible for regulating the negative 5 Volts for the amplifiers and the comparators, it uses the negative 7 Volts as a source.

E. KERATOMETER OPERATION

1. INTRODUCTION

1.1. General

This document describes the operation of the Keratometer Circuit. The reader must be familiar with the circuit description, available previously. This document makes direct references to the Keratometer and CCD Boards' schematics pages described in the circuit description document. (Section D)

1.2. Scope

The operation of the Keratometer is controlled by the software residing in the EPROM, and by the hardware executing it. This document describes the hardware operation, by means of examples.

2. Startup Description

When the batteries are first attached to the Keratometer, a power-on reset occurs. The voltage regulator, U11 sheet 5, detects low voltage at pin 1 LBI since C50 is not charged yet. This triggers pin 2 LBO of U11 to reset the circuit. The micro controller U20 on Sheet 8, senses the reset at pin 17, and goes to reset mode, which includes setting all microcontroller's I/O ports as inputs. This includes I/O PA7 (pin 27) which controls sleep mode.

Since pin 27 U20 is in input mode, the signal _MSLEEP (top right of sheet 8) is pulled HIGH by resistor R89, which commands the system to wake up. The signal _MSLEEP arrives in sheet 5, where it causes U11 to operate again, creating VCC and P12V voltages. The VCC voltage is supplied to most of the Keratometer logic, including the program EPROM U19.

Now, that there is power, the microcontroller is able to execute code from the EPROM. This code (software) initializes all desired registers in the system, performs self test etc. Example of the self test is the reading of voltages at the PE1 thru PE5 ports (U20), and verifying that all of these voltages are within acceptable range. At the end of this reset period, the microcontroller waits for user's requests from the keyboard, and if none exists, it executes the sleep routine, which forces U20 pin 27 _SLEEP to become LOW and turns off all power, except for VCC1 for the microcontroller itself.

3. Measurement Operation Description

Assuming that the Keratometer is in sleep mode. When the Measure key is depressed (sheet 2), a wake up signal _WAKEUP is propagated via sheet 3 and 4 to signal LCD 9-pin 18 of U20, which indicates to the microcontroller to resume normal operation. Pin PA7 _SLEEP is turned ON, which causes activation of the DC/DC converter as described above. The microcontroller's software now polls the keyboard operation to wait for use's keys. Suppose that the user presses the RIGHT EYE key on sheet 2. The signal K4 goes HIGH, leading to U4 at the bottom left of sheet 3. The microprocessor outputs a serial clock via pin PD4 (U20 Sheet 8), which reaches U4, causing it to shift all eight bits to the line DATAOUT, also called MISO, which reaches the microprocessor's serial port PD2 pin 22. The microprocessor reads this byte, and the program detects a HIGH in the bit position related to RIGHT EYE. This causes the program to update its content, including updating the LCD display to show the symbol of a right eye. This display update is done by setting the SEL0 thru SEL2 signals on page 2, (coming from the microcontroller) near U3 to binary 001, causing Y1 (pin 14 of U3) to go LOW and thus selecting U1, the LCD driver. Now a sequence of bits arrives from the microcontroller via the MISO line, which is written into U1. This bit stream includes the appropriate command to turn ON the LCD segment on U21 that shows a right eye symbol. In addition, the user gets an audible beep to indicate that the key has been read. This is done by sending a similar serial bit stream to the shift registers, comprising U7, U6, and U5, and setting _SOUND pin 4 of U7 LOW, which activates the sound via U8E and U9, both at the top left corner of sheet 3. All of the other bits of U7,U6, and U5 are also updated, but since there is no need to change them now, the software ensures that the bit stream sent to them is identical to their previous state, and only the sound is activated. After a brief period, another bit stream is sent, this time to turn the sound OFF, so that only a short beep is heard between these two shift register updates.

The user keeps pressing various buttons, causing the program to respond as needed. Eventually, the Measure key may depressed, causing the start of a measurement process.

When starting the measurement process, the mocro controller writes to the image processor U12 sheet 6, which is accessed as a memory address. Inside the image processor there are registers used for command/indication handshake with the microcontroller. The microcontroller writes the command to one of these registers to turn the power ON, which sets the signal PB U12 pin3, arriving on top left of sheet 5, which turns ON all power supplies. At this time, the image processor outputs also all the periodic signals necessary to read the video image, such as PI, PS, GT etc. and the CCD Board is fully active. After the voltages have settled, the microprocessor sends a bit stream to the register U7,U6,U5, as discussed above, but this time the desired combination of projection LEDs, level and mire, are turned ON. The user starts to align the Keratometer near the patient's eye. The microcontroller writes a "grab image" command to the image processor. The image processor grabs images by reading the inputs C1,C2,C3 (pins 63,64,65 U12 sheet 6), and runs the internally built image processing algorithm, discussed in a separate document. As useful video information is detected, the image processor writes this information to the image RAM U12 sheet 6. This information relates to the location and sizes of light spots detected. When a full video frame processing is complete, the image processor indicates completion status by changing a bit in an internal status register, which is polled by the micro controller. The microcontroller now can read the RAM via the image processor, which acts at this time merely as a switch, connecting the microprocessor address and data busses with the image RAM busses. The RAM is also used by the micro controller to store information needed for its programs, in memory areas not used currently for image grabbing. To assist this separation between information types, the RAM is arranged as four pages of 2K bytes each, of which only one page at a time is used for the image grabbing. The micro controller can set image processor registers that will force it to store the next images at any of those pages, leaving the other three for general purpose storage.

After an image is grabbed and processed by the microcontroller's software, the microcontroller may decide to change the video threshold to get a better image, which is done by writing to the data latch U18, which is enabled only by writing to address 2804 hex, this address being decoded internally by the image processor, which outputs the signal _DAEN, which is active high (should be called DAEN), leading to the latch U18 pin 11. The D/A combination eventually reaches the CCD Board, changing the threshold.

The microcontroller also checks for image centering and indicates correct positioning by an audible tone. Once stable readings are read, the microcontroller takes measurement, which means turning OFF the mire rings and peripheral projection LEDs, and turning ON only the four central projection LEDs, all of the above operations are done by modifying the content of the shift register U7,U6,U5. Now the last image is grabbed. Its content is processed and the desired cornea parameters are calculated and displayed on the LCD. At the program's discretion, several such measurements can be taken, to average out errors. The microcontroller returns to keyboard polling routine until another key depression is read, or, if none for a few moments, return to sleep mode.

4. Other Operations

By now, the reader is familiar with the principle of operation of the circuit. Generally, the microcontroller uses its data/address bus to access the EPROM for program instructions, the image processor for commands, status, and RAM reading, and using a serial port, it can modify the setting of any LED, the LCD, the speaker, and read the keyboard. The actual sequence of any operation is thus similar to the processes described above, wherein the microcontroller, under program control, accesses the desired device.

F.

Image Processing Algorithm

1. Introduction

The image processor circuit is implemented into a single field programmable gate array device. It contains three main parts: The micro controller interface, the CCD Imager timing generator, and an image processor. This document describes the algorithm that is implemented as part of the image processor device that processes the data scanned by the CCD imager located at the top of the ~~Lensometer~~ *Keratometer*.

2. High Level Description

The CCD imager can scan an entire picture that contains two fields: the first field contains all the odd lines, while the second field contains the even lines of the picture. The micro controller commands the image processor whether to select only one field or an entire picture (two fields) for every required measurement. The role of the image processor is to process the whole picture (or frame) in real time, to identify the light spots locations as sensed by the CCD camera and to fill a memory with the accurate XY coordinates and size of these light spots. After the measurement, the micro controller can read the captured samples from the memory and analyze the required parameters using these coordinates. The image processing algorithm can be described as a multiple stage sequential process, each stage in the process performs one operation on the serial data received from the previous stage. The process is described in the enclosed block diagram.

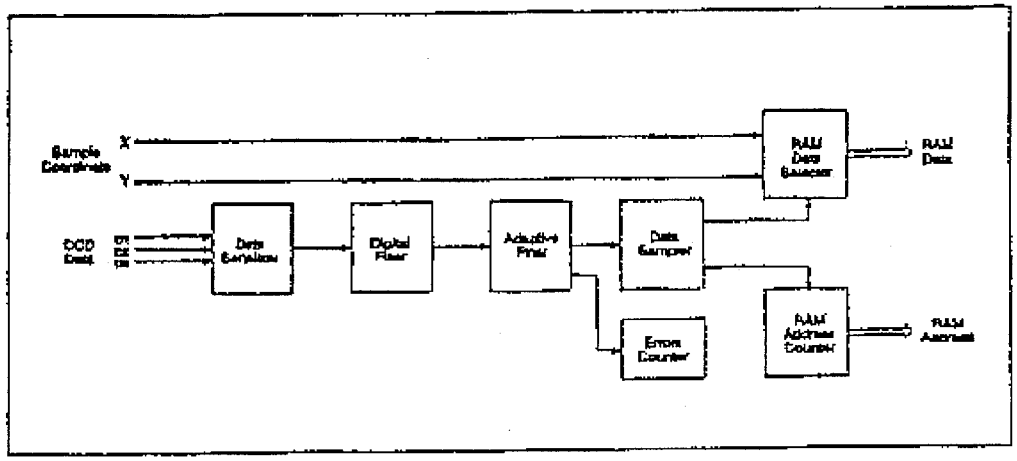

Diagram 1: Image Processing Algorithm Block Diagram

3.  Image Memory Map

The processed data is written by the image processor into a Random Access Memory (RAM) according to identified events in the data stream. An event is defined as a single light spot that includes the transition from dark to light and then from light to dark. These transitions are sampled after the data has been filtered through the digital filter, and the adaptive filter (explained later). The memory is arranged in groups of six bytes, each group describes one event and defined as follows:

| Byte in Group | Mnemonics | Description |
|---|---|---|
| 0 | XAH | Start of light, high byte |
| 1 | XAL | Start of light, low byte |
| 2 | YH | Row Number, high byte |
| 3 | YL | Row Number, low byte |
| 4 | XBH | End of light, high byte |
| 5 | XBL | End of light, low byte |

Table 1: Image Memory Content

Since the picture is scanned in rows, every event will start and end on the same row, a complete light spot will usually be spread over a few lines and represented by more than one group in the memory.

4. Input Data Structure

The input data is received by the image processor as 3 serial lines sent from the imager board (C1, C2, and C3 in the block diagram). These data lines contain serial data multiplexed between the three lines as shown in diagram 2.

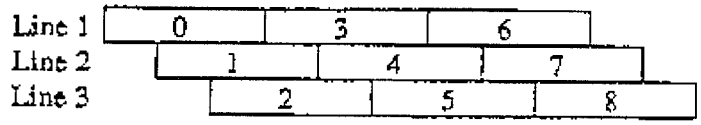

Diagram 2: Input Data Structure

The data from the imager is already digitized as explained in the circuit description of the CCD Imager board. If a 1 is found it means that the point had light in it, if it was 0, it means that there was no light at that point.

5. Serializing the data stream

The first operation of the image processor is to combine the three input data lines into a single serial data stream. The serializer samples the three input lines in a cyclic order (as shown in figure 2) while synchronizing the sampling with the clocks that are sent to shift data from the imager.

6. Digital Filter Stage

The digital filter process the data stream while searching for a single bit elements that represent noise, or un-smooth transition between light and dark. The digital filter always delays the data stream, and "looks" at the content of three consecutive data bits. If during a logic 0 stream, the data changes to 1, the digital filter checks the next data bit, if it is 0, then the first 1 is considered to be noise and replaced with a 0. If the next bit is also 1, it means that this is a level change, and the first bit is not changed. The following table shows all the possible cases of 3 consecutive bits and how they are processed by the digital filter (the left bit is the first to enter the filter):

| Input | Output | Comments |
|-------|--------|----------|
| 000 | 000 | Stream of 0, no change |
| 001 | 001 | Beginning of transition to 1, or noise, have to wait for next bit |
| 010 | 000 | Noise of 1 in a stream of 0 |
| 011 | 011 | Normal 0 to 1 transition |
| 100 | 100 | Normal 1 to 0 transition |
| 101 | 111 | Noise of 0 in a stream of 1 |
| 110 | 110 | Beginning of transition to 0 or noise, have to wait for next bit. |
| 111 | 111 | Stream of 1, no change |

Table 2: Digital Filter Transfer Function

7. Adaptive Filter

The adaptive filter is the next stage after the digital filter. According to the memory description above, when an event is identified, there are 4 write cycles to the memory on the dark to light transition (the first 4 locations), and then two more write cycles for the transition from light to dark, which brings the total of memory write cycles for every event to 6. The shortest event that is allowed after the digital filter contains 2 light bits, the next event can only occur after 2 dark bits, it means that in a the extreme case of repeating consecutive 2 bits of light followed by 2 bits of dark, we have only 4 bit slots available for each event. The memory write cycle takes the same time as a single bit, which means that in this extreme case, the information can not be written accurately to the memory without loosing information. Under normal circumstances, the distance between light sources is known and much larger than two bits, and this situation is not supposed to happen. In order to cover an extreme case like the one described above the adaptive filter is constantly monitoring the data stream to check whether there will be enough time to write all the information without loosing anything.

If the adaptive filter finds a violation that will not allow 6 memory cycles for an event, it will slightly change the bits in the sequence to follow the 6 bit cells rule. The design also contains a 2 bit error counter associated with the adaptive filter (shown in figure 1). When there is a violation of the 6 bit cell rule, and the adaptive filter have to change a data bit it also increments the content of the error counter. This counter is designed to be cleared at the beginning of the measurement, and when the counter reaches 3 which is the maximum possible value for a 2 bits counter, it stays as 3. After the completion of a measurement, the content of the error counter is available to the micro controller, if the value is not 0, the controller knows that a violation occurred. As said above under normal circumstances this correction is never activated and the violation can occur under extreme noise or during a threshold adjustments.

8. The Data Sampler

The data sampler is responsible for the sampling of the data, incrementing the memory address counter, and selecting the source of data (X and Y coordinates) to be written to the memory. The sampler is "looking" at the data stream after the adaptive filter which ensures that there is always time for at least 6 cycles of memory writes.

The following is a more detailed sequence of event performed by the sampling process:

Wait for transition from dark to light.
    When found:
        Write X address high byte (and increment memory address)
        Write X address low byte (and increment memory address)
        Write Y address high byte Write Y address low byte
Wait for transition from light to dark
    When found:
        Write X address high byte (and increment memory address)
        Write X address low byte (and increment memory address)
Check if address is at the maximum allowed,
    if not: start again,
    if end of memory: stop sampling.

G. IMAGE PROCESSOR DESCRIPTION

1. INTRODUCTION

1.1. General and Scope

The image processor is designed using a field programmable gate array. The design technique is very similar to a regular logic design using schematic entry, simulation, and then compilation and programming into the device. The image processor of the Keratometer contains three basic parts: the micro controller interface, the CCD timing generator and the image processing circuit. This document contains a description that gives the user a general understanding of the functionality of the device.

1.2. Schematics Organization (Figs. 35-38)

This description relies on 4 basic schematic pages, the top level that contains three main blocks designated as: MICRO (Fig. 36), CCD_CONT (Fig. 37 and IMAGE Fig. 38. Each of these blocks represents the level of details that is described according to the scope of this document.

2. MICRO CONTROLLER INTERFACE SECTION

The micro controller interface is responsible for the address decoding, latching the lower byte of the micro controller data bus, and interfacing the data and address between the micro controller and the memory.

2.1. Address Decoder (ADDECODE Block)

The address decoder serves the whole Keratometer circuit and not just the image processor, it decodes all the addresses that are part of the memory map of the micro controller. The functions that are addressed are as follows:
* The program memory (EPROM) which contains the program to run the micro controller.
* The Random Access Memory (RAM) that stores operational variables needed by the micro controller and the image processing results, also referred as the Image RAM.
* The digital to analog convertor, used as threshold for the CCD Image Processor.
* The command register, internal to this image processor which controls the operational modes of the image processor.
* The Image Processor status read, a register that provides status results of the image process.

2.2. Image Processor Command Registers (REG Block)

When the micro controller writes to this register, the measurement operation begins with the parameters that are loaded at the same time. The micro controller can set the following operational parameters: frame size to be scanned (wide or narrow), whether only one field is scanned or a complete frame, whether it is a normal measurement or a factory calibration, invert the light and dark signals (if inverted then the meaning of light and dark is swapped).

2.3. Micro Controller Data Selector (DSEL and CDBUF Blocks)

The micro controller data selector allows the controller to read/write data in a few modes. During normal operation when a measurement is not activated, the micro controller can use the RAM through the image processor and the image processor is basically disabled. Under specific status READ command, the selector provides the status information to the micro controller on the data bus. During the short period of measurement time, i.e. image grabbing, the micro controller data bus is disabled to allow the image processor to write to the RAM and to load the status registers without interruption.

2.4. RAM Data Selector (MDSEL and MDBUF Blocks)

The RAM can be read or written by the micro processor when a measurement is not active, at that time the RAM data bus is connected to the micro controller whenever the RAM is accessed. During measurement, the micro processor path is disabled and the image processor drives the coordinates of the light spots identified into the RAM, the X and Y counters are routed to the RAM data bus as needed by the process algorithm. (described in details as part of the image processing algorithm document)

2.5. RAM Address Selector (RASEL Block)

The RAM address selector similarly to the RAM data is connected to the micro controller as long as measurement is not active. During measurement, the image processor's address counter is connected to the RAM to allow incrementing address as needed by the image processing algorithm.

2.6. Low Address Byte Latch (LATCH block)

The latch receives the address / data bus and using the AS micro controller line to latch the lower byte of the address at the right time.

3. CCD TIMING GENERATOR SECTION

The CCD timing generator provides all the timing signals needed by the CCD imager, the generator contains the main X and Y counters for the image scanning, the main state machine that controls the whole scanning cycle, and three generators for the basic drive signals required by the CCD.

3.1. Main Counter (MAIN_CNT Block)

The main counter provides the horizontal count of the sampling points within every row, the counter provides the 786 sampling points and other taps that controls operations in the CCD. The counter contains also a Y counter of 244 odd or even lines (total of 288 lines). During the capture process of the picture, the event sampler uses these values of X and Y to store in the RAM as the coordinates of the event.

3.2. State Machine (STATES block)

The state machine controls the sequence of event during a measurement cycle. from the beginning of the operation, the state machine goes through 'priming' process of the CCD Imager and then through the scanning of all the even and odd lines of the picture. The state machine receives signals from the main counter indicating the end of scanning and changes its state according to the odd, even or other service cycles required by the CCD.

3.3. Vertical Signals Generator (VERT_GEN block)

The vertical signals are required after every field of 244 lines that is scanned, this block is responsible to generate the required timing for the odd or even vertical signals to allow proper operation of the CCD.

3.4. Horizontal Region 1 generator (H1_GEN)

Every line that is scanned in the CCD is required to have special signals at the beginning of the horizontal scan before the picture is available at the outputs of the CCD. This block generates the first 31 samples (first region) of every scan that are actually not seen as part of the picture to allow proper operation of the rest of the picture.

3.5. Horizontal Region 2 generator (H2_GEN)

The second region generator is responsible to 'push' the picture out of the CCD, it provides the exact number of pulses required to receive one line of the picture.

3.6. CCD Timing Selector (V_H_SEL block)

The CCD timing selector is responsible for selecting which of the above generated 3 signals should be sent at any time to the CCD. The decision is made by the state machine that controls a set of selectors that route the appropriate generated signals to the CCD. The result is the actual lines that are sent to the CCD drivers.

4. IMAGE PROCESSING SECTION

This section of the image processor covers the actual image processing, for further understanding of the image process algorithm, it is recommended to read the Image Processing Algorithm document. This section contains the processing control, the event processing, the X value latch, and the image counter. There are two blocks that were used to accumulate the X and Y values called SIGMAX and SIG_Y that appears in the schematics but are not used.

4.1. Image Processing Control (HOR_SCAN block)

This block is responsible for the actual picture capture, it evaluates the requirements that are loaded by the micro controller whether to sample a single frame or the whole picture, and the actual frame size, and then enables the data to flow to the event processor. This block also supports the increments of the memory counter as required. When the measurement operation is completed this block flags the micro controller that the operation is complete.

4.2. Events Processing (EVENT block)

The event processing block is divided to three consecutive sub blocks: the digital filter, adaptive filter and the sampler. The operation of these blocks is described in details as part of the image processing algorithm document.

4.3. The X Latch (X_LATCH block)

The X latch is used to hold the value of the x coordinate counter to ensure a stable writing to the memory while the picture is processed. The latching of the X value is required since the write operation to the memory requires two consecutive write operations, and the second part of the written X is kept to prevent corruption of the value.

4.4. Image Counter (IMADCNTR block)

The image counter is responsible to generate the address to the RAM while the picture is processed. At the end of the process the counter keeps the last address that was used and the controller can read this value and use it to know how many events were processed during that cycle.

H. Software Theory of Operation

The following is a description of the software operation of the preferred embodiment of the invention. Reference should be taken to the flowchart at Figs. 16A-16B, Figs. 34A-34B, as well as the other Figures and description regarding the preferred embodiment.

I. Preface
   A. Keratometry in General *hand-held*
      The function of the ~~Metaphase hand-held~~ Keratometer is to measure the radius of curvature of a patient's cornea quickly and accurately. This curvature is calculated along two orthogonal meridians. The results can be expressed as corneal powers (units of diopters - abbreviation Dk), or radii of curvature (units of milli-meters).

B. Our Method
      The Keratometer uses four equally-spaced light sources which project collimated light onto a patient's eye. The light is reflected off of the eye and imaged, as spots, onto a charge-coupled imaging device, or CCD. The scan data is then digitized, run-length encoded, and stored in a memory buffer. A microprocessor evaluates the data. Each run is grouped according to proximity to recreate the four spots. The center of each spot is calculated by averaging the position and length data of all runs in a group.

The basic computation uses three spots. The radii of curvature are calculated using the positions of three measured spots with respect to a set of known reference positions. Our implementation uses the positions of all four spots to create three "synthetic" spots. The "synthetic" spots are then used in the three-spot calculations.

II. Hardware/Software Interface
   A. Micro-controller
      1. General
         The software runs on a Motorola 68HC11E1 8-bit micro-controller unit (MCU). The HC11 is a high-density CMOS component with sophisticated on-chip peripheral capabilities. These features include:

-> Serial Peripheral Interface (SPI)
         -> Asynchronous Serial Communications Interface (SCI)
         -> 512 bytes of EEPROM
         -> 512 bytes of static RAM
         -> Eight-channel, 8-bit Analog/Digital converter
         -> Real-time interrupt circuit
         -> Enhanced 16-bit timer system
         -> Power-saving STOP and WAIT modes
         -> Small 52-pin plastic leaded chip carrier (PLCC)
         -> 2 Mhz Bus speed
         -> 64 Kbyte linear address range
         -> Full instruction set We operate the 68HC11 in expanded mode, using its external EPROM and scratch-pad memory.

2. Pin Usage

The functions of the HC11 I/O pins are:

| Pin | I/O | DES I/O | Name | Description |
|-----|-----|---------|------|-------------|
| PA0 | Input | not used | N.A. | Pulled LOW via 10K resistor |
| PA1 | Input | | _PRINT | Signal from base |
| PA2 | Input | | _BUSY:LCD8 | Busy line from LCD controllers |
| PA3 | I/O | Output | SEL0:LCD5 | Peripheral select line |
| PA4 | Output | | SEL1:LCD6 | Peripheral select line |
| PA5 | Output | | SEL2:LCD7 | Peripheral select line |
| PA6 | Output | | PWM:LCD4 | LED PWM signal |
| PA7 | I/O | Output | _SLEEP | Power supply on/off |
| Pbx | N.A. | | [[[ Upper address byte in expanded mode ]]] | |
| PCx | N.A. | | [[[ Multiplexed address/data lines in expanded mode ]]] | |
| PD0 | I/O | Input | RxD | SCI: receive data |
| PD1 | I/O | Output | TxD | SCI: transmit data |
| PD2 | I/O | Input | MISO:LCD0 | SPI: master-in slave-out |
| PD3 | I/O | Output | MOSI:LCD1 | SPI: master-out slave-in |
| PD4 | I/O | Output | SCK:LCD2 | SPI: serial clock |
| PD5 | I/O | Output | SS:LCD3 | SPI: slave select |
| PE0 | A. Input | A. Input | P12V | Plus 12V supply test |
| PE1 | A. Input | A. Input | P1V5 | Plus 1.5V supply test |
| PE2 | A. Input | A. Input | N7V | Minus 7.0V supply test |
| PE3 | A. Input | A. Input | N9V5 | Minus 9.5V supply test |
| PE4 | A. Input | A. Input | BASE | Monitor when in base |
| PE5 | A. Input | A. Input | VBAT | Battery voltage test |
| PE6 | A. Input | not used | N.A. | Pulled to ground via 10K |
| PE7 | A. Input | not used | N.A. | Pulled to ground via 10K |

Note: PA3 is an output-only pin on the 68HC11A1/A8 part.

3. Memory Map
   The memory is mapped as:

| Description | Range | Bytes | Notes |
| --- | --- | --- | --- |
| Internal RAM | 0000 - 01FF | 512 | details below |
| Unused | 0200 - 0FFF | 3584 | |
| 68HC11 Registers | 1000 - 103F | 64 | |
| Unused | 1040 - 1FFF | 4032 | |
| RAM | 2000 - 27FF | 2048 | 4 overlapping pages, details below |
| Unused | 2800 - 3FFF | 6144 | |
| IP Registers | 4000 - 4FFF | 4096 | redundant mapping |
| Unused | 5000 - 7FFF | 12288 | |
| EPROM | 8000 - B5FF | 13824 | |
| EEPROM | B600 - B7FF | 512 | details below |
| EPROM | B800 - FFFF | 18432 | |
| | 0000 - FFFF | 65536 | |

| Internal RAM | Range | Bytes | Notes |
| --- | --- | --- | --- |
| MATH11 FP regs | 0000 - 0009 | 10 | floating point accumulators for math11 |
| *.S07 local vars | 000A - 005F | 86 | assembly routines local variable space |
| HC11 RAM vars | 0060 - 006F | 16 | non-volatile non-paged memory |
| Unused | 0070 - 00FF | 144 | spare direct-access memory |
| Unused | 0100 - 017F | 128 | spare extended-access memory |
| Stack Space | 0180 - 01FF | 128 | program stack area |
| | 0000 - 01FF | 512 | |

| EEPROM | Range | Bytes | Notes |
| --- | --- | --- | --- |
| CC vars | B600 - B64F | 80 | camera calibration parms in REAL format |
| SC vars | B650 - B67C | 45 | spot calibration parms in REAL format |
| DA vars | B67D - B6E5 | 105 | pre-calculated values in REAL format |
| PR vars | B6E6 - B715 | 48 | parameter record - operational data |
| Unused | B716 - B7FE | 233 | |
| Checksum | B7FF - B7FF | 1 | EEPROM checksum |
| | B600 - B7FF | 512 | |

B. Memory
   1. EPROM
      a. Overview
      Program memory resides in a 27C256 one-time programmable (OTP) PROM. The device provides 32 Kbytes of program storage and comes in a 32-pin PLCC package.

b. Software Interface
      The program memory address range is 8000 to FFFF hex. The exception vector table, or interrupt vector table, is located from address FFD6 to FFFF hex, per MCU specifications. The 16-bit checksum for this device is at address 8000:8001. Addresses B600 thru B7FF hex are unavailable due to conflicts with the MCU internal EEPROM.

2. RAM
      a. Overview
      The RAM is composed of four 2 Kbyte sections, or pages. Each page resides at addresses 2000 to 27FF hex.

b. Software Interface
      Each page has a designated use:

| page # | usage |
      | --- | --- |
      | 0 | General variable storage |
      | 1 | Communication routines messages |
      | 2 | Video data page 1 |
      | 3 | Video data page 2 |

The lower two bits of the image processor register RAM_CONFIG_REGISTER (00/01/10/11 binary) determines which of four pages is accessed. The routine SwitchToPage() in file PAGE.S07 does the page switches.

To select page #1:  SwitchToPage(1);
      To select page #3:  SwitchToPage(3);

The subroutine Fifo2CMT() in FIFO2CMT.S07 circumvents this procedure by writing directly to the page register. This exception increases the instrument measurement speed.

3. EEPROM a. Overview

The HC11 has 512 bytes of on-board non-volatile EEPROM. To program the EEPROM, the software writes out 10 hex to the block protect (BPROT) register within 64 cycles of reset.

b. Software Interface

The EEPROM memory is used to store calibration parameters, operational modes and user options. The routine ProgramEEPROMByte() in file ASM.S07 does the actual programming. Examples:

```
Write data 3C hex to B634:  ProgramEEPROMByte(0xB634, 0x3C);
Write data F5 hex to B701:  ProgramEEPROMByte(0xB701, 0xF5);
```

The MCU can only program bits from ones to zeros. To change a bit from zero to one, the entire byte must first be erased (all bits set to one), then reprogrammed. Since the EEPROM has limited life, the routine checks the currently stored data against the data to program. If the data-to-write 1) equals the data already there, nothing is done, or 2) involves only programming more zeros, the byte is programmed, or 3) requires any bit to change from a zero to a one, the byte is erased and reprogrammed.

An 8-bit checksum of the EEPROM is stored in address B7FF hex. The routine ChecksumEEPROM() in TESTING.S07, calculates the checksum. The routine CommitToEEPROM() in MISC.C, stores the current checksum.

-> Camera calibration

The camera calibration parameters which characterize the optical system, are stored in the 68HC11 EEPROM during instrument manufacture. The parameters are:

xp,yp,f,l1,l2,l3,p1,p2,p3,z,xc,yc,zc,omega,kappa,phi

They are referenced by the data structure defined in CC.H.

-> Spot calibration

The spot calibration values are also stored in the 68HC11 EEPROM during instrument manufacture. These values represent the spot positions obtained by projecting the red LED's onto a known power surface and recording spot positions. The data set also contains the diopter power of the calibration lens/ball. Items are:

| | |
|---|---|
| dkCalBall | : Calibration power |
| vi[0].hor,vi[0].ver | : Spot 1 position |
| vi[1].hor,vi[1].ver | : Spot 2 position |
| vi[2].hor,vi[2].ver | : Spot 3 position |
| vi[3].hor,vi[3].ver | : Spot 4 position |

They are referenced by the data structure defined in SC.H.

-> Pre-calculated values

Some terms of the computation depend only on the calibration values. To save processing time, these terms are pre-calculated and stored in the 68HC11 EEPROM. The terms are:

m11,m12,m13,m21,m22,m23,m31,m32,m33,m13z,m23z,m33z,
x2b,y2b,x3b,y3b,twoA,fourA,quadZero,threshFactor,nonTorricVal They are referenced by the data structure defined in DA.H.

-> Operational values

These values include various functions, from user selectable operational modes to reference angles and execution values. The values are stored in EEPROM in a data structure defined in PR.H. During operation the values are used in the RAM structure MO.H.

C. Imaging System
 1. Imager

Our imager is a charged-coupled device (CCD) from Texas Instruments, part number TI-245. The optical area measures 8.0 mm diagonally; 6.4175 mm wide by 4.7795 mm high. The optical area is divided into 755 columns by 484 rows. Physically there are 242 rows of pixels, and electronic interpolation produces 484 effective rows. The interpolation provides two "fields": one even and the other odd. The fields are interleaved to make a frame. There is no space between pixels. The pixel size is 8.5 $\mu$m wide by 9.875 $\mu$m high (19.75 $\mu$m high, PHYSICAL pixel). Horizontally there are 117.6470588 pixels per mm, and vertically there are 101.2658228 pixels per mm.

CCD optical area:

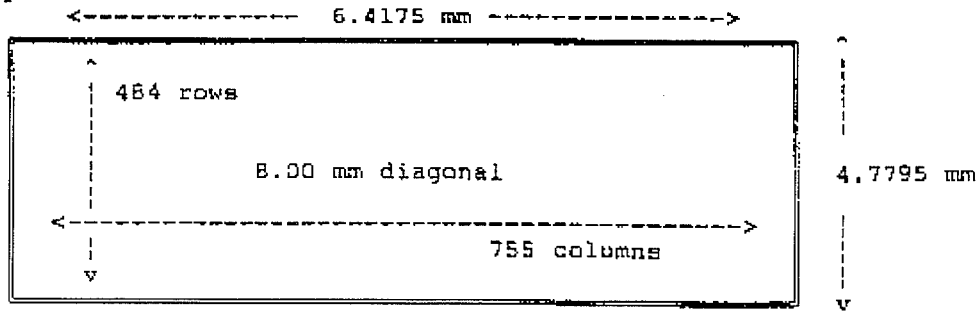

Pixel size:

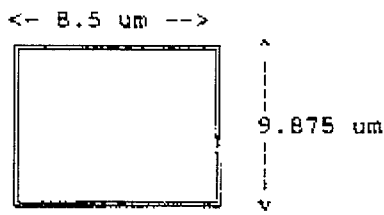

2. Image processor
a. Overview

Our image processor (IP) is implemented in an ACTEL A1020A ASIC (Application-Specific Integrated Circuit). It comes in a 68-pin PLCC package. The registers available to the MCU are:

COMMAND_REGISTER: (write-only; address = 4000 hex)

| bit | name | description |
| --- | --- | --- |
| 7 | IPRAM PAGE1 | Selects current RAM page |
| 6 | IPRAM PAGE0 | Selects current RAM page |
| 5 | PB (IP POWER) | IP power on(1)/off(0) |
| 4 | INVERT | Image(1)/normal image(0) |
| 3 | _RESET | Device reset(0)/normal operation(1) |
| 2 | FRM/FLD | Process frame(1)/process field(0) |
| 1 | FRM_SIZE1 | Enable processing of top of image(1) |
| 0 | FRM_SIZE0 | Enable processing of bottom of image(1) |

RAM_CONFIG_REGISTER: (write-only; address = 4002 hex)

| bit | name | description |
| --- | --- | --- |
| 2 | CALIB | Calibrate mode(1)/normal mode(0) |
| 1 | MPRAM PAGE1 | Selects fifo page to store video data |
| 0 | MPRAM PAGE0 | Selects fifo page to store video data |

STATUS_REGISTER: (read-only; address = 4000 hex)

| bit | name | description |
| --- | --- | --- |
| 7 | A3 | Last address of video data, |
| 6 | A2 | Lower four bits |
| 5 | A1 | Lower four bits |
| 4 | A0 | Lower four bits |
| 3 | unused | |
| 2 | ER1 | Error indicator bit |
| 1 | ER0 | Error indicator bit |
| 0 | CP | Command-pending(1) |

DAC_REGISTER: (write-only; address = 4004 hex)

| bit | name | description |
| --- | --- | --- |
| 7-0 | | input to D/A convertor, which is the image signal threshold voltage. |

LAST_ADDRESS: (read-only; address = 4003 hex)

| bit | name | description |
| --- | --- | --- |
| 7-0 | | last address, upper eight bits, combined with A3-A0 from above. |

After processing a video field or frame, video data entries reside in video page memory starting at address 2000 hex. The image processor computes the "last address plus 1" of the video data. The last address is twelve bits wide, and is composed of the LAST_ADDRESS register concatonated with bits A3-A0 of the STATUS_REGISTER.

Please note that the video data is also referred to as "fifo" data.

b. Software Interface

The files IMAGER.C and IMAGER.H contain drivers for the image processor. The routine GetFifo() commands the IP to take a field or frame of data, waits for the completion of the task, and retrieves the last address and error bits. The procedure DoubleFifoBurst() does the same thing, but it takes two successive images, increasing measurement through-put. Examples:

Take an image during measurement process and put the data into page 1:
   GetFifo(MEASURING, FIFO1_PAGE);

Take a burst of two images during measurement:
    DoubleFifoBurst();

3. D/A Converter
  a. Overview
    The imaging system has a variable threshold using an 8-bit DAC IC. Higher digital values increase the threshold so that more light is needed to turn a pixel "on". Lowering the digital input lowers the threshold.

b. Software Interface
    The routine SetImagerThreshold() in files DRIVERS.C & DRIVERS.H sets the DAC value. When measuring eyes, the first two values of the mo.dacValue array are used; when measuring steel balls, the last two values of the mo.dacValue array are used.

D. Serial Peripheral Interface (SPI)
  The eight signals which comprise the Synchronous Serial Interface (SPI) system include (refer to paragraph II.A.2):

| | |
  |---|---|
  | MISO | : master-in slave-out data line |
  | MOSI | : master-out slave-in data line |
  | SCK | : serial clock |
  | SS | : command/_data signal to LCD drivers (uPD7225) |
  | SEL2 | : select lines to enable particular device, |
  | SEL1 | : e.g. LCD drivers, keypad shift register, or |
  | SEL0 | : RCLK of 8-bit serial/parallel shifters |
  | _BUSY | : busy indicator from LCD drivers |

The SEL2:SEL1:SEL0 lines select which device is accessed via a 3-to-8 decoder 74HC138 (U3). The SS line indicates to the LCD drivers whether the incoming data is a command or raw data. The LCD drivers accept the data, and hold _BUSY low until they are ready for another byte. The keypad is read via a 74HC165 parallel-to-serial shift register (U4). The three 74HC595 serial-to-parallel shift registers (U5/U6/U7) control the projector, alignment, fixation LED's, level LED's, mire, backlight, speaker, LCD contrast, LCD driver reset, and calibration RAM pointer reset.

The files DRIVERS.C & DRIVERS.H contain the keypad and 74HC595 driver routines. The general purpose routine, ShiftOutDriver, controls the 74HC595 shift registers. The low level LCD drivers are in LCD.C & LCD.H, and the high level display drivers are in DISPLAY.C & DISPLAY.H.

1. LCD Display
   a. Overview
   The LCD display is composed of 165 segments including 19 seven-segment numbers and 32 individual icons. The drivers are configured as a master/slave combination of NEC UPD7225 ICs (U1 and U2). Each segment is individually controlled, and can blink at either of two rates.

Segment Identification:    Segment COM Connections:
                              (quadruplexed)

Controller RAM allocation for each segment:

n+1: d:e:g:f
   n:   dp:c:b:a

Four outputs of shift register U7 control the contrast of the LCD segments. All outputs set to ones gives maximum contrast.

For further information, refer to NEC UPD72 Intelligent AlphaNumberic LCC Controller/Driver Technical Manual (stock # 500250), and NEC UPD7225 Application Note (stock # 501102).

b. Software Interface
   The low level drivers for the LCD are in files LCD.C & LCD.H. The procedure Icons() controls the 32 individual icons, and the procedure Digits() controls the seven-segment numbers. The icons are all single-segment items, such as the display units (Dk/mm), the display format (sphere/cylinder/base curves), and the angle reference (ground/handle). Examples:

Turn the "Dk" icon on:     Icon(ICON_DK, LCD_STEADY);
   Turn the "mm" icon off:    Icon(ICON_MM, LCD_ALL_OFF);
   Flash the "+" icon:        Icon(ICON_PLUS, LCD_FLASHING);

The 19 digits are numbered left to right, top to bottom. Examples:

Put a "1" in location #15:   Digit(DIGIT_15, '1', LCD_DR_ON);
   Put a blank in location #3:  Digit(DIGIT_3, ' ', LCD_STEADY);

To display a complete numerical value, call DisplayNumber(). Examples:

Display 42.57 in group 1 (top left):
   DisplayNumber(DIGIT_GROUP_1, 42.57, LCD_DR_ON, TRUE);
Display 123 in group 5 (degrees place):
   DisplayNumber(DIGIT_GROUP_5, 123.0, LCD_DR_ON, TRUE);

The high level display driver, Display() is in files DISPLAY.C & DISPLAY.H. The function displays a particular set of segments based on the current operating mode and results. Examples:

Display current reference angle status:
   Display(D_ANGLE_REF);
Display current results format:
   Display(D_RESULTS_FORMAT);

The contrast is adjustable from 0 (no contrast) through 15 (maximum contrast). Example:

Set contrast to 7: SetLCDContrast(7);

2. Projector LED's
   a. Overview
      The four red projector LED's are controlled via a single line (QA) from shift register U5.

b. Software Interface
      Examples:

Turn projectors on: ShiftOutDriver(SO_MEAS_LEDs, ON);
      Turn them off:      ShiftOutDriver(SO_MEAS_LEDs, OFF);

3. Alignment LED's
   a. Overview
      The eight green alignment LED's help the operator align the instrument during measurement. These are controlled by a single line (QB) from shift register U5.

b. Software Interface
      Examples:

Turn alignment on:  ShiftOutDriver(SO_ALIGN_LEDS, ON);
      Turn them off:      ShiftOutDriver(SO_ALIGN_LEDS, OFF);

4. Fixation LED's
   a. Overview
   The five fixation LED's: center, top, bottom, left and right, give the patient a point to fixate on while a measurement is being taken. Each fixation LED is individually controlled via outputs QA through QE of shift register U6.

b. Software Interface
   Examples:

Turn center fixation on:   ShiftOutDriver(SO_CENTER_FIX_LED, ON);
   Turn top fixation off:     ShiftOutDriver(SO_TOP_FIX_LED, OFF);

5. Mire
   a. Overview
   The mire is composed of a ring of red LED's including the top, bottom, left and right fixation LED's. Together these form a complete circle which is projected onto the patients eye just prior to the measurement. The mire allows the operator to visually inspect the surface of the eye for abnormalities. Mire control is provided via pins QA, QB, QC, and QD of U6.

b. Software Interface
   The high level function TurnMire() controls the LED's. Examples:

Turn mire on:    TurnMire(ON);
   Turn mire off:   TurnMire(OFF);

6. Speaker
   a. Overview
   The beeper is a piezo-electric speaker driven by a LM555 timer. The timer has two control lines: one controls the pitch, the other is an on/off switch (U7 pin QE).

b. Software Interface
   The high level function Speaker() controls the beeper. Examples:

Turn speaker on high pitch:   Speaker(SPKR_HIGH);
   Turn speaker off:             Speaker(SPKR_OFF);

7. Level LED's
   a. Overview
   The level LED's light a device used to determine the angle of the instrument with respect to ground. The LED's shine through a liquid which is imaged as a line on the CCD. The MCU calculates the slope of this line and hence the angle of the instrument. The level LED's are controlled by a single output line (QF) on shift register U6.

b. Software Interface
The high level function ReadLevelAngle() in file MEASURE.C turns on the level LED's, commands the image processor to collect the data, and calls ProcessLevelFifo() which calculates the angle. ProcessLevelFifo(), in file LEVEL.S07, uses two "points" to compute the slope. The two points are averages of 16 samples taken at the beginning and end of the image data.

8. Backlight
 a. Overview
  The backlight is an array of yellow LED's which illuminate the LCD to improve readability. The backlight is controlled by output pin (QG) on register U6.

b. Software Interface
  Examples:

Turn backlight on:  ShiftOutDrivers(SO_BACKLIGHT, ON);
  Turn backlight off: ShiftOutDrivers(SO_BACKLIGHT, OFF);

9. Keypad
 a. Overview
  The keypad has six keys: SELECT, SCROLL, CLEAR, RIGHT_EYE, LEFT_EYE, and MEASURE. Key closure is determined by polling the 74HC165 (U4) register.

b. Software Interface
  The low level keypad driver ReadKeyboard() returns the current status of the keypad sense lines. The high level routine CheckKeyboard() monitors key press, debounce, and release. Upon release, it makes a key "click" sound. CheckKeyboard interprets pressing the MEASURE key as an ALIGN_KEY_EVENT and turns on the mire. CheckKeyboard interprets release of the MEASURE key as a MEASURE_KEY_EVENT and begins the measurement process.

10. Reset Lines
 a. Overview
  The LCD drivers can be reset by pulling line (QG) of U7 low. The calibration RAM pointer is reset in the same manner by (QH) of U7.

b. Software Interface
  Examples:

Reset LCD drivers:     ResetLCD();
  Reset cal RAM pointer: ResetCalRAMPointer();

E. Serial Communications Interface (SCI)
  1. Overview
    The two signals which comprise the SCI system are (refer to paragraph II.A.2):

RxD : Receive data line into MCU
    TxD : Transmit data line out of MCU

This interface outputs a ticket to the printer and communicates with the field test terminal/engineering test software, or the ~~Metaphase~~-PC system.

2. Software Interface
    The low level asynchronous communication module in files COMM.C & COMM.H formats, receives, transmits, and extracts messages to/from the PC and sends ticket information to the system printer.

The high level driver which communicates with the PC resides in PCCOMM.C and PCCOMM.H. In PC-to-MCU mode, the PC initiates all communications with an ENQuire byte, then waits for the MCU to respond with an ACKnowlegde byte. The PC then sends a command and data (if any), and waits for the MCU to return a response and data (if any).

F. Calibration Module
    During camera calibration, the Keratometer must store much more data than in normal operation. A calibration RAM module is used for this purpose. This module provides 32 Kbytes of RAM storage for the fifo. The module is accessed sequentially, not randomly.

To start the process, the calibration RAM pointer is reset by the ResetCALRAMPointer ( ) routine. Then the IP stores a frame of data in the RAM module. After the pointer is reset again, the data is retrieved by reading address 2000 hex. A write to address 2000 hex increments the address pointer, the process is repeated until all fifo data has been read.

III. Software Organization
  A. Vendor Packages
    1. Archimedes C-compiler, assembler, linker and librarian
    2. Sage Software Polymake dependency generator and make facility
    3. NOHAU EMUL-68 emulator control package
  B. File Descriptions
    1. C source files, *.C
       aa) BORDER    : defines active useful area on imager
       ab) CALIBRAT  : control camera calibration functions
       ac) CM        : declare center of mass data
       ad) COMM      : low level asynch serial communication module

| | | |
|---|---|---|
| ae) DISPLAY | : | high level LCD display drivers |
| af) DRIVERS | : | low level device drivers |
| ag) DUMP | : | dumps test data out of the comm port |
| ah) ERROR | : | handles system errors |
| ai) FIELDTST | : | controls field test terminal |
| aj) GETPUT | : | C procedures getchar() and putchar() |
| ak) GL | : | global data declaration |
| al) HIDDEN | : | options hidden from normal user |
| am) II | : | instrument info; copyright and date |
| an) IMAGER | : | low level image processor driver |
| ao) INIT | : | initialization and startup routines |
| ap) LCD | : | low level LCD driver |
| aq) MAIN | : | main program control module |
| ar) MEASURE | : | controls the measurement process |
| as) MISC | : | miscellaneous subroutines |
| at) MO | : | mode variables; a copy of EEPROM pr structure |
| au) OPTIONS | : | user-selectable options |
| av) PCCOMM | : | PC serial communication interpreter/processor |
| aw) PRINT | : | prints tickets |
| ax) QU | : | results data declaration |
| ay) RE | : | results data declaration |
| az) RESULTS | : | handles storing/saving/loading/restoring results |
| ba) SELFTEST | : | hardware selftest routines |
| bb) THRSHOLD | : | thresholds signal; not used now |
| bc) VA | : | intermediate calculation variables data declaration |

2. C header files, *.H

| | | |
|---|---|---|
| aa) APPL | : | application-specific constant definitions |
| ab) ASCII | : | ASCII constants |
| ac) ASM | : | header |
| ad) BORDER | : | header |
| ae) CALC | : | header |
| af) CALIBRAT | : | header |
| ag) CC | : | camera calibration data definition |
| ah) CM | : | center-of-mass data definition |
| ai) COMM | : | header |
| aj) CONST | : | constants |
| ak) DA | : | pre-calculated values data definition |
| al) DASM | : | header |
| am) DISPLAY | : | header |
| an) DISTORT | : | header |
| ao) DRIVERS | : | header |
| ap) DUMP | : | header |
| aq) ERROR | : | header |
| ar) FIELDTST | : | header |

|               |              |                                                |
|---------------|--------------|------------------------------------------------|
| as) FIFO2CMT  | : header     |                                                |
| at) FILTERS   | : header     |                                                |
| au) GENERAL   | : system-wide header file                      |
| av) GETPUT    | : header     |                                                |
| aw) GL        | : global variables data definition             |
| ax) HC        | : 68HC11 RAM variables data definition         |
| ay) HIDDEN    | : header     |                                                |
| az) IDSPOTS   | : header     |                                                |
| ba) II        | : header     |                                                |
| bb) IMAGER    | : header     |                                                |
| bc) INIT      | : header     |                                                |
| bd) IO        | : system I/O definitions and addresses         |
| be) IO6811    | : 68HC11-specific register addresses           |
| bf) LCD       | : header     |                                                |
| bg) LEVEL     | : header     |                                                |
| bh) MAIN      | : header     |                                                |
| bi) MEASURE   | : header     |                                                |
| bj) MEMORY    | : header     |                                                |
| bk) MISC      | : header     |                                                |
| bl) MO        | : mode variables data definition               |
| bm) MOREASM   | : header     |                                                |
| bn) OPTIONS   | : header     |                                                |
| bo) PAGE      | : header     |                                                |
| bp) PAGE1     | : comm messages data definition                |
| bq) PCCOMM    | : header     |                                                |
| br) PR        | : parameter record data definition             |
| bs) PRINT     | : header     |                                                |
| bt) QU        | : que data definition                          |
| bu) QUEUE     | : header     |                                                |
| bv) RE        | : results data definition                      |
| bw) REAL      | : REAL type defintion                          |
| bx) REALCMS   | : header     |                                                |
| by) RESULTS   | : header     |                                                |
| bz) SC        | : spot calibration data definition             |
| ca) SELFTEST  | : header     |                                                |
| cb) TESTING   | : header     |                                                |
| cc) THRSHOLD  | : header     |                                                |
| cd) TOSSBAD   | : header     |                                                |
| ce) VA        | : intermediate calculation variables data definition |
| cf) VECTOR    | : header     |                                                |

3. Assembly source files, *.S07
    aa) ASM       : various assembly language routines, incl. GoToSleep()
    ab) CALC     : calculates base curves, axis, and torricity
    ac) CC        : camera calibration data declaration

| | | |
|---|---|---|
| ad) CONSTANT | : | definition of REAL constants |
| ae) CSTARTUP | : | C program start up and exception vector table |
| af) DA | : | pre-calculated data declaration |
| ag) DASM | : | various math-related subroutines |
| ah) DISTORT | : | converts image points to object points via lens correction |
| ai) FIFO2CMT | : | converts image data to center-of-mass table |
| aj) FILTERS | : | area, radius and power filters |
| ak) HC | : | 68HC11 RAM data declaration |
| al) IDSPOTS | : | identifies spots |
| am) LEVEL | : | determines level angle |
| an) MATH11 | : | FAST floating point math library obtained from Motorola BBS |
| ao) MEMORY | : | C procedures memcpy() and memset() |
| ap) MOREASM | : | formats results |
| aq) PAGE | : | switches RAM pages |
| ar) PAGE1 | : | comm messages data declaration |
| as) PR | : | parameter record data declaration |
| at) QUEUE | : | que handlers |
| au) REALCMS | : | converts pixel data to floating point centers-of-mass |
| av) SC | : | spot calibration data declaration |
| aw) TESTING | : | various self-test routines |
| ax) TOSSBAD | : | removes bad spots |

4. Assembly header files, *.INC

| | | |
|---|---|---|
| aa) 6811REGS | : | 68HC11-specific register addresses |
| ab) APPL | : | application-specific values |
| ac) CC | : | camera calibration data header |
| ad) CM | : | center-of-mass data header |
| ae) CONSTANT | : | REAL type constants header |
| af) DA | : | pre-calculated values data header |
| ag) DASM | : | header |
| ah) FIFO2CMT | : | header |
| ai) GL | : | global variables data header |
| aj) HC | : | 68HC11 RAM data header |
| ak) IO | : | system I/O definitions and addresses |
| al) MACROS | : | macro definitions |
| am) MATH11 | : | header |
| an) MO | : | mode variables data header |
| ao) MOREASM | : | header |
| ap) PAGE | : | RAM paging header |
| aq) QU | : | queue data header |
| ar) RE | : | results data header |
| as) REAL | : | REAL type data header |
| at) SC | : | spot calibration data header |
| au) VA | : | intermediate calculation variables data header |

5. Make files
   a. MAKEFILE.MAK
   This file controls the "make" or compile/assemble/link process. Typing MAKE <CR> at the DOS prompts executes the "MAKE". The code is generated and put in file MAIN.A07. It can then be downloaded into the NOHAU emulator. Typing MAKE EPROM <CR>, creates the output file EPROM.MOT, in the motorola S-record format accepted by an EPROM programmer. The "MAKE" file can also update the MAKEFILE.MAK dependency when the user types MAKE DEPS <CR> at the DOS prompt or 2) delete all *.BAK files and execute Norton's directory sort (DS) command to arrange the files when the user types MAKE CLEANUP <CR>.

b. BUILTINS.MAK
   This file tells Polymake how to invoke the Archimedes assembler/compiler and what options to use.

C. Main State Machine (Reference Figure 1)
   The main program control is handled in files MAIN.C and MAIN.H, a finite state table sequences the procedures. The STATES are:

SLEEP       : All power except MCU powers off, saves results in RAM.
   HOLD        : Results displayed on LCD, but turn backlight off,
   DISPLAY     : LCD display and backlight both on,
   THRESHOLD   : Thresholding algorithm (not currently implemented),
   MEASURE     : Make a measurement
   OPTIONS     : Select and scroll through the user selectable options,
   HIDDEN      : Select and scroll through the hidden options.

The EVENTS are:
1. Keypad entry events
   a.  NO_EVENT         : Nothing happened
   b.  SELECT_KEY       : Select key depressed
   c.  SCROLL_KEY       : Scroll key depressed
   d.  CLEAR_KEY        : Clear key depressed
   e.  RIGHT_EYE_KEY    : Right eye key depressed
   f.  LEFT_EYE_KEY     : Left eye key depressed
   g.  ALIGN_KEY        : Measure key depressed
   h.  MEASURE_KEY      : Measure key released
   i.  PRINT_KEY        : Print key depressed
2. Procedure return status
   a.  OK_FLAG          : Routine successfully executed
   b.  REPEAT_FLAG      : Routine needs to try again
   c.  FAILED_FLAG      : Routine failed
3. PC_MESSAGE           : PC sent an ENQuire byte
4. FIELD_TEST_TERMINAL  : Terminal sent a CR byte 5. TIMEOUT :No activity for prescribed amount of time Note that the measure key has two functions, one when pressed and another when released. The clear key has three functions. The first time it is pressed, the current results are cleared from the display. The second press clears all results. The third press puts the Keratometer into SLEEP mode.

IV. Measurement Process (reference Figure 2)
  A. Align Instrument
    1. Procedure
      a. Turn alignment LED's on
      b. Delay for 1.5 seconds
      c. Turn alignment LED's off
    2. Equations: NONE
    3. Data: NONE
    4. Source
      a. MEASURE.C
    5. Errors: NONE
  B. Take an Image
    1. Procedure
      a. Turn red projector LED's on
      b. Set first threshold (DAC)
      c. Command imager processor (IP) to take a frame of data
      d. Have IP store runs in image data page 1
      e. Read IP status bits and last address
      f. Set threshold value 2
      g. Command IP to take another frame of data
      h. Have IP store runs in image data page 2
      i. Read IP status bits and last address
    2. Equations: NONE
    3. Data
      a. RAM data
        The image data is run length encoded. Each run contains three pieces of information: beginning column (X), row (Y), and ending column + 1. Each item is two bytes long. Each page is 2048 bytes deep, so the maximum number of runs a page can store is 2048/6 = 341. Each value recorded in the run sextet is shifted by a fixed value. The shifts are 103 for X data and 22 for Y data. The offsets are subtracted from every sextet term.

Note: When collecting fifo data, the IP sometimes records an ending X, which is less than the beginning X. In this case, the ending is set X to the maximum column (755).

4. Source
   a. MEASURE.C
   b. IMAGER.C
   c. DRIVERS.C
5. Errors
   a. IP status bits indicate errors (see hardware explanation for error details).
   b. Image memory buffer can overflow (i.e. tries to store more than 341 runs).
C. Gather Spots
   1. Procedure
      a. Group all page 1 runs into a new center-of-mass (CM) table
      b. Group all page 2 runs into existing CM table
   2. Equations: NONE
   3. Data
      a. CM table
         The CM table contains information about each spot. The information includes: horizontal and vertical base positions, vertical weighted sum of runs, sum of all run lengths (area), floating point center-of-mass (horizontal & vertical), spot identifier, and bad spot indicator flag. The base positions are the horizontal and vertical positions of the first run found for that particular spot. The vertical weighted sum of runs is computed by multiplying each run length by its row, and adding all of the terms together for a given spot. See CM.H for the definition of the CM data type.
   4. Source
      a. FIFO2CMT.S07
      b. CM.H
   5. Errors
      a. Too many spots in CM table (more than 4)
      b. Too few spots (less than 4)
D. Verify Basic Data Set
   1. Procedure
      a. Remove all bad or questionable spots
      b. Check that we have exactly four spots
      c. Check that the areas of all spots are within set limits
      d. Check that no spots are too close to the CCD edge
   2. Equations: NONE
   3. Data: NONE
   4. Source
      a. TOSSBAD.S07
      b. FILTERS.S07
      c. BORDER.C
   5. Errors
      a. Number of spots not equal to 4
      b. Spot areas exceed limits
      c. Spots too close to allowable border E. Identify Spots
  1. Procedure
    a. First spot in table is spot #1
    b. Last spot in table is spot #4
    c. Middle two spots based on horizontal positions are #2 & #3.
      -if second spot hor. < third spot hor., then okay else swap them
  2. Equations: NONE
  3. Data
    a. Cm[i].ident is set to values 1 through 4, in that order
  4. Source
    a. IDSPOTS.S07
  5. Errors
    a. Unable to identify correctly
F. Calculate Centers-of-Mass for Each Spot
  1. Procedure
  2. Equations
    a. Horizontal $$horCM = \frac{(\text{sum of all beg x and end x values})}{(\text{number of runs}) * (2) * (\text{horizontal pixels per mm})}$$

Example:  beg X   row   end X

Run #1:   114    71    129
Run #2:   115    73    131
Run #3:   113    75    132
Run #4:   114    77    128

Sum of all beg x and end x values =
114+129-1+115+131-1+113-132-1+114+128-1 = 972
Number of runs = 4
Horizontal pixels per mm = 117.6470588
horCM = 1.03275 mm NOTE: all runs have been corrected for offsets, (See IV.B.3.A)

b. Vertical $$verCM = \frac{(\text{sum of all (run rows * run length)})}{(\text{sum of all run lengths}) * (\text{vertical pixels per mm})}$$

Example:    beg X    row    end X

Run #1:    123    92    149
Run #2:    120    94    151
Run #3:    121    96    150
Run #4:    122    98    150

Sum of all (run rows * run length) =
  92*26+94*31+96*29+98*28 = 10834

Sum of all run lengths = 26+31+29+28 = 114
Vertical pixels per mm = 101.2658228 verCM = 0.93847149 mm

NOTE: All run values have been corrected for offsets (see IV.B.3.A).

3. Data
   a. Cm[i].realHor set to CM horizontal position, in mm
   b. Cm[i].realVer set to CM vertical position, in mm
4. Source
   a. REALCMS.S07
5. Errors: NONE G. Correct Spot Centroids for Lens Distortions
1. Procedure
   a. Feed each image space CM pair through transform equation
   b. Obtain new CM object space pair
2. Equations The Keratometer uses a fourth-order lens correction. The parameters are derived during a camera calibration procedure. The equation requires an iterative solution performed pr.numCCDIter (2) times. The general equation is:

$(x-xp) + (x-xp)*(l1 + l2*r**2 + l3*r**4)$
$+ (p1*(r**2 + 2*xbar**2) + 2*p2*xbar**2*ybar**2)*(1 + p3*r**2)$
$- f* (m11*(x-xc) + m12*(y-yc) + m13*(z-zc)) /$
$(m31*(x-xc) + m32*(y-yc) + m33*(z-zc)) = 0$ where: xbar = x - xp
       ybar = y - xp
       r2 = xbar2 + ybar**2

This is solved for the x and y transformed (object) points.

3. Data
   a. Cm[i].realHor/realVer values are transformed to object space.
4. Source
   a. DISTORT.S07
5. Errors: NONE H. Calculate Base Curve Powers and Axis Angle
  1. Procedure: NONE
  2. Equations
     The following equations determine the base curve powers and axis angle from the spot centroids:

```
x1c = y1c = 0 ;
x2c = (cm[1].realHor-cm[0].realHor)+(cm[3].realHor-cm[2].realHor);
y2c = (cm[1].realVer-cm[0].realVer)+(cm[3].realVer-cm[2].realVer);
x3c = (cm[2].realHor-cm[0].realHor)+(cm[3].realHor-cm[1].realHor);
y3c = (cm[2].realVer-cm[0].realVer)+(cm[3].realVer-cm[1].realVer);
bterm = -( (x2c * y3b) + (y3c * x2b) - (x3c * y2b) - (y2c * x3b);
cterm = (x2c * y3c) - (x3c * y2c);
sterm = bterm*bterm - 4*aterm*cterm;
if sterm close to 0, then set sterm = 0;
sterm = squareroot(sterm);
majorAxis = (-b - s)/(2 * a);
minorAxis = (+b - s)/(2 * a);
if minorAxis < majorAxis, then swap the two;
baseCurve1 = dk_of_cal_object / majorAxis;
baseCurve2 = dk_of_cal_object / minorAxis;
if sterm = 0, then axis = 0;
else axis = arctan(-(x2c - majorAxis*x2b)/(y2c - majorAxis*y2b));
or axis = arctan(-(x3c - majorAxis*x3b)/(y3c - majorAxis*y3b));
if axis < 0, then add 180;
if cylinder < 0.125, then axis = 0;
```

3. Data
     a. BaseCurve1, baseCurve2 and axis determined; in re structure
  4. Source
     a. CALC.S07
  5. Errors: NONE I. Calculate Torricity
  1. Procedure
  2. Equations Torricity = abs( ((cm[2].realHor-cm[0].realHor) -
                 (cm[3].realHor-cm[1].realHor)) -
                 ((sc.vi[2].hor-sc.vi[0].hor) -
                 (sc.vi[3].hor-sc.vi[1].hor)) ) +

```
abs( ((cm[1].realVer-cm[0].realVer) -
(cm[3].realVer-cm[2].realVer)) -
((sc.vi[1].ver-sc.vi[0].ver) -
(sc.vi[3].ver-sc.vi[2].ver)) )
``` where; cm[0..3] are the centers-of-mass of spots 1 through 4, respectively, and sc.vi[0..3] are the centers-of-mass of the same spots from calibration.

if torricity > torric limit, then set torric flag in re structure

3. Data
   a. Va.torricity value computed
   b. Re.nonTorric set if TRUE
4. Source
   a. CALC.S07
5. Errors: NONE
J. Check for Resonable Values
  1. Procedure
     a. Test for base curves between 28 and 62 diopters
     b. Test for cylinder less than 10 diopters
  2. Equations: arithmetic comparisons from above
  3. Data: NONE
  4. Source
     a. FILTERS.S07
  5. Errors
     a. Out-of-range error if any test fails
K. Que Results
  1. Procedure
     a. Keep the five most recent successful readings
     b. Take readings until three are within pr.queueRange
     c. When three readings are within range, average them
     d. If any of the three is non-torric, mark reading non-torric
  2. Equations
     a. Base curves and axis angle are scalar averaged
     b. Angles may need manipulation before combining
  3. Data
     a. Re.sphere/.cylinder/.axis values calculated
  4. Source
     a. QUEUE.S07
  5. Errors: NONE
L. Read Level Angle
  1. Procedure
     a. Turn projector and alignment LED's off
     b. Turn level LED's on c. Set threshold value
  d. Dummy command to IP and delay 30 msec for field soak
  e. Get a page of image data
  f. Turn level LED's off
  g. Process level image data
  h. If angle ref is ground and level read okay, then incorporate into results
 2. Equations: NONE
 3. Data: NONE
 4. Source
  a. MEASURE.C
  b. LEVEL.S07
 5. Errors
  a. Image processor returned error bits
  b. Not enough image data
  c. Unable to process image data
M. Store Results
 1. Procedure
  a. Store base curves, axis angle, and stat into storage variable
 2. Equations: NONE
 3. Data
  a. OdResults[]/osResults[], based on which eye and field measured
 4. Source
  a. RESULTS.C
 5. Errors: NONE
N. Display Results
 1. Procedure
  a. Load results into re structure
  b. Round to desired resolution (0.125/0.01)
  c. Convert to selected display format (base curves/pos cyl/neg cyl)
  d. Convert results from MATH11 REAL format to IEEE floating point
  e. If units = diopters, then display numbers
  f. Display axis angle
  g. If units = mm, then display numbers
  h. If non-torric, then light irregular cornea icon
  i. Flash level/degree icons if handle selected or error reading level
 2. Equations: NONE
 3. Data: NONE
 4. Source
  a. DISPLAY.C
  b. LCD.C
 5. Errors: NONE It can therefore be seen that the present invention, in its preferred embodiment, achieves at least all the inventions stated objectives. The invention can take many forms and embodiments. The preferred embodiment is given by way of example only, and not by way of limitation to the invention. The true essence and spirit of this invention are defined in the appended claims, and it is not intended that the embodiment of the invention presented herein should limit the scope thereof.

As a primary example, the present invention can be utilized to determine the curvature of any curved surface which allows reflection to the extent needed for the image processing to function. The device therefore could be utilized to, for example, insure that field ball bearings are being manufactured to the required specifications.

Other uses are possible. Additionally, other features, additions, and enhancements are possible.

/
/
/
/
/
/
/
/
/
/

What is claimed is:

1. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

processing means in the housing means for analyzing the recorded received images to derive keratometric readings of the patient's eye; and a leveling means for automatically confirming whether the housing means is leveled with respect to a predetermined direction.

2. The keratometer means of claim 1 wherein the projector means comprises a plurality of projection assemblies each including a light source, a pin hole, and a lens.

3. The keratometer means of claim 2 wherein the projection assemblies are positioned circumferentially around an optical axis and angled towards that axis.

4. The keratometer means of claim 3 wherein each projector assembly is angled at the same angle with respect to the optical axis.

5. The keratometer means of claim 2 wherein each projection assembly includes a plurality of light sources.

6. The keratometer means of claim 5 wherein the plurality of light sources are aligned generally along a plane which is normal to an axis through the pin hole and lens.

7. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

the imaging means comprises an area imager consisting of a matrix of pixels, each pixels producing a signal proportional to the intensity of light received at the pixel;

processing means in the housing means for analyzing the recorded received images to derive keratometric readings of the patient's eye; and a leveling means for automatically confirming whether the housing means is leveled with respect to a predetermined direction.

8. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

processing means in the housing means for analyzing the recorded received images to derive keratometric readings of the patient's eye;

an alignment means for aligning the projector means with respect to the patient's eye, the alignment means including an eye piece for allowing a user of the keratometer means to view the patient's eye and the collimated lights sources from the projector means; and a leveling means for automatically confirming whether the housing means is leveled with respect to a predetermined direction.

9. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

processing means in the housing means for analyzing the recorded received images to derive keratometric readings of the patient's eye;

a fixation means for providing the patient with a light source upon which to fixate; and a leveling means for automatically confirming whether the housing means is leveled with respect to a predetermined direction.

10. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

processing means in the housing means for analyzing the recorded received images to derive keratometric readings of the patient's eye; and further comprising a leveling means for automatically confirming whether the housing means is leveled with respect to a predetermined direction, the leveling means including a chamber at least partially filled with a fluid and a back-lighting source, the image of the fluid in the chamber being captured by the imaging means and the processing means for analyzing whether the top level of the fluid is correctly positioned with respect to a frame of reference of the imaging means.

11. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

processing means in the housing means for analyzing the recorded received images to derive keratometric readings of the patient's eye;

a ring of one or more light sources which project a ring of light onto the patient's eye to allow testing of the nature of the eye; and a leveling means for automatically confirming whether the housing means is leveled with respect to a predetermined direction.

12. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

processing means in the housing means for analyzing the recorded received images to derive keratometric readings of the patient's eye;

further comprising a display means in the housing means for displaying information related to the keratometric readings; and a leveling means for automatically confirming whether the housing means is leveled with respect to a predetermined direction.

13. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

processing means in the housing means for analyzing the recorded received images to derive keratometric readings of the patient's eye;

control means for selecting operational modes and functions for the keratometer means; and a leveling means for automatically confirming whether the housing means is leveled with respect to a predetermined direction.

14. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

processing means in the housing means for analyzing the recorded received images to derive keratometric readings of the patient's eye;

further comprising battery power means for providing power to the projector means, imaging means, and processing means; and a leveling means for automatically confirming whether the housing means is leveled with respect to a predetermined direction.

15. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye;

processing means in the housing means for analyzing the recorded received images to derive keratometric readings of the patient's eye;

means for connecting a battery within the keratometer means with a recharging means such that the battery may be periodically recharged; and a leveling means for automatically confirming whether the housing means is leveled with respect to a predetermined direction.

16. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye; and the imaging means comprises a CCD camera;

processing means in the housing means for analyzing the recorded received images to derive keratometric readings of the patient's eye; and a leveling means for automatically confirming whether the housing means is leveled with respect to a predetermined direction.

17. A keratometer means comprising:

a portable housing means including a hand grip section;

a projector means in the housing means for projecting a pattern of collimated light sources onto a patient's eye;

an imaging means in the housing means for capturing and recording received images, including reflection of the pattern of collimated light sources from the patient's eye; and processing means in the housing for analyzing the recorded received images to derive keratometric readings of the patient's eye;

processing means in the housing for analyzing the recorded received images to derive keratometric readings of the patient's eye;

an alignment means for providing a user with a light source indicating a point at which the patient's eye should be positioned for correct up/down and left/right alignment; and a leveling means for automatically confirming whether the housing means is leveled with respect to a predetermined direction.

\* \* \* \* \*